US008858930B2

(12) United States Patent
Zhu et al.

(10) Patent No.: US 8,858,930 B2
(45) Date of Patent: Oct. 14, 2014

(54) **LIVE ATTENUATED BACTERIAL VACCINE TO REDUCE OR INHIBIT CARRIAGE AND SHEDDING OF ENTEROHEMORRHAGIC *ESCHERICHIA COLI* IN CATTLE**

(75) Inventors: Chengru Zhu, Albuquerque, NM (US); Edgar Boedeker, Placitas, NM (US)

(73) Assignees: Chengru Zhu, Cartonsville, MD (US); The United States of America as Represented by the Department of Veteran Affairs, Washington, DC (US)

( * ) Notice: Subject to any disclaimer, the term of this patent is extended or adjusted under 35 U.S.C. 154(b) by 1920 days.

(21) Appl. No.: 11/666,251

(22) PCT Filed: Oct. 26, 2005

(86) PCT No.: PCT/US2005/038364
§ 371 (c)(1),
(2), (4) Date: Jun. 2, 2008

(87) PCT Pub. No.: WO2006/047517
PCT Pub. Date: May 4, 2006

(65) Prior Publication Data
US 2008/0286310 A1 Nov. 20, 2008

Related U.S. Application Data

(60) Provisional application No. 60/621,872, filed on Oct. 26, 2004.

(51) Int. Cl.
*A01N 63/00* (2006.01)
*A61K 39/108* (2006.01)
*A61K 39/02* (2006.01)
*C07K 14/245* (2006.01)
*C12N 1/36* (2006.01)
*A61K 39/00* (2006.01)

(52) U.S. Cl.
CPC ............ *A61K 39/0258* (2013.01); *C07K 14/245* (2013.01); *A61K 2039/542* (2013.01); *A61K 2039/522* (2013.01); *C12N 1/36* (2013.01); *A61K 2039/54* (2013.01); *Y10S 424/823* (2013.01)
USPC .................... 424/93.4; 424/235.1; 424/200.1; 424/234.1; 424/241.1; 424/257.1; 424/93.48; 424/823

(58) Field of Classification Search
None
See application file for complete search history.

(56) References Cited

PUBLICATIONS

Woodward et al. Int. J. Med. Microbiol. 293: 299-308, Aug. 2003.*
Fitzhenry et al. Gut 50: 180-185, 2002.*
Marches 0, Ledger TN, Boury M, Ohara M, Tu X, Goffaux F, et al. Enteropathogenic and enterohaemorrhagic *Escherichia coli* deliver a novel effector called Cif, which blocks cell cycle G2/M transition. Mol Microbiol, 50:1553-67 (2003).
Marches, 0., J. P. Nougayrede, S. Boullier, J. Mainil, G. Charlier, I. Raymond, P. Pohl, M. Boury, J. De Rycke, A. Milon, and E. Oswald. Role of Tir and Intimin in the virulence of rabbit enteropathogenic *Escherichia coil* serotype 0103:H2. Infect. Immun. 68:2171-2182 (2000).
Marques, L. R., Moore, M. A., Wells, J. G., Wachsmuth, I. K., and O'Brien, A. D. Production of Shiga-like toxin by *Escherichia coll*. J.Infect.Dis. 154:338-341 (1986).
Matussek, A., Lauber, J., Bergau, A., Hansen, W., Rohde, M., Dittmar, K. E., Gunzer, M., Mengel, M., Gatzlaff, P., Hartmann, M., Buer, J., and Gunzer, F. Molecular and functional analysis of Shiga toxin-induced response patterns in human vascular endothelial cells. Blood 102:1323-1332 (2003).
McDaniel TK. Kaper JB. A cloned pathogenicity island from enteropathogenic *Escherichia coil* confers the attaching and effacing phenotype on *E. coil* K-12. Mol Microbiol, 23:399-407 (1997).
McKee, M. L. and A. D. O'Brien. Truncated enterohemorrhagic *Escherichia coli* (EHEC) 0157:H7 intimin (EaeA) fusion proteins promote adherence of EHEC strains to HEp-2 cells. Infect. Immun. 64:2225-2233 (1996).
McNamara, B. P., A. Koutsouris, C. B. O'Connell, J. P. Nougayrede, M. S. Donnenberg, and G. Hecht. Translocated EspF protein from enteropathogenic *Escherichia coli* disrupts host intestinal barrier function. J. Clin. Invest. 107:621-629 (2001).
Mead, P. S., Slutsker, L, Dietz, V., McCaig, L. F., Bresee, J. S., Shapiro, C., Griffin, P. M., and Tauxe, R. V. Food related illness and death in the United States. Emerg.Infect.Dis. 5:607-625 (1999).
Mellies JL, Elliott SL, Sperandio V, Donnenberg MS, Kaper JB. The Per regulon of enteropathogenic *Escherichia coli*: identification of a regulatory cascade and a novel transcriptional activator, the locus of enterocyte effacement (LEE)-encoded regulator (Ler). Mol Microbiol, 33:296-306 (1999).
Mesteky, Newby, In: Local immune response of the gut, CRC Press, Newby and Stocks Eds, 143-160 (1987).
Miller JH. Experiments in Molecular Genetics. Cold Spring Harbor: Cold Spring Harbor Laboratory Press (1972).
Mitchell, L. A. and Galun, E. Rectal immunization of mice with hepatitis A vaccine induces stronger systemic and local immune responses than parenteral immunization. Vaccine, 21: 1527-1538 (2003a).
Mobassaleh, M., Donohue-Rolfe, A., Jacewicz, M., Grand, R. J., and Keusch, G. T. Pathogenesis of *Shigella* diarrhea: evidence for a developmentally regulated glycolipid receptor for *Shigella* toxin involved in the fluid secretory response of rabbit small intestine. J.Infect.Dis. 157:1023-1031 (1988).

(Continued)

*Primary Examiner* — S. Devi
(74) *Attorney, Agent, or Firm* — Henry D. Coleman; R. Neil Sudol

(57) ABSTRACT

The invention provides live, attenuated enterohemorrhagic *Escherichia coli* (EHEC) bacteria in which the Shiga toxin coding sequences are deleted to abolish Shiga toxin production and one or more of the nucleotide sequences for the bacterial adhesin protein intimin, the locus of enterocyte effacement encoded regulator, and the translocated intimin receptor are mutated to inactivate the activity of the encoded protein(s). This live, attenuated *E. coli* bacteria is used in a vaccine for reducing or inhibiting carriage and shedding of EHEC in cattle.

6 Claims, 16 Drawing Sheets

(56) References Cited

PUBLICATIONS

Moon, H. W., Whipp, S. C., Argenzio, R. A., Levine, M. M., and Giannella, R. A. Attaching and effacing activities of rabbit and human enteropathogenic *Escherichia coil* in pig and rabbit intestines. Infect. Immun. 41:1340-1351 (1983).

Nagano, K., Sugisaki, T., Taguchi, K., Hara, T., Naiki, M., and Mori, H. A murine model of enterohemorrhagic *Escherichia coli* O157:H7 infection to assess immunopotentiating activity of drugs on mucosal immunity: effect of drugs. J.Pharmacol.Sci. 91:219-228 (2003).

Nagano, K., Taguchi, K., Hara, T., Yokoyama, S., Kawada, K., and Mori, H. Adhesion and colonization of enterohemorrhagic *Escherichia coli* O157:H7 in cecum of mice. Microbiol.Immunol. 47:125-132 (2003).

Nakase, H., Okazaki, K., Tabata, Y., Uchida, K., Uose, S., Ohana, M., Nishi, T., Watanabe, T., Matsuura, M., Hisatsune, H., Matsumura, K., Itoh, T., Kawanami, C., and Chiba, T. Rectal immunization with antigen-containing microspheres induces stronger Th2 responses than oral immunization: a new method for vaccination. Vaccine 20:377-384 (2001).

Nataro JP, Kaper JB. Diarrheagenic *Escherichia coli*. Clin Microbiol Rev, 11:142-201 (1998).

Naylor S Low C, 3 Besser T 4 Mahajan a 5 Gunn G 6 Pearce M 7 McKendrick I 8 Donachie W 9 Smith D. *Escherichia coil* 0157:H7 Colonisation of the Bovine Gi Tract. Absrt. 0-8, 5th International Symposium on 'Shiga Toxin (Verocytotoxin)—Producing *Escherichia coil* Infections, Scotland (2003).

Nicholls, L., Grant, T. H., and Robins-Browne, R. M. Identification of a novel genetic locus that is required for in vitro adhesion of a clinical isolate of enterohaemorrhagic *Escherichia coli* to epithelial cells. Mol.Microbiol. 35:275-288 (2000).

Nishikawa K, Matsuoka K, Kita E, Okabe N, Mizuguchi M, Hino K, Miyazawa S, Yamasaki C, Aoki J, Takashima S, Yamakawa Y, Nishijima M, Terunuma D, Kuzuhara H, Natori Y. A therapeutic agent with oriented carbohydrates for treatment of infections by Shiga toxin-producing *Escherichia coli* 0157:H7. Proc. Natl. Acad. Sci. U. S A. 99:7669-7674 (2002).

Noel JM, Wolf MK McQueen C Fleming E Pineiro-Carrero V Boedeker E. RDEC-1 infection is protective against challenge with Shiga-like toxin-I producing, isogenic strain (RDEC-H19A): Histologic assessment correlates with clinical protection. E76. Abstracts of the 95th General Meeting ASM. (1995).

Noel, J. M. and Boedeker, E. C. Enterohemorrhagic *Escherichia coli*: a family of emerging pathogens. Dig.Dis. 15:67-91 (1997).

Noriega FR, Losonsky G, Wang JY, Formal S B, Levine MM. Further characterization of delta aroA delta virG *Shigella flexneri* 2a strain CVD 1203 as a mucosal *Shigella* vaccine and as a live-vector vaccine for delivering antigens of enterotoxigenic *Escherichia coli*. Infect Immun, 64:23-7 (1996).

O'Brien, A. D., V. L. Tesh, A. Donohue-Rolfe, M. P. Jackson, S. Olsnes, K. Sandvig, A. A. Lindberg, and G. T. Keusch. Shiga toxin: biochemistry, genetics, mode of action, and role in pathogenesis. Curr. Top. Microbiol. Immunol. 180:65-94 (1992).

Ogierman M A, Paton AW, Paton JC. Up-regulation of both intimin and eae-independent adherence of shiga toxigenic *Escherichia coli* 0157 by ler and phenotypic impact of a naturally occurring ler mutation. Infect Immun, 68:5344-53 (2000).

Ojeda, A., Prado, V., Martinez, J., Arellano, C., Borczyk, A., Johnson, W., Lior, H., and Levine, M. M. Sorbitol-negative phenotype among enterohemorrhagic *Escherichia coil* strains of different serotypes and from different sources. J.Clin. Microbiol. 33:2199-2201 (2000).

Omisakin, F., MacRae, M., Ogden, I. D., and Strachan, N. J. Concentration and prevalence of *Escherichia coil* 0157 in cattle feces at slaughter. Appl.Environ.Microbiol. 69:2444-2447 (2003).

Oswald, E., H. Schmidt, S. Morabito, H. Karch, O. Marches, and A. Caprioli. Typing of intimin genes in human and animal enterohemorrhagic and enteropathogenic *Escherichia coli*: characterization of a new intimin variant. Infect. Immun. 68:64-71 (2000).

Pallen MJ, Chaudhuri RR, Henderson IR. Genomic analysis of secretion systems. Curr Opin Microbiol, 6:519-27 (2003).

Park, C. H., Gates, K. M., Vandel, N. M., and Nixon, D. L. Isolation of Shiga-like toxin producing *Escherichia coil*. (0157 and non-0157) in a community hospital. Diagn. Microbiol. Infect.Dis. 26:69-72 (1996).

Pascual et al. Immuno. Methods., 5:56-72 (1994).

Paton, J. C. and Paton, A. W. Pathogenesis and diagnosis of Shiga toxin-producing *Escherichia coli* infections. Clin. Microbiol. Rev. 11:450-479 (1998).

Pearson, G. R., Watson, C. A., Hall, G. A., and Wray, C. Natural infection with an attaching and effacing *Escherichia coil* in the small and large intestines of a calf with diarrhoea. Vet.Rec. 124:297-299 (1989).

Peeters JE, Geeroms R, Orskov F. Biotype, serotype, and pathogenicity of attaching and effacing enteropathogenic *Escherichia coli* strains isolated from diarrheic commercial rabbits. Infect Immun; 56:1442-8 (1988).

Perna, N. T., Mayhew, G. F., Posfai, G., Elliott, S., Donnenberg, M. S., Kaper, J. B., and Blattner, F. R. Molecular evolution of a pathogenicity island from enterohemorrhagic *Escherichia coli* O157:H7. Infect.Immun. 66:3810-3817 (1998).

Pierard, D., Van Etterijck, R., Breynaert, J., Moriau, L., and Lauwers, S. Results of screening for verocytotoxin-producing *Escherichia coil* in faeces in Belgium. Eur. J. Clin. Microbiol. Infect. Dis. 9:198-201 (1990).

Pospischil, A., Mainil, J. G., Baljer, G., and Moon, H. W. Attaching and effacing bacteria in the intestines of calves and cats with diarrhea. Vet.Pathol. 24:330-334 (1987).

Potter, A. A., Klashinsky, S., Li, Y., Frey, E., Townsend, H., Rogan, D., Erickson, G., Hinkley, S., Klopfenstein, T., Moxley, R. A., Smith, D. R., and Finlay, B. B. Decreased shedding of *Escherichia coli* O157:H7 by cattle following vaccination with type III secreted proteins. Vaccine 22: 362-369 (2004).

Rafiee, P., H. Leffler, J. C. Byrd, F. J. Cassels, E. C. Boedeker, and Y. S. Kim. A sialoglycoprotein complex linked to the microvillus cytoskeleton acts as a receptor for pilus (AF/R1) mediated adhesion of enteropathogenic *Escherichia coil* (RDEC-1) in rabbit small intestine. J. Cell Biol. 115:1021-1029 (1991).

Ramachandran, V., K. Brett, M. A. Hornitzky, M. Dowton, K. A. Bettelheim, M. J. Walker, and S. P. Djordjevic. Distribution of intimin subtypes among *Escherichia coli* isolates from ruminant and human sources. J. Clin. Microbiol. 41:5022-5032 (2003).

Rey, J., Blanco, J. E., Blanco, M., Mora, A., Dahbi, G., Alonso, J. M., Hermoso, M., Hermoso, J., Alonso, M. P., Usera, M. A., Gonzalez, E. A., Bernardez, M. I., and Blanco, J. Serotypes, phage types and virulence genes of shiga-producing *Escherichia coli* isolated from sheep in Spain. Vet.Microbiol. 94:47-56 (2003).

Rimsky S, Zuber F, Buckle M, Buc H. A molecular mechanism for the repression of transcription by the H-NS protein. Mol Microbiol, 42:1311-1323 (2001).

Robins-browne, R. M., Elliot, E., and Desmarchelier, P. Shiga toxin-producing *Escherichia coif* in Australia. In "*Escherichia coli* O157:H7 and other Shiga Toxing-rroducing *E. coli*" (J.B.Kaper and A. D. O'Brien, Eds.), ASM Press, Washington (1998).

Ruiz-Olvera P, Ruiz-Perez F, Sepulveda NV, Santiago-Machuca A, Maldonado-Rodriguez, R, Garcia-Elorriaga G, et al. Display and release of the *Plasmodium falciparum* circumsporozoite protein using the autotransporter MisL of *Salmonella enterica*. Plasmid, 50:12-27 (2003).

Ruiz-Perez F, Leon-Kempis R, Santiago-Machuca A. Ortega-Pierres G, Barry E, Levine M, et al. Expression of the *Plasmodium falciparum* immunodominant epitope (NANP)4 on the surface of *Salmonella enterica* using the autotransporter MisL. Infect Immun, 70:3611-20 (2002).

Sambrook J, Russell DW. Molecular cloning: a laboratory manual, 3rd ed. Cold Spring Harbor: Cold Spring Harbor Laboratory Press, (2001).

Sanchez-Sanmartin C, Bustamante VH, Calva E, Puente JL. Transcriptional regulation of the orf19 gene and the ti-cesT-eae operon of enteropathogenic *Escherichia coli*. J Bacteriol, 183:2823-33 (2001).

Sanderson, M. W., Besser, T. E., Gay, J. M., Gay, C. C., and Hancock, D. D. Fecal *Escherichia coli* O157:H7 shedding patterns of orally inoculated calves. Vet.Microbiol. 69:199 205 (1999).

(56) References Cited

OTHER PUBLICATIONS

Schoonderwoerd, M., Clarke, R. C., van Dreumel, A. A., and Rawluk, S. A. Colitis in calves: natural and experimental infection with a verotoxin-producing strain of *Escherichia coli* O111:NM. Can.J.Vet. Res. 52:484-487 (1988).

Adams LM, Simmons CP, Rezmann L, Strugnell RA, Robins-Browne RM. Identification and characterization of a K88- and CS31A-like operon of a rabbit enteropathogenic *Escherichia coil* strain which encodes fimbriae involved in the colonization of rabbit intestine. Infect Immun; 65:5222-30 (1997).

Adu-Bobie, J., Frankel, G., Bain, C., Goncalves, A. G., Trabulsi, L. R., Douce, G., Knutton, S., and Dougan, G. Detection of intimins alpha, beta, gamma, and delta, four intimin derivatives expressed by attaching and effacing microbial pathogens. J. Clin. Microbiol. 36:662-668 (1998).

Adu-Bobie, J., L. R. Trabulsi, M. M. Carneiro-Sampaio, G. Dougan, and G. Frankel. Identification of immunodominant regions within the C-terminal cell binding domain of intimin alpha and intimin beta from enteropathogenic *Escherichia coll*. Infect. Immun. 66:5643-5649 (1998).

Agin, T. S. and M. K. Wolf. Identification of a family of intimins common to *Escherichia coil* causing attaching effacing lesions in rabbits, humans, and swine. Infect. Immun. 65:320-326 (1997).

Agin, T. S. Boedeker E. C. Johnson L. A. Thate T. E. Russell R. S. Towards a vaccine for Shiga toxin-producing *Escherichia coll*. (STEC): Protection against hemorrhagic colitis in an animal model following immunization with a rabbit enteropathogenic *E. coll*. (REPEC) strain expressing truncated intimin. Abstracts of the 99th Gen.Mtng. ASM (1999).

Agin, T. S., Cantey, J. R., Boedeker, E. C., and Wolf, M. K. Characterization of the eaeA gene from rabbit enteropathogenic *Escherichia coil* strain RDEC-1 and comparison to other eaeA genes from bacteria that cause attaching-effacing lesions. FEMS Microbiol.Lett. 144:249-258 (1996).

Ahmed ZU, Sarker MR, Sack DA. Protection of adult rabbits and monkeys from lethal shigellosis by oral immunization with a thymine-requiring and temperature-sensitive mutant of *Shigella flexneri*. Vaccine, 8:153-58 (1990).

An H, Fairbrother JM, Dubreuil JD, Harel J. Cloning and characterization of the eae gene from a dog attaching and effacing *Escherichia coli* strain 4221. FEMS Microbiol Lett, 148:239-45 (1997).

Armstrong, G. D., P. C. Rowe, P. Goodyer, E. Orrbine, T. P. Klassen, G. Wells, A. MacKenzie, H. Lior, C. Blanchard, and F. Auclair. A phase I study of chemically synthesized verotoxin (Shiga-like toxin) Pk-trisaccharide receptors attached to chromosorb for preventing hemolytic-uremic syndrome. J. Infect. Dis. 171:1042-1045 (1995).

Badea, L, Doughty, S., Nicholls, L., Sloan, J., Robins-Browne, R. M., and Hartland, E. L. Contribution of Efal/LifA to the adherence of enteropathogenic *Escherichia coil* to epithelial cells. Microb.Pathog. 34:205-215 (2003).

Banatvala, N., Griffin, P. M., Greene, K. D., Barrett, T. J., Bibb, W. F., Green, J. H., and Wells, J. G. The United States National Prospective Hemolytic Uremic Syndrome Study: microbiologic, serologic, clinical, and epidemiologic findings. J.Infect.Dis., 183:1063-1070 (2001).

Berendson, R., C. P. Cheney, P.A. Schad, and E. C. Boedeker. Species-specific binding of purified pill (AF/RI) from the *Escherichia coli* RDEC-1 to rabbit intestinal mucosa. Gastroenterology 85:837-845 (1983).

Bielaszewska, M., I. Clarke, M. A. Karmali, and M. Petric. Localization of intravenously administered verocytotoxins (Shiga-like toxins) 1 and 2 in rabbits immunized with homologous and heterologous toxoids and toxin subunits. Infect Immun. 65:2509-16 (1997).

Bitzan, M. And Karch, H. Serological methods for the detection of STEC infections. In "*E. coil* Shiga toxin methods and protocols" (D. Philpott and F. Ebel, Eds.), pp. 27-43. Human Press Inc (2003).

Blanco, J. E, Blanco, M., Alonso, M. P., Mora, A., Dahbi, G., Coira, M. A., and Blanco, J. Serotypes, virulence genes, and intimin types of Shiga toxin (verotoxin)-producing *Escherichia coil* isolates from human patients: prevalence in Lugo, Spain, from 1992 through 1999. J.Clin.Microbiol. 42:311-319 (2004a).

Blanco, M., Blanco, J. E., Mora, A., Dahbi, G., Alonso, M. P., Gonzalez, E. A., Bernardez, M. I., and Blanco, J. Serotypes, virulence genes, and intimin types of Shiga toxin (verotoxin)-producing *Escherichia coli* isolates from cattle in Spain and identification of a new intimin variant gene (ede-xi). J.Clin.Microbiol. 42:64D-651 (2004a).

Blanc-Potard AB, Solomon F, Kayser J, Groisman EA. The SPI-3 pathogenicity island of *Salmonella enterica*. J. Bacteriol. 81:998-1004 (1999).

Black et al., J. infect. Dis., 155:1260-1265 (1987).

Boedeker EC, Cheney CP. Infection of rabbits with *E. coli* strain RDEC-I: a model for infections of human infants with enteropathogenic *E. coli* (EPEC) strains. In C. J. Pfeiffer (ed.), Animal Models of Intestinal Disease. Boca Raton: CRC Press, p. 27-40 (1985).

Bopp, C. A., Greene, K. D., Downes, F. P., Sowers, E. G., Wells, J. G., and Wachsmuth, I. K. Unusual verotoxin-producing *Escherichia coli* associated with hemorrhagic colitis. J. Clin. Microbiol. 25:1486-1489 (1987).

Bovie, C. F., Monreal, Z., Martinez, J., Arellano, C., and Prado, V. Detection and characterization of enterohaemorrhagic *Escherichia coli* in slaughtered cattle. Zentralbl. Veterinarmed. 44:273-279 (1997).

Boyce, T. G., Swerdlow, D. L., and Griffin, P. M. *Escherichia coli* O157:H7 and the hemolytic-uremic syndrome. N. Engl. J. Med. 333:364-368 (1995).

Bustamante, V. H., Santana, F. J., Galva, E., and Puente, J. L. Transcriptional regulation of type III secretion genes in enteropathogenic *Escherichia coli*: Ler antagonizes H-NS-dependent repression. Mol. Microbiol. 39:664-678 (2001).

Butterton JR, Boyko SA, Calderwood SB. Use of the *Vibrio cholerae* irgA gene as a locus for insertion and expression of heterologous antigens in *Cholera* vaccine strains. Vaccine, 11:1327-35 (1993).

Butterton JR, Ryan ET, Acheson DWK, Calderwood SB. Co-expression of the B subunit of Shiga Toxin 1 and EaeA from enterohemorrhagic *Escherichia coli* in *Vibrio cholerae* vaccine strains. Infect Immun, 65:2127-35 (1997).

Calderwood SB, Auclair F, Donohue RA, Keusch GT, Mekalanos JJ. Nucleotide sequence of the Shiga-like toxin genes of *Escherichia coli*. Proc Natl Acad Sci USA, 84:4364-8 (1987).

Camguilhem R, Milon A. Biotypes and 0 serogroups of *Escherichia coli* involved in intestinal infections of weaned rabbits:clues to diagnosis of pathogenic strains. J Clin Microbiol 27:743-7 (1989).

Cantey JR, Inman LR. Diarrhea due to *Escherichia coll*. strain RDEC-1 in the rabbit: the Peyer's patch as the initial site of attachment and colonization. J Infect Dis, 143:440-6 (1981).

Cantey, J. R. and R. K. Blake. Diarrhea due to *Escherichia coll*. in the rabbit: a novel mechanism. J. Infect. Dis. 135:454-462 (1977).

Cantey, J. R., R. K. Blake, J. R. Williford, and S. L. Moseley. Characterization of the *Escherichia coll*. AF/RI pilus operon: novel genes necessary for transcriptional regulation and for pilus-mediated adherence. Infect. Immun. 67:2292-2298 (1999).

Capozzo, A.V., V. Pistone Creydt, G. Dran, G. Fernandez, S. Gomez, L.V. Bentancor, C. Rubel, C. Ibarra, M. Isturiz, and M. S. Palermo. Development of DNA vaccines against hemolytic-uremic syndrome in a murine model. Infect. Immun. 71:3971-3978 (2003).

Carter, A. O., Borczyk, A. A., Carlson, J. A., Harvey, B., Hockin, J. C., Karmali, M. A., Krishnan, C., Korn, D. A., and Lior, H. A severe outbreak of *Escherichia coli* O157:H7-associated hemorrhagic colitis in a nursing home. N. Engl. J. Med 317:1496-1500 (1987).

China, B., Jacquemin, E., Devrin, A. C., Pirson, V., and Mainil, J. Heterogeneity of the eae genes in attaching/effacing *Escherichia coll*. from cattle: comparison with human strains. Res. Microbiol. 150:323-332 (1999).

Curtiss R III, Goldschmidt RM, Fletchhall NB, Kelly SM. Avirulent *Salmonella typhimurium* delta cya delta crp oral vaccine strains expressing a streptococcal colonization and virulence antigen. Vaccine, 6:155-60 (1988).

Dean-Nystrom, E. A. Bovine *Escherichia coli* O157:H7 infection medel. In "*E. coll*. Shiga Toxin methods and protocols" (D. Philpott and F. Ebel, Eds.), pp. 329-338. Human Press Inc. (2003).

(56) References Cited

OTHER PUBLICATIONS

Dean-Nystrom, E. A., L. J. Gansheroff, M. Mills, H. W. Moon, and A. D. O'Brien. Vaccination of pregnant dams with intimin (0157) protects suckling piglets from *Escherichia coli* O157:H7 infection. Infect. Immun. 70:2414-2418 (2002).

Deng, W., J. L. Puente, S. Gruenheid, Y. Li, B. A. Valiance, A. Vazquez, J. Barba, J. A. Ibarra, P. O'Donnell, P. Metalnikov, K. Ashman, S. Lee, D. Goode, T. Pawson, and B. B. Finlay, B. B. Dissecting virulence: Systematic and functional analyses of a pathogenicity island. Proc. Natl. Acad. Sci. U.S.A 101:3597-3602 (2004).

Deng, W., Y. Li, B. A. Vallance, and B. B. Finlay. Locus of enterocyte effacement from *Citrobacter rodentium*: sequence analysis and evidence for horizontal transfer among attaching and effacing pathogens. Infect. Immun. 69:6323-6335 (2001).

Desvaux M, Parham NJ, Henderson IR. The autotransporter secretion system. Res Microbiol. 155:53-60 (2004).

Donnenberg, M. S. and J. B. Kaper. Construction of an eae deletion mutant of enteropathogenic *Escherichia coli* by using a positive-selection suicide vector. Infect. Immun. 59:4310-4317 (1991).

Donnenberg, M. S., Tacket, C. O., James, S. P., Losonsky, G., Nataro, J. P., Wasserman, S. S., Kaper, J. B., and Levine, M. M. Role of the eaeA gene in experimental enteropathogenic *Escherichia coli* infection. J. Clin. Invest 92:1412-1417 (1993).

Donnenberg, M. S., Tzipori, S., McKee, M. L., O'Brien, A. D., Alroy, J., and Kaper, J. B. The role of the eae gene of enterohemorrhagic *Escherichia coli* in intimate attachment in vitro and in a porcine model. J Clin Invest 92:1418-1424 (1993).

Doyle, MP. Focusing on Cattle to Reduce the Incidence of *Escherichia coli* 0157 Infections in Humans. Absrt. 0-19, 5th International Symposium on 'Shiga Toxin (Verocytotoxin)—Producing *Escherichia coli* Infections, Scotland (2003).

Ebel, F., T. Podzadel, M. Rohde, A. U. Kresse, S. Kramer, C. Deibel, C. A. Guzman, and T. Chakraborty. Initial binding of Shiga toxin-producing *Escherichia coli* to host cells and subsequent induction of actin rearrangements depend on filamentous EspA-containing surface appendages. Mol. Microbiol. 30:147-161 (1998).

Edson, C. O., Ealding, W., and Lefkoowitz, J. A lavage technique allowing repeated measurement of IgA antibody in mouse lnteStillal secretions. J. Immunol. Methods 67:101-08 (1984).

Elliott SJ, Kaper JB. Role of type 1 fimbriae in EPEC infections. Microb Pathog 23:113-8 (1997).

Elliott, S. J., L. A. Wainwright, T. K. McDaniel, K. G. Jarvis, et al, The complete sequence of the locus of enterocyte effacement (LEE) from enteropathogenic *Escherichia call* E2348169. Mol. Microbiol. 28:1-4 (1998).

Elliott, S. J., Sperandio, V., Giron, J. A., Shin, S., Mellies, J. L., Wainwright, L., Hutcheson, S. W., McDaniel, T. K., and Kaper, J. B. The locus of enterocyte effacement (LEE)-encoded regulator controls expression of both LEE- and non-LEE-encoded virulence factors in enteropathogenic and enterohemorrhagic *Escherichia coll*. Infect.Immun. 68:6115-6126 (2000).

Fiederling F, Boury M, Petit C, Milon A. Adhesive factor/rabbit 2, a new fimbrial adhesin and a virulence factor from *Escherichia coli* 0103, a serogroup enteropathogenic for rabbits. Infect Immun, 65:847-51 (1997).

Frankel, G, A. D. Philips, M. Novakova, M. Batchelor, S. Hicks, and G. Dougan. Generation of *Escherichia coil* intimin derivatives with differing biological activities using site-directed mutagenesis of the intimin C-terminus domain. Mol. Microbiol. 29:559-570 (1998).

Scotland, S. M., Willshaw, G. A., Smith, H. R., and Rowe, B. Properties of strains of *Escherichia coli* O26:H11 in relation to their enteropathogenic or enterohemorrhagic classification. J.Infect.Dis. 162:1069-1074 (1990).

Senanayake SD, Brian DA. Precise large deletions by the PCR-based overlap extension methods. Mol Biotech, 4:13-15 (1995).

Sjogren, R., R. Neill, D. Rachmilewitz, D. Fritz, J. Newland, D. Sharpnack, C. Colleton, J. Fondacaro, P. Gemski, and E. C. Boedeker. Role of Shiga-like toxin I in bacterial enteritis: comparison between isogenic *Escherichia coli* strains induced in rabbits. Gastroenterology 106:306-317 (1994).

Sperandio V, Mellies JL, Delahay RM. Frankel G, Crawford, JA, NgUyen W, et al. Activation of enteropathogenic *Escherichia coli* (EPEC) LEE2 and LEE3 operons by Ler. Mol Microbiol, 38:781-93 (2000).

Sperandio, V., Mellies, J. L., Nguyen, W., Shin, S., and Kaper, J. B. Quorum sensing controls expression of the type III secretion gene transcription and protein secretion in enterohemorrhagic and enteropathogenic *Escherichia coll*. Proc. Natl. Acad. Sci. U.S.A 96:15196-15201 (1999).

Sperandio, V., Torres, A. G., Giron, J. A., and Kaper, J. B. Quorum sensing is a global regulatory mechanism in enterohemorrhagic *Escherichia coli*O157:H7. J.Bacteriol. 183:5187-5197 (2001).

Stevens, M. P., van Diemen, P. M., Frankel, G., Phillips, A. D., and Wallis, T. S. Efal influences colonization of the bovine intestine by shiga toxin-producing *Escherichia coil* serotypes 05 and 0111. Infect. Immun. 70:5158-5166 (2002).

Stordeur, P., China, B., Charlier, G., Roels, S., and Mainil, J. Clinical signs, reproduction of attaching/effacing lesions, and enterocyte invasion after oral inoculation of an 0118 enterohaemorrhagic *Escherichia coll*. in neonatal calves. Microbes. Infect. 2:17-24 (2000).

Sutton RG, Merson MH. Oral typhoid vaccine Ty2la. Lancet, 5:523 (1983).

Tacket CO, Hone DM, Losonsky GA, Guers L, Edelman R, Levine MM. Clinical acceptability and immunogenicity of CVD 908 *Salmonella typhi* vaccine strain. Vaccine, 10:443-6 (1992).

Takeuchi A, Inman LR, O'Hanley PD, Cantey JR, Lushbaugh WB. Scanning and transmission electron microscopic study of *Escherichia coll*. 015 (RDEC-1) enteric infection in rabbits. Infect Immun, 19:686-94 (1978).

Tarr, C. L. and Whittam, T. S. Molecular evolution of the intimin gene in 0111 clones of pathogenic *Escherichia coli*. J. Bacteriol. 184:479-487 (2002).

Tarr, P. I. and Neill, M. A. Perspective: the problem of non-0157:H7 shiga toxin (Verocytotoxin)-producing *Escherichia coll*. J.Infect.Dis. 174:1136-1139 (1996).

Tatsuno, I., Node, M., Abe, H., Miki, T., Makino, K., Shinagawa, H., Taguchi, H., Kamiya, S., Hayashi, T., and Sasakawa, C. toxB Gene on pO157 of Enterohemorrhagic *Escherichia coli* O157:H7 Is Required for Full Epithelial Cell Adherence Phenotype. Infect.Immun. 69:6660-6669 (2001).

Tesh, V. L. and O'Brien, A. D. The pathogenic mechanisms of Shiga toxin and the Shiga-like toxins. Mol.Microbiol. 5:1817-1822 (1991).

Tkalcic, S., Zhao, T., Harmon, B. G., Doyle, M. P., Brown, C. A., and Zhao, P. Fecal shedding of enterohemorrhagic *Escherichia coli* in weaned calves following treatment with probiotic *Escherichia coli*. J.Food Prot. 66:1184-1189 (2003).

Torres, A. G. and Kaper, J. B. Multiple elements controlling adherence of enterohemorrhagic *Escherichia coli* O157:H7 to HeLa cells. Infect.Immun. 71:4985-4995 (2003).

Torres, A. G., Giron, J. A., Perna, N. T., Burland, V., Blattner, F. R., Avelino-Flores, F., and Kaper, J. B. Identification and characterization of 1pfABCC'DE, a fimbrial operon of enterohemorrhagic *Escherichia call* O157:H7. Infect.Immun. 70:5416-5427 (2002).

Tzipori, S., Gunzer, F., Donnenberg, M. S., de Montigny, L, Kaper, J. B., and Donohue-Rolfe, A. The role of the eaeA gene in diarrhea and neurological complications in a gnotobiotic piglet model of enterohemorrhagic *Escherichia coli* infection. Infectirnmun. 63:3621-3627 (1995).

Uchida, C., Y. Kimura, S. Kubota, and O. Sasaki. Protective effect of *Pasteurella multocida* cell-free antigen and toxoid against challenge with toxigenic strains of *Pasteurella multocida* in mice. J. Vet. Med. Sci. 65:737-740 (2003).

Veiga E, de Lorenzo V, Fernandez LA. Probing secretion and translocation of a beta-autotransporter using a reporter single-chain Fv as a cognate passenger domain. Mol Microbiol, 33:1232-43 (1999).

Von Moll LK, Cantey JR. Peyer's patch adherence of enteropathogenic *Escherichia coil* strains in rabbits. Infect Immun, 65:3788-93 (1997).

Wandersman C, Delepelaire P. ToIC, an *Escherichia coli*. outer membrane protein required for hemolysin secretion. Proc Natl Acad Sci USA, 78:4776-80 (1990).

(56) References Cited

OTHER PUBLICATIONS

Watanabe M, Matsuoka K, Kita E, Igai K, Higashi N, Miyagawa A, Watanabe T, Yanoshita R, Samejima Y, Terunuma D, Natori Y, Nishikawa K. Oral therapeutic agents with highly clustered globotriose for treatment of Shiga toxigenic *Escherichia coli*. infections. J. Infect. Dis. 189:360-368 (2004).
Willshaw, G. A., Scotland, S. M., Smith, H. R., and Rowe, B.. Properties of Vero cytotoxin-producing *Escherichia coil* of human origin of 0 serogroups other than 0157. J.Infect.Dis. 166:797-802 (1992).
Wolf MK, Andrews GP, Fritz DL, Sjogren Jr. RW, Boedeker EC. Characterization of the plasmid from *Escherichia coil* RDEC-1 that mediates expression of adhesin AF/R1 and evidence that AF/R1 pill promote but are not essential for enteropathogenic disease. Infect Immun, 56:1846-57 (1988).
Wolf MK, Boedeker EC. Cloning of the genes for AF/Ri pili from rabbit enteroadherent *Escherichia coli* RDEC-1 and DNA sequence of the major structural subunit. Infect Immun, 58:1124-8 (1990).
Wray, C., McLaren, I., and Pearson, G. R. Occurrence of 'attaching and effacing' lesions in the small intestine of calves experimentally infected with bovine isolates of verocytotoxic *E coli*. Vet.Rec. 125:365-368 (1990).
Yamasaki, C., Natori, Y., Zeng, X. T., Ohmura, M., Yamasaki, S., Takeda, Y., and Natori, Y. Induction of cytokines in a human colon epithelial cell line by Shiga toxin 1 (Stxl) and Stx2 but not by nontoxic mutant Stxl which lacks N-glycosidase activity. FEBS Lett. 442:231-234 (1999).
Yokomizo, Y., Watanabe, F., Imada, Y., Inumaru, S., Yanaka, T., and Tsuji, T. Mucosal immunoadjuvant activity of the low toxic recombinant *Escherichia coli* heat-labile enterotoxin produced by *Bacillus brevis* for the bacterial subunit or component vaccine in pigs and cattle. Vet. Irnmunol. Immunopathol. 87:291-300 (2002).
Zhang, W. L., B. Kohler, E. Oswald, L. Beutin, H. Karch, S. Morabito, A. Caprioli, S. Suerbaum, and H. Schmidt. Genetic Diversity of Intimin Genes of Attaching and Effacing *Escherichia coil* Strains. J. Clin. Microbiol. 40:4486-4492 (2002).
Zhao, T., Tkalcic, S., Doyle, M. P., Harmon, B. G., Brown, C. A., and Zhao, P. Pathogenicity of enterohemorrhagic *Escherichia coli* in neonatal calves and evaluation of fecal shedding by treatment with probiotic *Escherichia coli*. J. Food Prot. 66:924-930 (2003).
Zhou, F., Kraehenbuhl, J. P., and Neutra, M. R. Mucosal IgA response to rectally administered antigen formulated in IgA-coated liposomes. Vaccine 13:637-644 (1995).
Zhu C, Agin TS, Elliott SJ, Johnson,LA, Thate TE, Kaper JB, et al. Complete nucleotide sequence and analysis of the locus of enterocyte effacement from rabbit diarrheagenic *Escherichia coli* RDEC-1. Infect Immun, 69:2107-15 (2001).
Zhu C, Feng S, Thate TE, Kaper JB, Boedeker EC. Towards a vaccine for attaching/effacing *Escherichia coli*: a LEE encoded regulator (ler) mutant of rabbit enteropathogenic *Escherichia coli* is attenuated, immunogenic, and protects pabbits from lethal challenge with the virulent wild-type strain. Vaccine (2004).
Zhu, C., J. Harel, F. Dumas, and J. M. Fairbrother. Identification of EaeA protein in the outer membrane of attaching and effacing *Escherichia* calf 045 from pigs. FEMS Microbiol. Lett. 129:237-242 (1995).
Zhu C, Harel J, Jacques M, Desautels C, Donnenberg MS, Beaudry M, Fairbrother JM. Virulence properties and attaching-effacing activity of *Escherichia coli* 045 from swine postweaning diarrhea. Infect Immun, 62:4153-9 (1994).
Zhu, C, Feng, S, Thate, T, Kaper, JB, and Boedeker, EC. Analysis of the ler (Lee Encoded Regulator) Gene of a Rabbit Enteropathogenic *Escherichia coli* (O103:H2) and Evaluation of Its in vivo Role in Virulence. B7 Abstracts of the 101th Gen. Mtng. ASM, Orlando, FL (2002).
Frankel, G., A. D. Phillips, M. Novakova, H. Field, D. C. Candy, D. B. Schauer, G. Douce, and G. Dougan. Intimin from enteropathogenic *Escherichia coil* restores murine virulence to a *Citrobacter rodentium* eaeA mutant: induction of an immunoglobulin A response to intimin and EspB. Infect. Immun. 64:5315-5325 (1996).

Frankel, G., D. C. Candy, E. Fabiani, J. Adu-Bobie, S. Gil, M. Novakova, A.D. Phillips, and G. Dougan, Molecular characterization of a carboxy-terminal eukaryotic-cell-binding domain of intimin from enteropathogenic *Escherichia coll*. Infect. Immun. 63:4323-4328 (1995).
Frankel, G., Lider, O., Hershkoviz, R., Mould, A. P., Kachalsky, S. G., Candy, D. C. A., Cahalon, L., Humphries, M. J., and Dougan, G. The cell-binding domain of intimin from enteropathogenic *Escherichia coli* binds to betal integrins. J. Biol. Chem. 271:20359-20364 (1996).
Funatogawa, K., Ide, T., Kirikae, F., Saruta, K., Nakano, M., and Kirikae, T. Use of immunoglobulin enriched bovine colostrum against oral challenge with enterohaemorrhagic *Escherichia coli* O157:H7 in mice. Microbiol. Immunol. 46:761-766 (2002).
Galan JE, Nakayama K, Curtiss R III. Cloning and characterization of the asd gene of *Salmonella typhimurium*: use in stable maintenance of recombinant plasmids in *Salmonella* vaccine strains. Gene, 94:29-35 (1990).
Galen JE, Nair J, Wang JY, Wasserman SS, Tanner MK, Sztein MB, et al. Optimization of plasmid maintenance in the attenuated live vector vaccine strain *Salmonella typhi* CVD 908-htrA. Infect Immun, 67:6424-33 (1999).
Gentry MK, Dalrymple JM. Quantitative microtiter cytotoxicity assay for Shiga toxin. J Clin. Microbiol., 12:361-6 (1980).
Gentschev I, Dietrich G, Goebel W. The *E. coli* a-hemolysin secretion system and its use in vaccine development. Trend Microbiol. 10:39-45 (2002).
Gentschev I, Hess J, Goebel W. Change in the cellular localization of alkaline phosphatase by alteration of its carboxy-terminal sequence. Mol Gen Genet, 222:211-6 (1990).
Gentschev I, Sokolovic Z, Mollenkopf HJ, Hess J, Kaufmann SH, Kuh M, et al. *Salmonella* strain secreting active listeriolysin changes its intracellular localization. Infect. Immun., 63:4202-5 (1995).
Ghaem-Maghami, M., C. P. Simmons, S. Daniell, M. Pizza, D. Lewis, G. Frankel, and G. Dougan. Intimin-specific immune responses prevent bacterial colonization by the attaching-effacing pathogen *Citrobacter rodentium*. Infect. Immun. 69:5597-5605 (2001).
Gray L, Mackman N, Nicaud JM, Holland IB. The carboxy-terminal region of haemolysin 2001 is required for secretion of the toxin from *Escherichia coli*. Mol Gen Genet, 205:127-33 (1986).
Griffin, P. M. and R. V. Tauxe. 1991. The epidemiology of infections caused by *Escherichia coli* O157:H7, other enterohemorrhagic *E coli*, and the associated hemolytic uremic syndrome. Epidemiol. Rev. 13:60-98.
Gyles, C. L. *Escherichia coli* verotoxins and other cytotoxins. In "*Escherichia coli* in domestic animals and humans" (C. L Gyles, Ed.), pp. 365-398. CAB international (1994).
Haack KR, Robinson CL, Miller KJ, Fowlkes JW, Mellies JL. Interaction of Ler at the LEES (tir) operon of enteropathogenic *Escherichia coli*. Infect Immun, 71:384-92 (2003).
Hane MW, Wood TH. *Escherichia coil* K-12 mutants resistant to nalidixic acid: genetic mapping and dominance studies. J Bacteriol, 99:238-41 (1969).
Hartland, E. L., M. Batchelor, R. M. Delahay, C. Hale, S. Matthews, G. Dougan, S. Knutton, I. Connerton, and G. Frankel. Binding of intimin from enteropathogenic *Escherichia coli* to Tir and to host cells. Mol. Microbiol. 32:151-158 (1999).
Hess J, Gentschev I, Goebel W, Jarchau T. Analysis of the haemolysin secretion system by PhoA-HlyA fusion proteins. Mol Gen Genet, 224:201-8 (1990).
Hicks, S., Frankel, G., Kaper, J. B., Dougan, G., and Phillips, A. D. Role of intimin and bundle-forming pill in enteropathogenic *Escherichia coil* adhesion to pediatric intestinal tissue in vitro. Infect. Immun. 66:1570-1578 (1998).
Hoiseth SK, Stocker BA. Aromatic-dependent *Salmonella typhimurium* are non-virulent and effective as live vaccines. Nature, 291:238-9 (1981).
Hone D, Attridge S, van den Bosch L, Hackett J. A chromosomal integration system for stabilization of heterologous genes in *Salmonella* based vaccine strains. Microb Pathog, 5:407-18 (1988).
Hopkins, S., Kraehenbuhl, J. P., Schodel, F., Potts, A., Peterson, D., De Grandi, P., and Nardelli-Haefliger, D. A recombinant *Salmonella*

(56) References Cited

OTHER PUBLICATIONS

*typhimurium* vaccine induces local immunity by four different routes of immunization. Infect. Immun. 63:3279-3286 (1995).

Hovde, C. J., Austin, P. R., Cloud, K. A., Williams, C. J., and Hunt, C. W. Effect of cattle diet on *Escherichia coil* O157:H7 acid resistance. Appl.Environ.Microbiol 65:3233-3235 (1999).

Hovde, C. J., Calderwood, S. B., Mekalanos, J. J., and Collier, R. J. Evidence that glutamic acid 167 is an active-site residue of Shiga-like toxin I. Proc.Natl.Acad.Sci.U.S.A, 85: 2568-2572 (1988).

Ishikawa, S., K. Kawahara,Y. Kagami, Y. Isshiki, A. Kaneko H. Matsui N. Okada, and H. Danbara. Protection against Shiga toxin 1 challenge by immunization of mice with purified mutant Shiga toxin 1. Infect Immun. 71:3235-9 (2003).

Jackson MP. Structure-function analyses of Shiga toxin and the Shiga-like toxins. Microb Pathog, 235-142. Department of Immunology and Microbiology, Wayne State University School of Medicine, Detroit, MI 48201 (1990).

Jackson, M. P., Wadolkowski, E. A., Weinstein, D. L., Holmes, R. K., and O'Brien, A. D. Functional analysis of the Shiga toxin and Shiga-like toxin type II variant binding subunits by using site-directed mutagenesis. J. Bacteriol. 172:653-657 (1990).

Janke, B. H., Francis, D. FL, Collins, J. E., Libal, M. C., Zeman, D. H., and Johnson, D. D. Attaching and effacing *Escherichia coil* infections in calves, pigs, lambs, and dogs. J.Vet.Diagn.lnvest 1:6-11 (1989).

Jerse, A. E., J. Yu, B. D. Tall, and J. B. Kaper. A genetic locus of enteropathogenic *Escherichia coil* necessary for the production of attaching and effacing lesions on tissue culture cells. Proc. Natl. Acad. Sci. U.S.A 87:7839-7843 (1990).

Judge, N. A., Mason, H. S., and O'Brien, A. D. Plant cell-based intimin vaccine given orally to mice primed with intimin reduces time of *Escherichia coli* O157:H7 shedding in feces. Infect.Immun. 72:168-175 (2004).

Kaper JB, Nataro JP, Mobley HL. Pathogenic *Escherichia coll*. Nat Rev Microbiol., 2:123-40 (2004).

Kaper, J. B., Enterohemorrhagic *Escherichia coli*. Curr.Opin. Microbiol. 1:103-108 (1998).

Kaper, J. B., J. P. Nataro, and H. L. Mobley. Pathogenic Escherichia coll. Nat Rev Microbiol. 2:123-40 (2004).

Karaolis, D. K., T. K. McDaniel, J. B. Kaper, and E. C. Boedeker. Cloning of the RDEC-1 locus of enterocyte effacement (LEE) and functional analysis of the phenotype on HEp-2 cells. Adv. Exp. Med. Biol. 412:241-245 (1997).

Karmali, M. A., Petric, M., Lim, C., Fleming, P. C., Arbus, G. S., and Lior, H. The association between idiopathic hemolytic uremic syndrome and infection by verotoxin-producing *Escherichia coli*. J.Infect.Dis. 151:775-782 (1985).

Kawahara, M., Matsuo, K., Nakasone, T., Hiroi, T., Kiyono, H., Matsumoto, S., Yamada, T., Yamamoto, N., and Honda, M. Combined intrarectal/intradermal inoculation of recombinant *Mycobacterium bovis* bacillus Calmette-Guerin (BCG) induces enhanced immune responses against the inserted HIV-1 V3 antigen. Vaccine 21:158-166 (2002).

Kenny, B., Devinney, R., Stein, M., Reinscheid, D. J., Frey, E. A., and Finlay, B. B. Enteropathogenic *E. coli* (EPEC) transfers its receptor for intimate adherence into mammalian cells. Cell 91:511-520 (1997).

Ketley JM, Kaper JB, Herrington DA, Losonsky G, Levine MM. Diminished immunogenicity of a recombination-deficient derivative of *Vibrio cholerae* vaccine strain CVD103. Infect Immun., 58:1481-84 (1990).

Killham K, Jones D. Survival of *Escherichia coli* 0157 in Environmental Matrices. Absrt. P-24, 5th International Symposium on 'Shiga Toxin (Verocytotoxin)-Producing *Escherichia coli* Infections', Scotland (2003).

Klapproth, J. M., I. C. Scaletsky, B.P. McNamara, L.C. Lai, C. Malstrom, S. P. James, and M. S. Donnenberg. A large loxin from lathogenic *Escherichia coli* strains that inhibits lymphocyte activation. Infect. Immun. 68:2148-55 (2000).

Klauser T, Kramer J, Otzelberger K, Pohlner J, Meyer TF. Characterization of the *Neisseria* IgA beta-core, the essential unit for outer membrane targeting and extracellular protein secretion. J Mol Biol, 234:579-93 (1993).

Kleanthous, H., Myers, G. A., Georgakopoulos, K. M., Tibbitts, T. J., Ingrassia, J. W., Gray, H. L., Ding, R., Zhang, Z. Z., Lei, W., Nichols, R., Lee, C. K, Ermak, T. H., and Monath, T. P. Rectal and intranasal immunizations with recombinant urease induce distinct local and serum immune responses in mice and protect against *Helicobacter pylori* infection. Infecti.Immun. 66:2879-2886 (1998).

Konieczny MP, Suhr M, Noll A, Autenrieth IB, Alexander SM. Cell surface presentation of recombinant (poly-)peptides including functional T-cell epitopes by the AIDA autotransporter system. FEMS Immunol Med Microbiol, 27:321-32 (2000).

Lattemann CT, Maurer J, Gerland E, Meyer TF. Autodisplay: functional display of active beta-lactamase on the surface of *Escherichia coli* by the AIDA-I autotransporter. J Bacteriol., 182:3726-33 (2000).

Levine MM, Kaper JB, Herrington D, Ketley J, Losonsky G, Tacket CO, et al. Safety, immunogenicity, and efficacy of recombinant live oral *Cholera* vaccines, CVD 103 and CVD 103-HgR. Lancet, 2:467-70 (1988).

Levine et al., J. Clin. Invest., 79:888-902 (1987).

Low JC, Besser TE Mahajan A Gunn GJ Pearce MC McKendrick IJ Smith DGE and Gaily DL. Lymphoid Follicle-Dense Mucosa at the Terminal Rectum is the Principal Site of Colonization of Enterohaemorrhagic *Escherichia call* O157:H7 in the Bovine Host. Absrt. P-129, 5th International Symposium on 'Shiga Toxin (Verocytotoxin)-Producing *Escherichia coil* Infections', Scotland (2003).

Ludwig, K., M. A. Karmali, C. R. Smith, and M. Petric. Cross-protection against challenge by intravenous *Escherichia coil* verocytotoxin 1 (VT1) in rabbits immunized with VT2 toxoid Can. J. Microbiol. 48:99-103 (2002).

Luo, Y., E. A. Frey, R. A. P fuetzner, A. L. Creagh, D. G. Knoechel, C. A. Haynes, B. B. Finlay, and N. C. Strynadka.. Crystal structure of enteropathogenic *Escherichia coli* intimin-receptor complex. Nature 405:1073-1077 (2000).

Mackman N, Baker K, Gray L, Haigh R, Nicaud JM, Holland IB. Release of a chimeric protein into the medium from *Escherichia coil* using the C-terminal secretion signal of a hemolysin. EMBO J, 6:2835-41 (1987).

\* cited by examiner

Fig. 3A
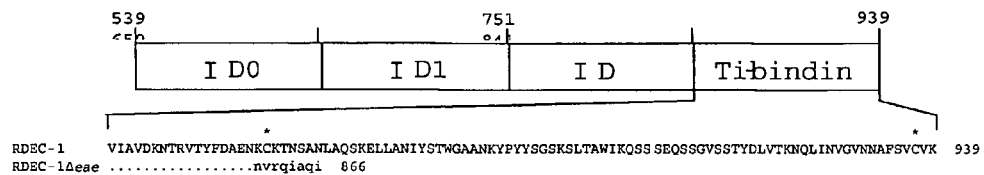
RDEC-1    VIAVDKNTRVTYFDAENKCKTNSANLAQSKELLANIYSTWGAANKYPYYSGSKSLTAWIKQSS SEQSSGVSSTYDLVTKNQLINVGVNNAFSVCVK 939
RDEC-1Δeae  ................nvrqiaqi  866
Nucleotide alignment:
RDEC-1:    2562 AAC AAA TGT AAG ACA AAT AGC GCA AAT TTA G 2593
RDEC-1Δeae: 2562 AAC  AA TGT AAG ACA AAT AGC GCA AAT TTA G 2592
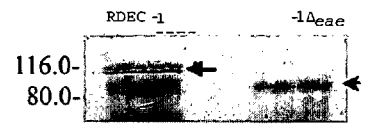
Fig. 3B                    Fig. 3C
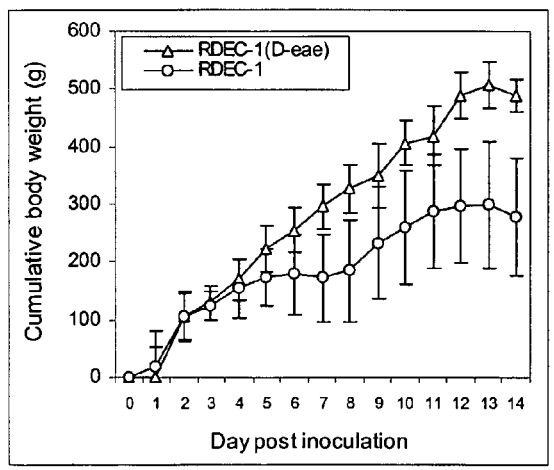  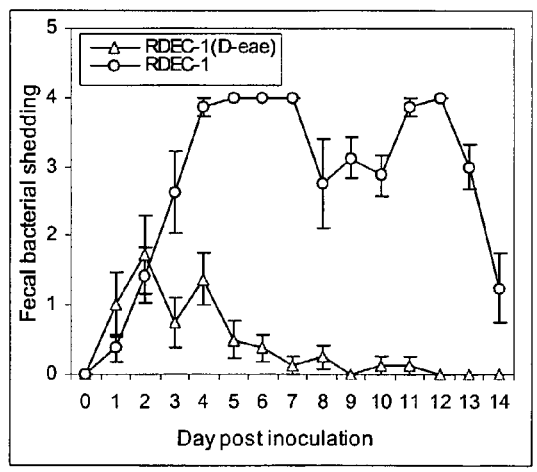
Fig. 4A                    Fig. 4B

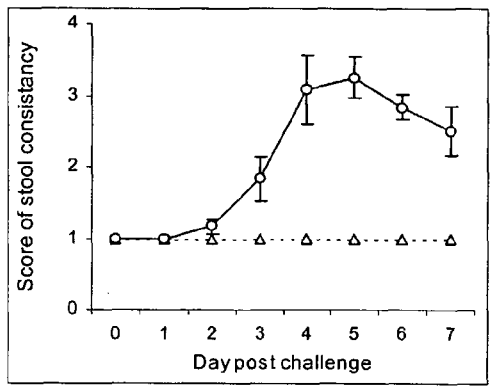
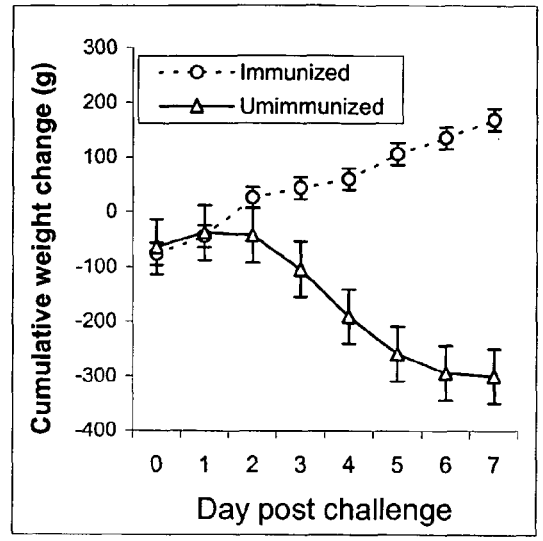
Fig. 5A  Fig. 5B
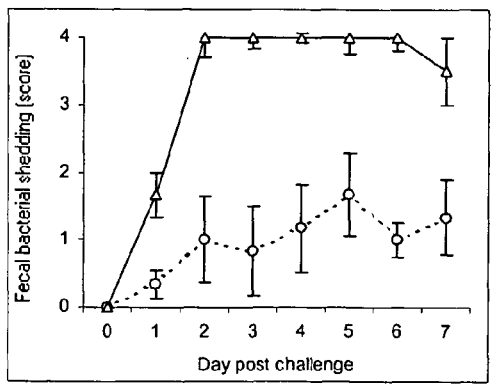
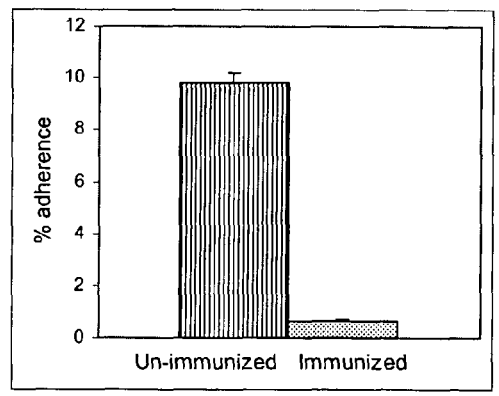
Fig. 5C  Fig. 5D

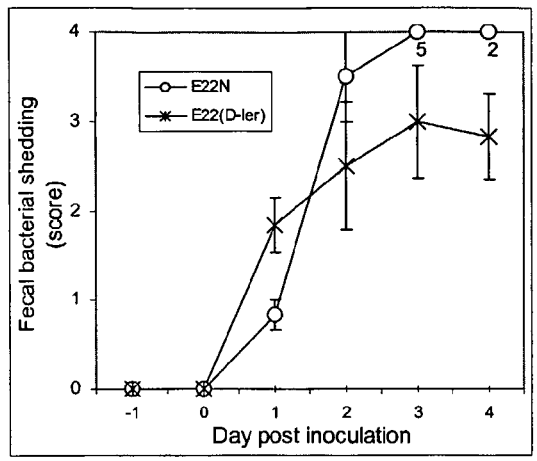 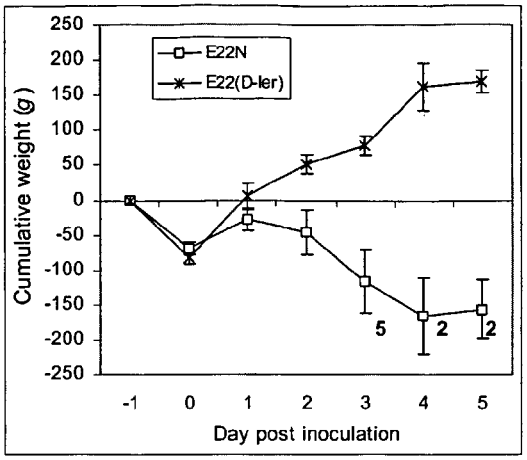
Fig. 11A Fig. 11B
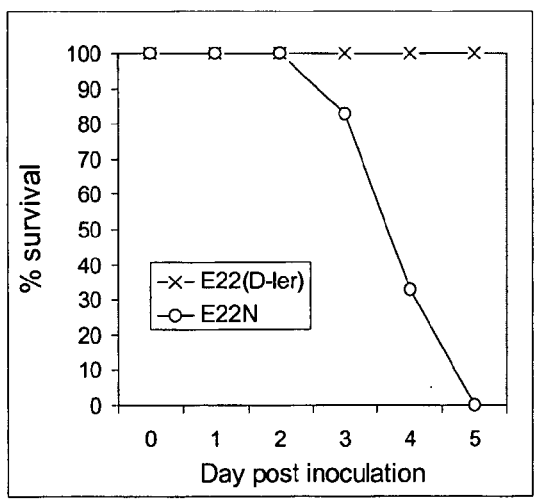 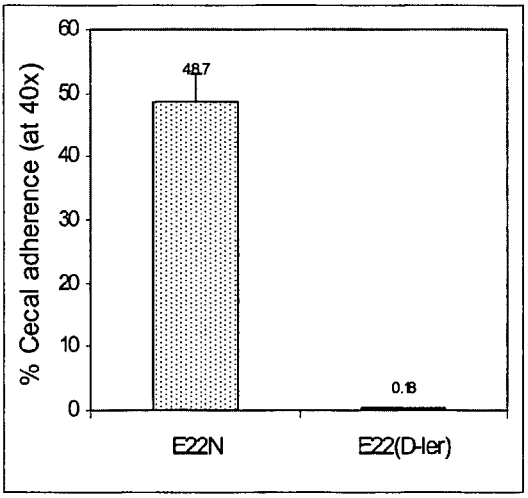
Fig. 11C Fig. 11D

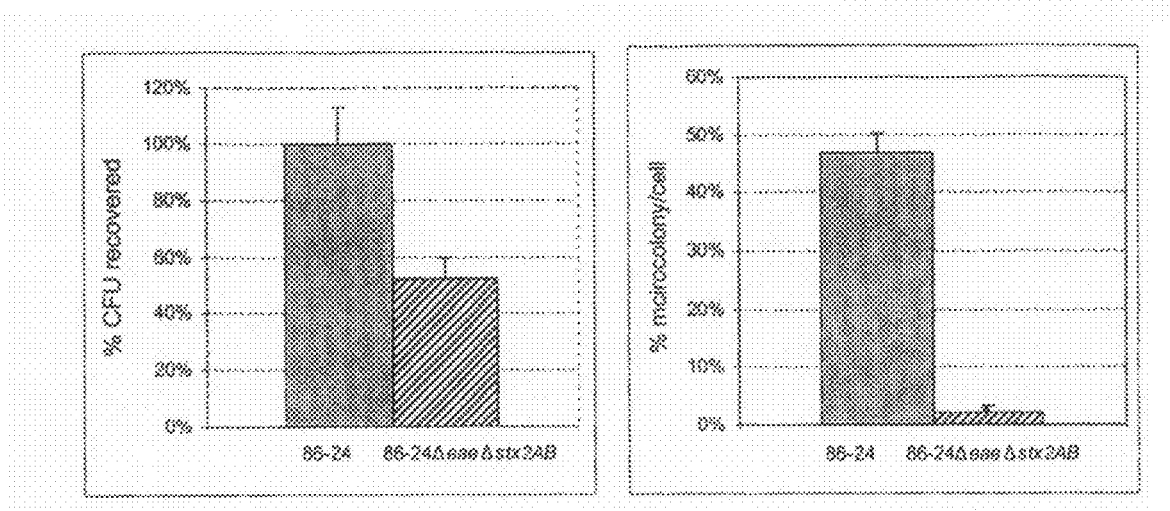
Fig. 17A  Fig. 17B
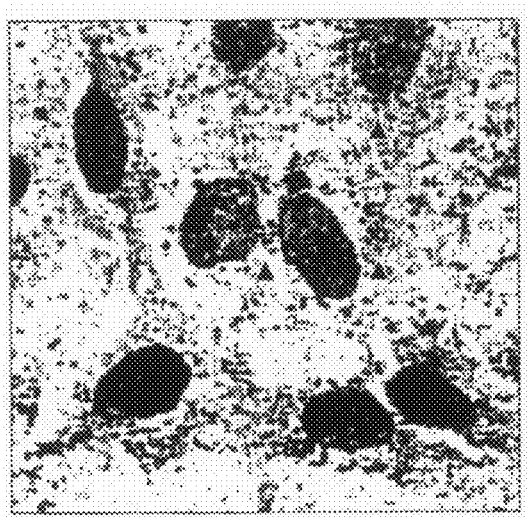 
Fig. 18A  Fig. 18B

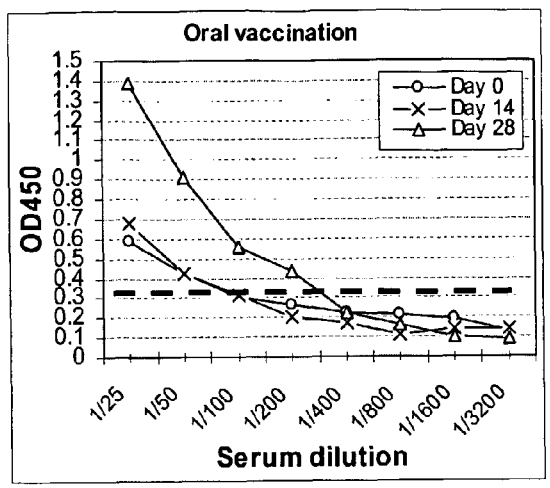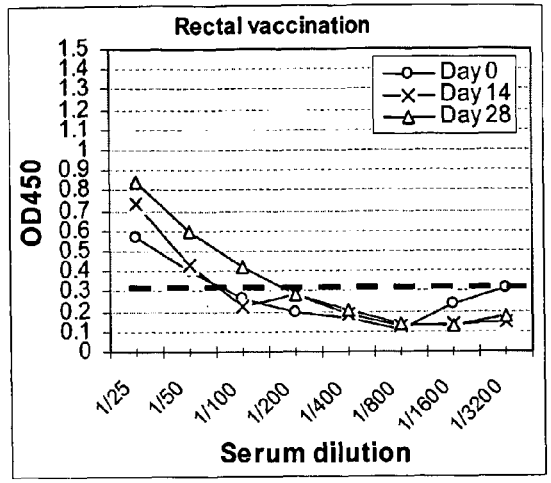
Fig. 21A          Fig. 21B
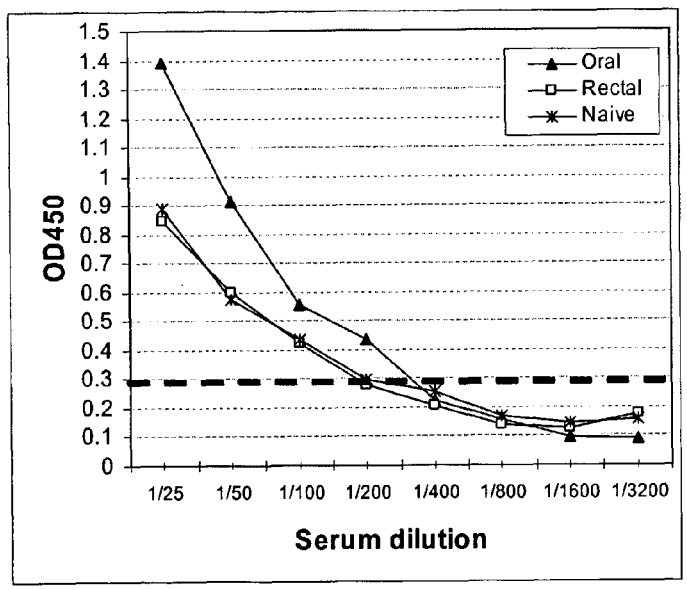
Fig. 22

LIVE ATTENUATED BACTERIAL VACCINE TO REDUCE OR INHIBIT CARRIAGE AND SHEDDING OF ENTEROHEMORRHAGIC *ESCHERICHIA COLI* IN CATTLE

GOVERNMENT LICENSE RIGHTS

The experiments performed in this application were supported in part by the National Institutes of Health, Grant No. NIDDK 1R01DK59012, and USDA, Grant No. CSREES 20053520115345. The U.S. Government has a paid-up license in this invention and the right in limited circumstances to require the patent owner to license others on reasonable terms as provided for by the terms of the above grants.

CROSS-REFERENCE TO RELATED APPLICATIONS

The present application claims the benefit of priority under 35 U.S.C. §119 (e) from provisional U.S. application No. 60/621,872, filed Oct. 26, 2004, the entire content of which is herein incorporated by reference.

BACKGROUND OF THE INVENTION

1. Field of the Invention

The present invention relates to live attenuated bacteria for use in vaccines.

2. Description of the Related Art

Shiga toxin-producing strains of *Escherichia coli* (STEC), also known as enterohemorrhagic *Escherichia coli* (EHEC) are important foodborne pathogens associated with foodborne epidemics of bloody diarrhea and hemorrhagic colitis (HC) (Nataro et al., 1998). While HC is often self-limiting, STEC infection can lead to more severe complications including central nervous system (CNS) disturbance and fatal hemolytic uremic syndrome (HUS) (Karmali et al., 1985). HUS is characterized by microangiopathic hemolytic anemia, thrombocytopenia, and acute renal failure and is especially life-threatening for the young and elderly (Carter et al., 1987 and Nataro et al., 1998). Human disease-associated STEC strains are referred as enterohemorrhagic *E. coli* (EHEC). According to the Center for Disease Control (CDC), there are about 73,000 cases of STEC infections in the U.S. each year. HUS occurs in 5-10% of these cases and leads to as many as 250 deaths (Boyce et al., 1995; Nataro et al., 1998). In the U.S., EHEC are most often serotype O157:H7, but strains in other serogroups including 026, 0111 also cause disease. Although STEC strains are generally susceptible to a variety of antibiotics, there are retrospective studies showing that the use of antibiotics negatively alters the outcome of STEC infections leading to increased incidence of HUS (Nataro et al., 1998). This is likely because lysis of bacteria by some antibiotics leads to increased release of toxin, as well as to increased toxin synthesis during the induction of lysogenic toxin-producing bacteriophage. Second, antibiotic therapy may alter the balance of intestinal flora thereby increasing the systemic absorption of released toxin (Nataro et al., 1998). Infections caused by STEC have became a public health concern since outbreaks of the disease were reported following ingestion of undercooked ground beef in hamburgers distributed by national fast food chains. Outbreaks of infection with STEC are likely to continue because of the capacity for wide distribution of the infecting organism provided by an efficient food distribution system. Currently, there are no proven vaccines or therapeutic agents for infections caused by STEC (EHEC).

Cattle are most frequently identified as the primary source of EHEC infection. EHEC thrives in the ruminant gastrointestinal tract, farm water troughs, raw manure, and other contaminated environmental surfaces (Hovde et al., 1999). The bacteria can survive for more than 2 to 5 months in water containing rumen content (Doyle, 2003 and Killham et al., 2003). The EHEC organisms may be shed at levels up to $10^6$ cfu per gram of feces for several weeks following infection (Naylor et al., 2003 and Omisakin et al., 2003). Although natural symptomatic STEC infections have been reported in young calves (Janke et al., 1989; Person et al., 1989; Pospischil et al., 1987; Schoonderwoerd et al., 1988; and Wray et al., 1989), colonization in adult cattle by EHEC causes no clinical disease. EHEC isolates from cattle produce Shiga toxin (both Stx-1 and/or Stx-2), however, the mechanisms for resistance of adult cattle to STEC disease, despite documented intestinal carriage, is still unknown (Pospischil et al., 1987; and Stordeur et al., 2000). It is important to recognize that the rectum and cecum are principal sites of STEC 0157:H7 colonization during the carrier-shedder state in cattle (Dean-Nystrom, 2003).

The broad outline of the pathogenic mechanisms of STEC infections in humans, due to strain 0157:H7 and other STEC, are well known. After ingestion of contaminated food or water, STEC colonize the intestine (primarily the large bowel), utilizing a mechanism of intimate adherence to intestinal epithelial cells, and elaborate a potent toxin, Shiga toxin (Stx), which is the major virulence factor of this organism (Nataro et al., 1998). Locally produced Stx is then absorbed into the circulation and targets microvascular endothelial cells containing specific receptors for Stx. Low levels of Stx reaching the circulation are able to induce profound vascular lesions in target organs including bowel, central nervous system and kidney (Gyles, 1994).

The hallmark of pathogenicity of EHEC is the production of Stx implicated in the development of HUS (Griffin et al., 1991; Kaper, 1998; Noel et al., 1997; and O'Brien et al., 1992). Stx(s) produced by EHEC belong to a family of bacterial cytotoxins structurally related to those produced by the dysentery *bacillus Shigella dysenteriae* (Tesh et al., 1991; and O'Brien et al., 1992). Both Stx-1 and Stx-2 are in the class known as AB toxins composed of one A subunit and five identical receptor-binding B subunits (Jackson, 1990,—and Jackson et al., 1990). The B subunit binds to a receptor molecule on the host cell surface (Jackson, 1990; Jackson et al., 1990; and Mobassaleh et al., 1988). The A subunits of both toxins are highly selective N-glycosidases that depurinate a specific adenine residue on the eukaryotic 60S ribosomal subunit thus blocking protein synthesis and leading to the death of the cell (Hovde et al., 1988; and Jackson et al., 1990). Shiga toxins can modulate cytokine secretion and function. For instance, Shiga toxins induce expression and synthesis of cytokines in Caco-2 cells, and their N-glycosidase activity is essential for the induction because proinflammatory cytokine mRNAs, especially IL-8, were induced by Stx1 and Stx2 but not by a non-toxic mutant of Stx1 which lacks N-glycosidase activity (Yamasaki et al., 1999). Microarray analysis demonstrated upregulation of genes belonging to chemokines and cytokines and other genes encoding cell adhesion molecules and transcription factors that are involved in immune response or apoptosis (Matussek et al., 2003).

Attaching and effacing *Escherichia coli* (AEEC) represent a group of enteric pathogens of humans and animals, including human hEPEC, a major cause of infant diarrhea; EHEC, an important food-borne pathogen; strains causing diarrhea in animals such as rabbit (rEPEC), pig and dog EPEC; and *Citrobacter rodentium* in mice (Nataro et al., 1998; An et al., 1997; Cantey et al., 1977; and Zhu et al., 1994). Central to the pathogenesis of AEEC infection is the formation of attaching/effacing (A/E) lesions characterized by intimate bacterial attachment to intestinal epithelial cells and effacement of microvilli with disruption of host cell cytoskeleton (Nataro et al., 1998). The genes essential for the A/E phenotype are encoded on the locus of enterocyte effacement (LEE) pathogenicity island (PAI), the complete nucleotide sequence of which has been obtained from hEPEC O127:H6 (strain E2348/69) (Elliott et al., 1998), EHEC O157:H7 (strain EDL933) (Perna et al., 1998), rEPEC strain RDEC-I (015:H-) (Zhu et al., 2001), and *C. rodentium* associated with colonic hyperplasia in mice (Deng et al., 2001).

LEEs of EPEC, EHEC, rEPEC, and *C. rodentium* share a 34-kb conserved region containing 40 (RDEC-I) or 41 (hEPEC, EHEC or *C. rodentium*) open reading frames (ORF) organized into five major polycistronic operons: LEE1, LEE2, LEE3, LEE5 and LEE4, and several minor operons and monocistronic genes (Elliott et al., 1998). The conserved 34-kb core region of LEE PAIs of rEPEC, hEPEC, EHEC, and *C. rodentium* exhibit nearly identical genetic organization and high homology of LEE-encoded genes (FIG. 1; Elliott et al., 1998; Perna et al., 1998; Zhu et al., 2001; and Deng et al., 2001). The LEE encodes a global regulator Ler (LEE encoded regulator), a type III secretion system (TTSS) (LEE1, LEE2, LEE3), a bacterial adhesin named intimin, a translocated intimin receptor Tir and CesT chaperone for Tir (LEE 5), and several secreted effector proteins (LEE4) including Esp D, B, and F which are delivered into host cells via the TTSS (Elliott et al., 1998; Kaper et al., 2004 and Kenny et al., 1997). TTSSs are critical for the virulence of A/E organisms. While TTSS apparatus deliver LEE-encoded effector molecules, such as Tir, Map, EspF EspG, and EspH, the TTSSs also contribute to delivering virulence factors encoded outside the LEE, such as Cif, and EspF(u) (McNamara et al., 2001; and Marches et al., 2003).

Ler is encoded as the first open reading frame (ORF) in LEE1. It is highly conserved (95-98% amino acid identity) among hEPEC, EHEC and rEPEC 015:H-strain RDEC-I (Elliott et al., 1998; Perna et al., 1998; and Zhu et al., 2001). The deduced amino acid (AA) sequences of Ler from hEPEC share substantial similarities (24% identity and 44% similarity) with H—NS, the histone-like non-structural protein) of *Salmonella* mainly in the carboxyl terminus (Elliott et al., 2000). It has been shown that Ler plays a central role in the regulation of LEE-encoded gene expression (FIG. 2) and, in EPEC, that Ler positively regulates the LEE operons by acting as an antirepressor protein that overcomes the H—NS-mediated silencing of the LEE2/LEE3, LEE5 and LEE4 (Bustamante et al., 2001; Haack et al., 2003; and Sanchez-Sanmartin et al., 2001) Ler also activates the expression of the genes outside the LEE, such as espC encoded on a second PAI of EPEC (Elliott et al., 2000).

rEPEC constitutes a subset of the AEEC pathotype and strains of different serotypes have been shown to be causative agents of rabbit enteritis (Camguilhem et al., 1989; and Peeters et al., 1988). rEPEC induce A/E lesions in a manner similar to hEPEC and EHEC (Cantey et al., 1977). The extensive phenotypic and genotypic homologies among human and animal A/E strains suggest a common evolutionary origin and perhaps common regulatory mechanisms for LEE-encoded gene expression. A previous study demonstrated in hEPEC that the Ler is essential for in vitro pathogenic effects suggesting that a deletion mutation in the ler gene might attenuate the in vivo virulence of rEPEC (Mellies et al., 1999; and Sperandio et al., 2000).

Bacterial intimate adherence to host epithelial cells is mediated by binding of intimin to the translocated intimin receptor (Tir), which is delivered by A/E organisms to eukaryotic cells (Frankel et al., 1996a, 1996b and 1998; Hartland et al., 1999; Hicks et al., 1998; and Kenny et al., 1997). Intimin is an outer membrane protein (OMP) adhesin that shares homology with the invasin that promotes eukaryotic cell invasion by *Yersinia* (Jerse et al., 1990). Currently, nearly a dozen genetically and serologically distinct intimin subtypes are reported among A/E organism (Adu-Bobie et al., 1998; Oswald et al., 2000; Ramachandran et al., 2003; and Zhang et al., 2002). All currently known intimin alleles demonstrate more homology in their amino (N)-terminal regions than in their carboxy (c)-terminal regions. Intimins of A/E *E. coli* (AEEC) including human EPEC O127-.H6 (Intimin-α), EHEC O157:H7 (Intimin-γ), or rEPEC 015-.H-(Intimin-β) show greater than 94% amino acid (aa) identity over the N-terminal two thirds of the molecule while showing only 55% homology over the remaining one third portion at the C-terminus (Zhu et al., 2001). The crystal structure of the C-terminal EPEC intimin fragment (residues 658-939) revealed three adjacent domains: the immunoglobulin-like (Ig) D1 (residues 658-751) and D2 (residues 752-841) and the C-type lectin-like D3 (residues 842-929) (Frankel et al., 1995; and Luo et al., 2000). The immunodominant regions have been demonstrated to be in the domains D1 and D2, as shown by reaction with intimin-specific antiserum (Adu-Bobie et al., 1998). Binding of intimin and Tir is mediated primarily by interactions between the lectin-like D3 domain of intimin and the Tir intimin-binding domain (Luo et al., 2000). Within the Tir-binding region of intimin two conserved cysteine residues (aa 860 and 937 of EPEC intimin) are involved in the formation of a disulfide loop essential for intimin function (Frankel et al., 1995; Hicks et al., 1998; and Luo et al., 2000). This disulfide loop is conserved in *Yersinia* invasin and all the intimin molecules (Eliott et al., 1998; Ramachandran et al., 2003; and Zhu et al., 2001). Recent studies have shown that other accessory proteins promote bacterial adherence to intestinal epithelial cells, including the Efa1 from EHEC 0111 (Nicholls et al., 2000) and the Efa1 homologue LifA from EPEC 0126:H7 (Klapproth et al., 2000), the flegellin of EHEC, and some novel fimbriae (Torres et al., 2003). However, these proteins are not directly involved in the formation of A/E lesions.

Intimin is critical for intimate bacterial adherence. Attenuation of virulence by deletion of intimin has been demonstrated for human EPEC (0127:H6) (Donnenberg et al., 1993a), human EHEC (O157:H7) (Donnenberg et al., 1993b), rEPEC (O103:H2) (Marches et al., 2000), and *C. rodentium* (Deng et al., 2004).

The role of intimin in in vivo virulence has been tested through isogeneic mutants deficient in expression of functional intimin. Donnenberg and Kaper created an internal 1848-bp deletion in EPEC eae gene and tested its pathogenicity in humans (Donnenberg et al., 1991). While all of the human volunteers received WT EPEC developed diarrhea, the isogeneic eae mutant caused diarrhea in 4 of 11 individuals (Donnenberg et al., 1993a). In a separate study, the isogeneic eae mutant generated by replacing the internal 1.1-kb eae DNA with a 2.9-kb DNA fragment containing a Tet marker of human EHEC 86-24 (0157:H7) was unable to colonize in experimentally inoculated piglets (Donnenberg et al., 1993b). In REPEC O103:H2, an insertion of aphT encoding Kan resistance in the eae gene (between 993 nt and 994 nt) disrupted the expression of intimin and abolished bacterial virulence when tested by experimental inoculation of its natural rabbit host (Marches et al., 2000). Anti-intimin immune responses can modulate the outcome of A/E organism infection. In another study conducted in piglets, passive immunization, achieved by allowing neonatal piglets to suck colostrums from intimin-vaccinated dams for up to 8 h before inoculating with EHEC 0157:H7, protected animals from STEC 0157:H7 colonization and intestinal damage (Dean-Nystrom et al., 2002). Using mutant E. coli heat-labile enterotoxin (LT) lacking the nick site in the A subunit as an adjuvant, intranasally administered 0157:H7 intimin induced an elevation of IgA-specific antibody in the nasal secretion and saliva of calves as well as an elevation of IgG1-specific antibody level against the intimin in the sera and colostrums of cows (Yokomizo et al., 2002). In yet another study, EHEC 0157:H7 intimin C-terminal domain was expressed in transgenic tobacco plant cells and mice immunized with the plants generated an intimin-specific mucosal immune response and exhibited a reduced duration of EHEC 0157:H7 fecal shedding (Judge et al., 2004). Interestingly, vaccination of mice with Int280α induced both type-specific protection to intimin-c organisms and to heterologous intimin types indicating that a highly conserved domain of intimin (Int388-667) including part of C-terminal fragment D1 domain may have potential to induce protection against infections by A/E organism expressing different intimin types (Ghaem-Maghami et al, 2001).

More than 50 serotypes of STEC have been isolated from stool samples of patients with hemorrhagic colitis or HUS. STEC 0157:H7 is the predominant serotype reported as the causative agent world-wide (Nataro et al., 1998). Analysis of HUS samples collected from 1987 to 1991 in the United States indicated that STEC could be implicated in 72% of cases of HUS, and STEC serotype 0157 may be implicated in 80% cases studied (Banatvala et al., 2001). However, infections due to non-0157 STEC are now increasingly recognized (Nataro et al., 1998; and Tarr et al., 1996 and 2002). Of these, STEC 026 and STEC 0111 have been isolated most frequently. In Boston and Virginia, approximately half of all Stx-producing E. coli isolates from patients were of non-0157:H7 serotypes (Park et al., 1996). STEC serogroup 026 and 0111 have been increasingly associated with outbreaks in Europe, Japan, Australia, India, where they account for the majority of HUS cases (Ojeda et al., 1995,—Pierard et al., 1990; and Robins-browne et al., 1998). The prevalence of 0157, 026, and 0111 in humans is in accordance with the findings that these serogroups were most common in fecal samples from animals (Blanco et al., 2004a and 2004b; Borie et al., 1997; and Rey et al., 2003).

Vaccines for animals are aimed at reduction of EHEC secretion in their natural host. A clinical trial of a parenteral STEC vaccine has recently been conducted by the Canadian investigators (Potter et al., 2004). The vaccine formulation containing secreted protein preparations of STEC strain 0157:H7, together with aluminum adjuvant, VSA3 was delivered subcutaneously in the necks of seronegative cattle (Potter et al., 2004). Vaccinated cattle were primed and showed an increase in serum IgG antibody titers. Vaccination was reported to reduce the prevalence of STEC 0157:H7 from 21.3% to 8.8% in feedlot cattle at the day of marketing (Potter et al., 2004). Thus, although an apparent effect was seen, substantial numbers of vaccinated animals still shed STEC in the feces.

In a non-vaccine study, the combinations of several strains of probiotics were shown to inhibit the growth of EHEC 0157 in vitro and reduce the fecal shedding of EHEC 0157:H7 (Doyle, et al, 2003). The fecal shedding and pathogenicity of STEC O26:H11, 0111:NM, 0157:H7 in weaned calves (8 to 10 weeks of age) were compared with and without treatment using a three-strain mixture (Hicks et al., 1998 and Tkalcic et al., 2003). The probiotic E. coli substantially reduced or eliminated fecal shedding of 0157:H7 and 0111:NM. However, STEC were still recovered from one third of calves receiving the probiotic treatment, and the probiotic E. coli did not reduce fecal shedding or gastrointestinal persistence of 026:HIl (Hicks et al., 1998 and Tkalcic et al., 2003). Interestingly, when probiotics were used in calves of less that 1 week of age, reduced fecal shedding of 0111:NM and O26:H11 but not STEC 0157 was observed in most calves (Zhao et al., 2003).

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a live, attenuated enterohemorrhagic Escherichia coli (EHEC) of serogroup 0157, 026 or 0111 in which the Shiga toxin (Stx) coding sequences are deleted to abolish Shiga toxin production and one or more of the nucleotide sequences coding for the bacterial adhesin protein intimin (eae), the locus of enterocyte effacement encoded regulator (ler), and the translocated intimin receptor (tir) are mutated to inactivate the activity of the encoded protein (s).

The present invention also provides a vaccine for reducing or inhibiting carriage and shedding of enterohemorrhagic E. coli in cattle which contains an immunogenically effective amount of the live, attenuated enterohemorrhagic E. coli.

Another aspect of the present invention is directed to a method for reducing or inhibiting carriage and shedding of enterohemorrhagic Escherichia coli in cattle by immunizing cattle with the vaccine of the present invention.

A further aspect of the present invention is directed to a method for producing the isolated live, attenuated enterohemorrhagic E. coli of the present invention.

BRIEF DESCRIPTION OF THE DRAWINGS

FIG. 3A is a schematic representation of RDEC-I intimin C-terminal fragment (539-939aa) showing Ig-like (Ig) and Tir-binding domains. Numbers represent aa position of intimin deduced from RDEC-I LEE. The residues of intimin Tir-binding domain (residues 842-939 of SEQ ID NO: 5) are shown. Asterisks indicate two conserved cysteine residues (residues 860 and 937) involved in the formation of a disulfide loop essential for intimin function. The RDEC-l Δeae C-terminal sequence (SEQ ID NO: 6) is also shown, where residues identical with the RDEC-I C-terminus are shown by dots. FIG. 3B is a DNA alignment of a partial sequence of the RDEC-leae gene (SEQ ID NO: 25) and a partial sequence of the RDEC-l Δeae gene (SEQ ID NO: 26) showing a single base deletion (arrow) which introduced a stop codon (underlined) 24-bps immediately after deletion. FIG. 3C is a comparison of OMP profiles on a gel showing native intimin (denoted by arrow) by RDEC-I or truncated intimin (arrow head) by RDEC-l Δeae. Molecular markers are indicated in kDa.

FIGS. 4A and 4B are graphs showing comparisons of cumulative weight change (FIG. 4A) and fecal bacterial shedding (FIG. 4B) between rabbits inoculated with WT RDEC-I or its derivative eae mutant. Averages were derived from six rabbits in each group. Bars designate standard errors.

FIGS. 5A-5D are graphs showing comparisons of fecal bacterial shedding (FIG. 5c), cumulative weight change (FIG. 5B) stool consistency (FIG. 5A), and percent of mucosal surface (cecum) with adherent bacteria (FIG. 5D) between RDEC-l Δeae-immunized (circles) and unimmunized groups (triangles) following challenge with RDEC-H19A. Bars designate standard errors.

FIG. 9A shows the nucleotide alignments of ler and upstream regions of hEPEC (0127:H6, strain E2348/69, GenBank accession no. AF022236; SEQ ID NO: 14), EHEC (O157:H7, strain Eα933, GenBank accession no. AF071034; SEQ ID NO:16), C. rodentium (strain DBSlOO, GenBank accession no. AF311901; SEQ ID NO:18), rEPEC RDEC-I (GenBank accession no. AF200363; SEQ ID NO:20), and rEPEC O103:H2, strain E22; SEQ ID NO:22) showing the ler coding sequence (bold). The 300-bp deletion fragment generated in the ler of strain E22 is underlined. FIG. 9B shows the alignment of the predicted amino acid sequences of Ler proteins of EPEC (SEQ ID NO:15), EHEC (SEQ ID NO:17), C. rodentium (SEQ ID NO:19), RDEC-I (SEQ ID NO:21), E22 (SEQ ID NO: 23) and E22Δler (SEQ ID NO: 24). Identical sequences are indicated by dots. Gaps introduced for alignment are represented by dashes. Numbers on the right side of the sequence indicate the position in the relevant LEE PAI (A) or deduced Ler (B).

FIGS. 11A-11D are graphs of a pathogenicity study comparisons of fecal bacterial shedding (Fig. HA), cumulative weight change (Fig. HB), percentage survival (Fig. HC), and percentage of mucosal surface (cecum) with adherent bacteria (Fig. HD) between groups of rabbits inoculated with WT rEPEC strain E22 ($6 \times 10^5$ CFU) or its derivative ler mutant ($1 \times 10^8$ CFU). Averages were derived from six rabbits in each group at the start of experiment. By the end of the experiment, averages in the WT E22 group were derived from the number of survivors (survivor numbers shown next to average data points in Fig. H A and HB). Bars designate standard errors.

Figure 12A:
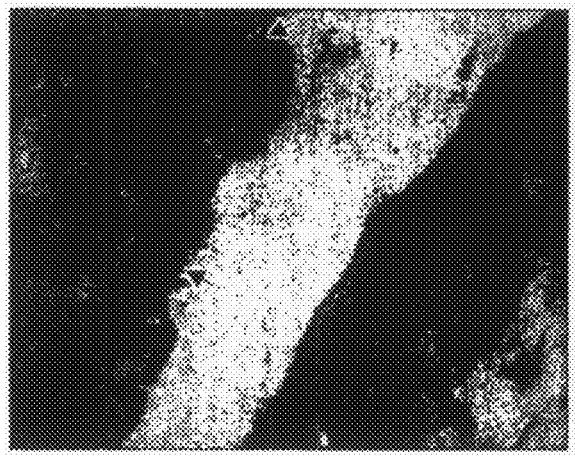
FIGS. 12A and 12B are micrographs (Giemsa stain, magnification 400×) of cecal tissues from rabbits infected for five days with WT rEPEC (FIG. 12A) or E22. Δler (FIG. 12B).
Figure 12B:
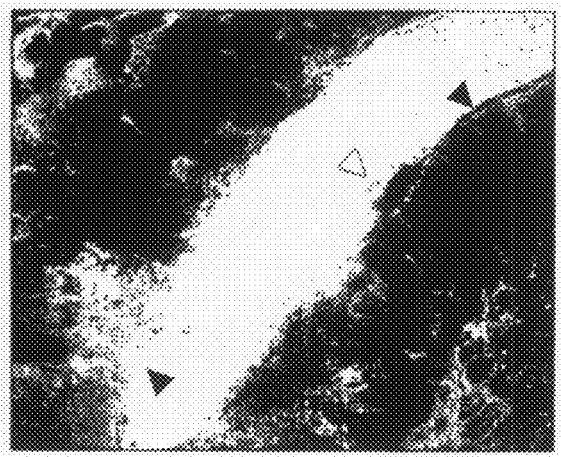

Intimate mucosal attachment of bacteria with effacement of the apical brush border (arrows) representing typical A/E lesions in shown in FIG. 12A. This process involves 40% of the mucosal surface in this micrograph. Intact intestinal mucosa and normal brush borders (arrow heads) are shown in FIG. 12B. Note the normal appearance of the brush border. Although scattered adherence of organisms was seen (white arrow head), bacterial attachment was non-intimate and brush borders appeared normal.

FIG. 13A-13D are graphs of a protection study showing cumulative weight gain (FIG. 13A), fecal bacterial shedding (FIG. 13B), percent survival (FIG. 13C), and fold increase of serum IgG against whole bacterial cells (FIG. 13D) in rabbits previously-immunized with a single orogastric dose of E22Δ2er and challenged with the WT parent E22 (day of challenge shown as day 0). Bars represent the standard errors.

Figure 14:
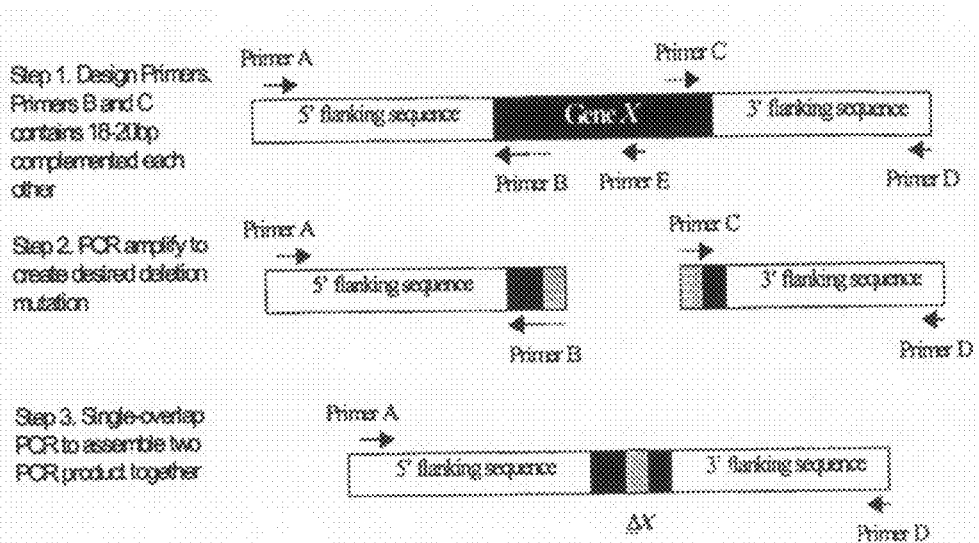

FIG. 14 is a schematic illustration of single-overlap extension PCR (SOE PCR).

Figure 15:
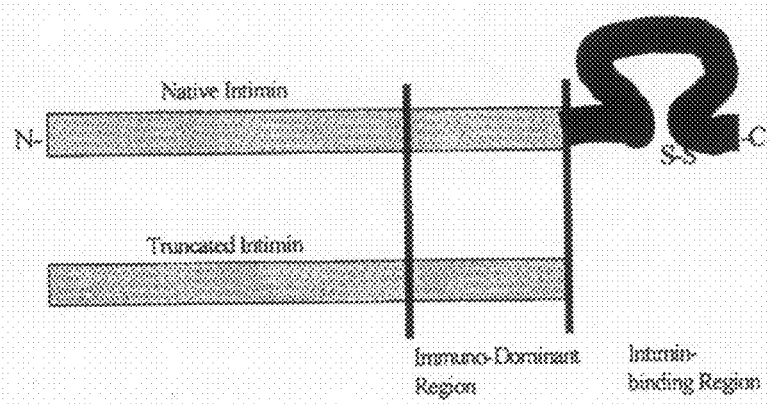

FIG. 15 is a schematic representation of native intimin and truncated intimin.

Figure 16:
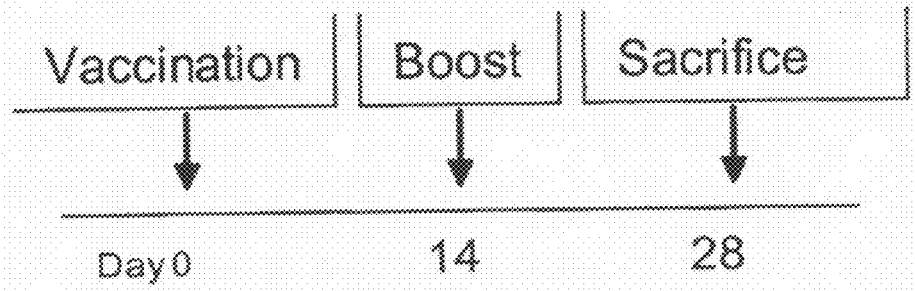

FIG. 16 is a timeline of the vaccination protocol.

FIGS. 17A and 17B are graphs of adherence to HeLa cells showing recovered percentage of CFU (FIG. 17A) and adherence pattern (FIG. 17B) following 6 h incubation. Bars represent standard error.

FIGS. 18A and 18B are micrographs showing microcolonies by the WT EHEC 0157:H7 strain 86-24 (FIG. 18A) and its derivative mutant (FIG. 18B). Microcolonies were seen for the WT EHEC (arrow heads) but rarely seen for the isogenic mutant.

Figure 19:
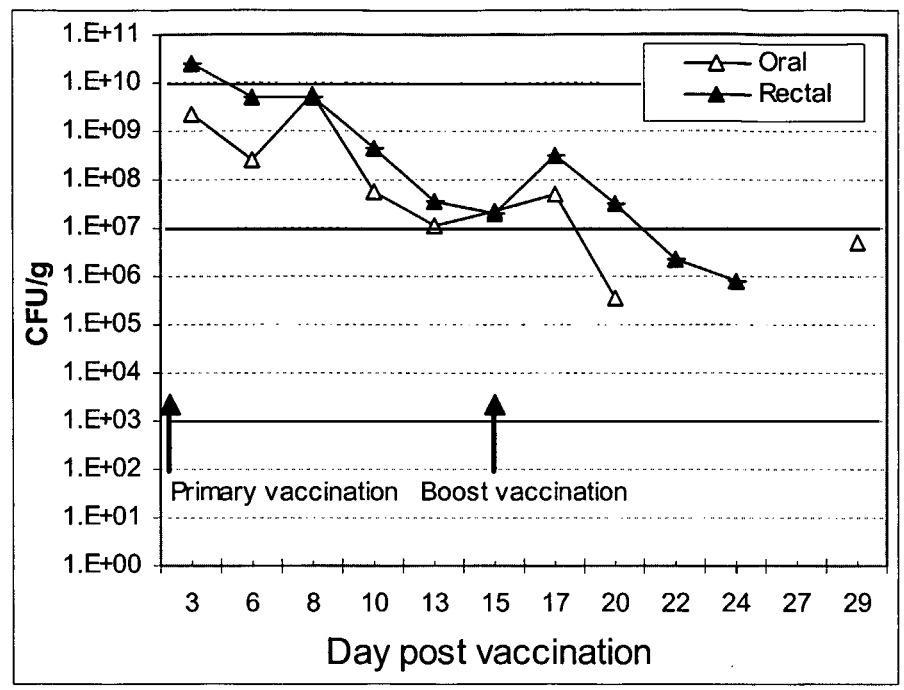

FIG. 19 is a graph showing fecal bacterial shedding following primary and booster vaccination with 86-24 ΔeaeΔstx2AB by oral or rectal route.

Figure 20:
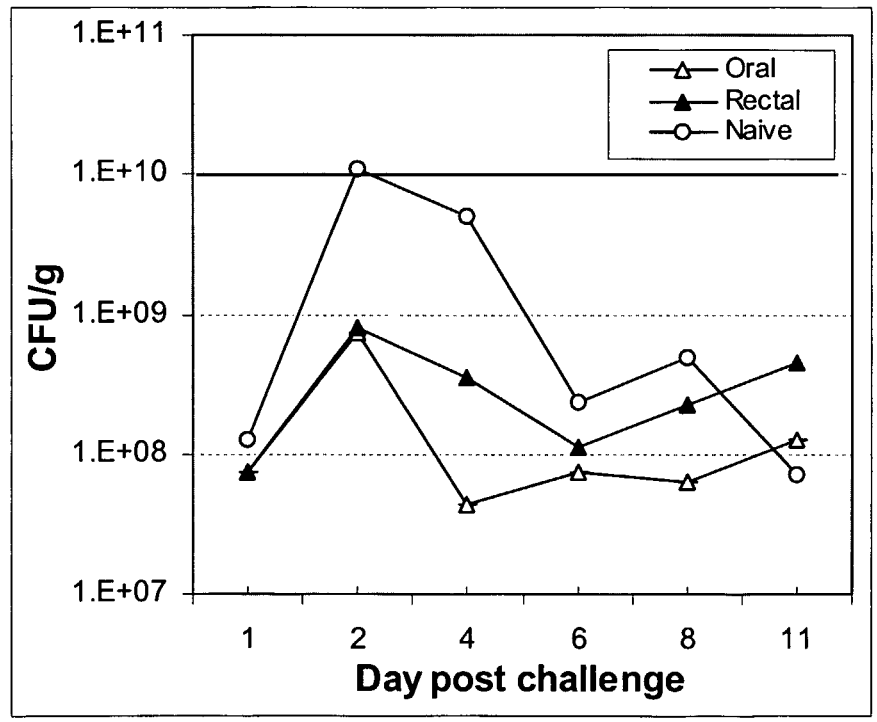

FIG. 20 is a graph showing a comparison of clearance of 0157:H7 in the intestinal tract of mice following oral and rectal immunization with 86-24 ΔeaeΔstx2AB with those receiving PBS. Challenge with 86-24 Δstx2AB was performed at 2 weeks (A) or 4 weeks (B) post booster immunization.

FIGS. 21A and 21B are graphs showing comparison of sera IgG titers specific to 0157:H7 LPS at day 0, 14, and 28, among groups receiving oral (FIG. 21A) or rectal (FIG. 21B) vaccination of 86-24 ΔeaeΔstx2AB. Dashed line indicates the cut-off value.

FIG. 22 is a graph showing a comparison of sera IgG titers specific to 0157:H7 LPS at day 28 following immunization among mouse groups receiving oral and rectal immunization of 86-24 ΔeaeΔstx2AB with naïve mice. Dashed line indicates the cutoff value.

Figure 23:
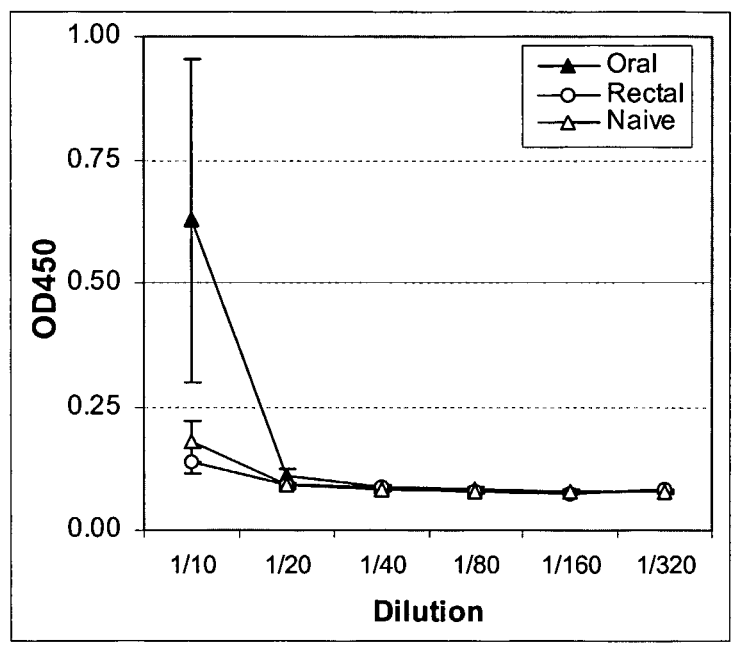

FIG. 23 is a graph showing a comparison of IgA titers specific to 0157 LPS from intestinal lavage. Bars represent the standard errors.

DETAILED DESCRIPTION OF THE INVENTION

STEC/EHEC strains cause bloody diarrhea and potentially fatal systemic sequelae in humans. A successful human vaccine would need to elicit anti-bacterial immunity to prevent bacterial adhesion or anti-toxin immunity to neutralize the Shiga toxin. While there is indirect evidence that human vaccination against STEC may be effective in preventing illness, at present, there are no human vaccines for STEC or effective intervention strategies. The difficulty in identifying such vaccines and interventions is hampered by the fact that human volunteers cannot be challenged with either virulent STEC or Shiga toxin preparations and that there are not enough incidences for field trials. Moreover, because of the sporadic nature of EHEC outbreaks, it is unlikely that universal vaccination of susceptible human populations will be adopted as a public health measure.

The present invention overcomes these above limitations and develops a novel vaccination approach, which will eliminate STEC strains from the food chain, where the major reservoirs of EHEC are cattle. Asymptomatic cattle are colonized by and shed these organisms leading to contamination of livestock-derived food products and water, and subsequent human STEC infections. Vaccination of cattle, which eliminate, inhibit or reduce the level of STEC shedding, can greatly impact the number of foodborne outbreaks. Immunization of cattle with live attenuated EHEC vaccine is expected to induce effective mucosal immunity, thus preventing or inhibiting EHEC colonization in the gut. Such immunization would provide safer meat and a cleaner environment.

The laboratory of the present inventors have developed a rabbit model for acute symptomatic STEC infection by introducing the Stx1-producing bacteriophage from a human O26 isolate into the rabbit enteropathogenic E. coli strain (REPEC) RDEC-I (Cantey et al., 1977; and Hicks et al., 1998). The resulting bacterium, RDEC-H19A, lysogenic for phage H19A, produces an illness in rabbits which closely resembles the hemorrhagic colitis induced by STEC in humans in both clinical course and histopathological findings (Hicks et al., 1998; and Sjogren et al., 1994).

A number of isogeneic mutants in REPEC defective in selective virulence genes, e.g., the regulatory genes ler and luxS and the genes coding for proteins involved in bacterial adherence (eae, tir and lifA), were constructed in the laboratory of the present inventors. LuxS is involved in quorum sensing in EPEC and EHEC bacterial cells (Sperandio et al., 1999 and 2001). The HfA is a lymphotoxin in human EPEC which down-regulates host immune responses (Klapproth et al., 2000). The HfA homologue in STEC/EHEC O111:H- is designated as efa1 (EHEC factor for adhesion) which has been ascribed an adherence function independent of the LEE (Nicholls et al., 2000). The efa1/lifA is present in all A/E organisms of human and animal origin (Badea et al., 2003). However, in human EHEC O157:H7, the efa1/lifA homologue is smaller (9507 nt) and located on the pO157 plasmid and named toxB (Badea et al., 2003 and Tasuno et al., 2001). The phenotype alterations of these mutants have been examined in vivo and in vitro. The potential of these mutants as vaccine candidates has been tested by experimental challenge with the WT REPEC strain RDEC-I (O15:H-) or E22 (O103:H2). Three classes of mutants have been observed: 1) fully attenuated, including the ler, eae, tir mutants; 2) partially attenuated, the HfA mutant; and 3) no in vivo attenuation, the luxS mutant. Only the data for the eae and ler mutant in the first class are presented in Examples 1 and 2 hereinbelow.

The laboratory of the present inventors has generated a substantial amount of information on the level of attenuation in virulence and mechanisms of homologous protection by using the rabbit STEC model and has demonstrated full attenuation of bacterial virulence by inactivation of the ler gene encoding a global regulator, the eae gene encoding intimin, or the tir gene encoding translocated intimin receptor Tir. The results presented in Example 1 hereinbelow demonstrate that intimin plays a critical role in A/E, and the intimin truncation mutation induced significant amounts of sera IgG against intimin and also induced effective protection. Likewise, the ler mutants in Example 2 hereinbelow are attenuated, and immunization with ler mutants provided protection against STEC of the same serotype. Thus, the studies in Examples 1 and 2 show that mutation in the eae and ler genes attenuated bacterial virulence while retaining their immunogenicity. The laboratory of the present inventors have also created tir mutants of REPEC and demonstrated attenuation in the virulence of the tir mutants. The immunogenicity of the tir mutant is expected to be similar to the eae and ler mutants.

The eae mutant in which the C-terminal Tir binding domain (TBD) is truncated or deleted would retain the immunodominant region of intimin and be able to induce antibody production that has been shown to be protective. Moreover, the eae truncation will not affect the expression of proteins encoded on the LEE and outside the LEE, which may enhance immune responses against EHEC because a full array of protein encoded by wild-type EHEC would be expressed with the exception of the truncation at the C-terminal portion of intimin. Because Ler is a central regulator for the genes encoded on the LEE, it is expected that the attenuated mutant will not express ler-regulated protein expression, such as Tir and other secreted proteins. The same strategies used in Examples 1 and 2 for REPEC can be applied to construct STEC/EHEC vaccines for cattle.

The present invention is directed to a live, attenuated enterohemorrhagic Escherichia coli (EHEC) in which the Shiga toxin Stx1 or Stx2 coding sequence, stx1A/stxB or stx2A/stx2b, is mutated, preferably deleted, to abolish Shiga toxin production, and one or more of the nucleotide sequence coding for bacterial adhesion protein intimin (eae), the locus of enterocyte effacement (LEE)-encoded regulator (ler), and the translocated intimin receipt (tir) are mutated, preferably by creating a deletion mutant, to inactivate the virulence-associated activity of the encoded protein(s).

The deletion of stxAB genes (stx1AB and/or stx2AB) will make EHEC non-toxic, and inactivation of either eae, ler, or tir will abolish A/E capacity of EHEC strains. In addition, modifying genes in the LEE such as eae, ler, or tir may have little impact on the function of accessory molecules involved in STEC colonization and persistence in the gut. Thus, a double mutation will fully attenuate bacterial virulence and make the live, attenuated EHEC strains safe for use as a vaccine in cattle. It will be appreciated by those of skill in the art that, while a double mutant is preferred, triple or quadruple mutants in which two or more of eae, ler, or tir are mutated are also encompassed in the present invention.

The present invention is also directed to a vaccine for reducing or inhibiting carriage and shedding of enterohemorrhagic *E. coli* in cattle, which vaccine contains a pharmaceutically acceptable carrier and an immunogenically effective amount of the live, attenuated enterohemorrhagic *E. coli*. The term "immunogenically effective amount" is meant to be the amount of live attenuated EHEC sufficient to induce in the host an effective immune response to the virulent EHEC strains of the same serogroup. This immunogenically effective amount is in a range of $IxIO^3$ to $IxIO^{10}$ CFU of the live attenuated bacteria, more preferably in a range of $IxIO^5$ to $IxIO^{10}$ CFU, and most preferably in a range of $IxIO^8$ to $IxIO^9$ CFU. The live attenuated EHEC belongs to serogroup 0157, 026 or 0111, preferably of serotype 0157:H7 and 011:H-. In the vaccine of the present invention, live attenuated EHEC of serogroups 0157, 026, and 0111 can be used alone or in combination to induce immunity against the most prevalent STEC serogroups.

The particular pharmaceutically acceptable carrier or diluent employed is not critical to the present invention. Examples of diluents include a phosphate buffered saline, buffer for buffering against gastric acid in the stomach, such as citrate buffer (pH 7.0) containing sucrose, bicarbonate buffer (pH 7.0) (Levine et al., 1987; and Black et al., 1987), or bicarbonate buffer (pH 7.0) containing ascorbic acid, lactose, and optionally aspartame (Levine et al., 1988).

Optionally, one or more compounds having adjuvant activity may be added to the vaccine. Adjuvants are non-specific stimulators of the immune system. They enhance the immune response of the host to the vaccine. Examples of adjuvants known in the art are Freund's Complete and Incomplete adjuvant, vitamin E, non-ionic block polymers, muramyldipeptides, ISCOMs (immune stimulating complexes, see for instance European Patent EP 109942), Saponins, mineral oil, vegetable oil, and Carbopol™. Other suitable adjuvants are for example aluminium hydroxide, aluminium phosphate or aluminium oxide, oil-emulsions (e.g. of BAYOLF™ or MARCOL 52™, saponins or vitamin-E solubilizate.

Other examples of pharmaceutically acceptable carriers or diluents useful in the present invention include stabilizers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer). Especially when such stabilizers are added to the vaccine, the vaccine is very suitable for freeze-drying.

The present invention is further directed to a method for reducing or inhibiting carriage and shedding of enterohemorrhagic *Escherichia coli* in cattle, which involves immunizing cattle with the vaccine of thβ 'present invention to reduce or inhibit carriage and shedding of enterohemorrhagic *E. coli* in the immunized cattle.

The mucosal and systemic immune systems are compartmentalized (Mesteky, 1987; Newby, 1984; and Pascual et al., 1994). Thus, antigens delivered to mucosal surfaces elicit mucosal and systemic responses, whereas parentally delivered antigens elicit mainly systemic responses but only stimulate poor mucosal responses (Mesteky, 1987). Moreover, mucosal stimulation at one mucosal site (for example the intestine) can result in development of immunity at other mucosal surfaces (for example genital/urinary tract) (Mesteky, 1987). This phenomenon is referred to as the common mucosal system and is well documented (Mesteky, 1987; and Pascual et al., 1994).

Mucosal surfaces comprise the largest surface area of the human and animal body and are the first line of defense against many pathogens. The oral route of vaccination has been widely used in the vaccination practice, both in humans and animals. The disadvantage of oral administration of vaccines for cattle is that, in these animals gastric acid provides a formidable barrier against microorganisms, and is highly-effective in killing orally administered, attenuated live bacterial vaccines. In addition, the complex rumen, with its own flora, represents an additional barrier to establishment of live vaccine strains given orgogastrically. Another well-established avenue for effective induction of the gut-associated immunity is intrarectal immunization. Studies conducted in mice demonstrated that rectal immunization elicits high levels of specific immune responses (Hopkins et al., 1995; Kawahara et al., 2002; Mitchel et al., 2003a; Zhou et al., 1995). The sub-epithelium at the bovine terminal rectum contains a high concentration of lymphoid follicles (Naylor et al., 2003) and has all the characterisitics of a classical inductive site for mucosal immunization. It is noteworthy that this organized lymphoid tissue has been proposed as the predominant site of carriage of STEC strains in cattle. In one study, the majority of tissue-associated EHEC 0157:H7 were adherent to mucosal epithelium within a defined region extending up to 5 cm proximally from the recto-anal junction (RAJ) having a high density of lymphoid follicles. For this reason, rectal immunization in cattle may be uniquely able to directly induce local immunity in the sites of colonization (Low et al., 2003).

Because the mucosal surface is the primary site for STEC attachment, the vaccine of the present invention is preferably administered to induce mucosal immunity. The vaccine is more preferably administered orally (with prior administration of sodium bicarbonate, for example, to neutralize stomach acidity) or intrarectally.

A still further aspect of the present invention is directed to a method for producing the isolated live, attenuated enterohemorrhagic *Escherichia coli* of the present invention, which involves deleting any Shiga toxin sequences coding for active Shiga toxin in an enterohemorrhagic *E. coli* of serogroup 0157, 026 or 0111 to abolish Shiga toxin production and mutating, preferably by introducing a deletion in, one or more of the nucleotide sequences coding for the bacterial adhesin protein intimin (eae), the loss of enterocyte effacement-encoded regulator (ler), and the translocated intimin receptor (tir) to inactivate the virulence-associated activity of the encoded protein (s).

Having now generally described the invention, the same will be more readily understood through reference to the following examples which are provided by way of illustration and are not intended to be limiting of the present invention.

Example 1

Protection Against Hemorrhagic Colitis in an Animal Model by Oral Immunization with an Isogeneic Rabbit Enteropathogenic *Escherichia coli* Expressing Truncated Intimin A rabbit model for EHEC infection by introducing Stx1-converting phage into a rabbit A/E pathogen RDEC-I to obtain strain RDEC-Hl 9A was previously developed in the laboratory of the present inventors (Sjogren et al., 1994). The rabbit EHEC model reproduces both the A/E pathology and the vascular damage and inflammation attributable to Stx and is a suitable model for evaluating various EHEC interventions (Sjogren et al., 1994). In this example, an eae mutant of RDEC-I was constructed and examined for both the level of attenuation in virulence and the effectiveness of this eae mutant as a vaccine candidate. RDEC-lΔeae is shown to be fully attenuated and well tolerated in rabbits. It is further shown that immunization of rabbits with RDEC-lΔeae protected animals from occurrence of diarrhea, weight loss, and tissue damage induced by virulent RDEC-H19A. Thus, the attenuation of an AEEC strain by the truncation of intimin is expected to provide an effective vaccine for the prevention of EHEC infection.

Materials and Methods

Bacterial Strains and Culture Conditions.

Strains used in this study are listed in Table 1. The prototype RDEC-I (015:H-) was originally isolated from rabbits with diarrhea (Cantey et al., 1977). Strain RDEC-H19A is a RDEC-I derivative containing the Stx-I-producing phage H19A from human 026 EHEC (Sjogren et al., 1994). The laboratory *E. coli* strain DH5α was used for plasmid transformation except in the case of suicide plasmids (pCVD442 and its derivatives)—which were maintained in *E. coli* SY327 or SMlO (Donnenberg et al., 1991). Bacterial strains were stored at −70° C. in Luria-Bertani (LB) containing 20% glycerol and grown on LB agar or broth or otherwise described. Appropriate antibiotics were supplemented to the media when needed at the following concentrations: ampicillin (Amp), 50 μg/ml; nalidixic acid (Nal), 20 μg/ml; tetracycline (Tet), 25 μg/ml.

TABLE 1

Bacterial strains and plasmids used in this study (Example 1)

| Strains & plasmids | Relevant features | Source or reference |
|---|---|---|
| Strains: | | |
| DH5α | Laboratory *E. coli* strain | |
| RDEC-I | O15:H-, Nal$^R$ | Cantey et al., 1977 |
| RDEC-H19A | RDEC-I transduced with phage H19A, Nal$^R$ Tet$^R$ | Sjogren et al., 1994 |
| SM10 | SM10 λpir, recipient for suicide vector pCVD442 | Donnenberg et al., 1991 |
| TSA01 | SM10 containing pM381 | This study |
| RDEC-\Aeae | RDEC-IΔeae, Nal$^R$ | This study |
| Plasmids: | | |
| pALT417-3 | PALTER-I ::RDEC-Ie αe, Amp$^R$ | |
| p368 | Derived from pALT417-3 with one bp deletion in the eae, Amp$^R$ | This study |
| pCVD442 | Suicide vector, Amp$^R$ | Donnenberg et al., 1991 |
| pM381 | pCVD442:: Δeae, Kan$^R$, Amp$^R$ | This study |

Construction of an Eae Truncation Mutation in RDEC-I.

A 4.36 kb HindIII DNA fragment containing RDEC-I eae gene (excluding the first 100 bp) and downstream sequences was cloned into pALTER-1 and site-directed mutagenesis of the eae gene was achieved using the single stranded phagmid protocol and mutant oligo 224832C (5'-GATGCCGAAAA-CAACTGTAAGACAAATAGCGCAA-S'; SEQ ID NO:1) following manufacturer's guidance (Promega Inc., Madison, Wis.) to obtain plasmid p368. This oligo contains a single base pair deletion at the position of 2565 nt in the eae coding sequence (FIG. 3A) thus resulting in a frame shift which generates a stop codon twenty-three base pairs downstream of the deletion (FIG. 3A). A DNA fragment containing the mutated eae gene was excised from pALTER plasmid by XbaI digestion and cloned into Xba I-digested suicide plasmid pCVD442, resulting in plasmid pM381. Plasmid pM381 was transformed into *E. coli* strain SY327 and the resultant plasmid transformed subsequently into strain SM10 to obtain strain TSA01 (Table 1). A chromosomal eae mutation in RDEC-I was generated by allelic exchange as described by Donnerberg and Kaper (Donnenberg et al., 1991). The Amp$^s$, Nal$^R$, sucrose-resistant bacteria that underwent allelic exchange were screened for FAS (fluorescence actin staining) activity on HEp-2 cells as previously described (Karaolis et al., 1997). Strains that failed to induce actin aggregation on HEp-2 cells were further examined by sequencing the intimin C-terminal portion using PCR-amplified DNA with a pairs of primers (Agin1, 5'-CCAGTATTACTGAGATTAAG (SEQ ID NO: 2), 27351-2737lnt; Agin2, 5'-TCCGGGATTTGAGAT-GTAAT (SEQ ID NO:3), 28223-28204 nt) derived from RDEC-I LEE (GenBank Accession #AF200363) (Zhu et al., 1995). Expression of the truncated intimin by RDEC-1Δeae was examined by separation of bacterial outer membrane preparations by SDS-PAGE as described (Zhu et al., 1995).

Examination of In Vivo Virulence of RDEC-1Δeae and Protection Following Immunization.

The in vivo virulence of RDEC-1 Δeae was determined in 2 month-old New-Zealand White rabbits. Bacteria strains were streaked onto MacConkey agar supplemented with NaI and an individual colony was then inoculated into 100 ml Penassy broth (PAB; antibiotic medium 3 Difco) and cultured at 37° C. overnight without shaking. Bacteria were washed once and suspended in sterile PBS and adjusted to the concentration of OD$_{600}$ 0.10 (approximately 1×10$^8$ cfu/ml). Bacterial viable counts were determined by standard plating methods. Rabbits were fasted overnight and unsedated animals were inoculated intragastrically via pediatric feeding tube with 10 ml 10% bicarbonate solution to neutralize gastric contents followed by the inoculum. Inocula consisted of a total volume of 3 ml of PBS containing RDEC-I or its derivative RDEC-1 Δeae. The tube was then flushed with 5 ml sterile PBS to ensure that the total inocula were delivered into the stomach. Rabbits were sacrificed fourteen days post inoculation.

To determine if RDEC-1 Δeae immunization would protect animals from experimental challenge, rabbits were orogastrically inoculated with RDEC-1 Δeae as described above and boosted with the same dose 14 days later. Rabbits orogastrically inoculated with PBS served as controls. Fourteen days post boost, rabbits were challenged with 5×10$^7$ CFU of RDEC-H19A, a Stx1-producing RDEC-I derivative, which is highly virulent to its natural rabbit hosts (Sjogren et al., 1994). Rabbits were sacrificed seven days post challenge.

Animals were observed daily for clinical signs of disease. Rabbit weights were recorded and stool consistency scored daily. Fecal shedding of inoculated bacteria was determined for each rabbit by semi-quantitative cultures of rectal swabs as previously described (Sjogren et al., 1994). In brief, rectal swabs are rolled onto MacConkey plates (supplemented with Tet and NaI or NaI alone for RDEC-H19A or RDEC-1 Δeae, respectively) and grown overnight at 37° C. and graded as 0 (no CFU), 1+ (1-50 CFU), 2+ (50-200 CFU), 3+ (>200 CFU), or 4+ (confluent growth).

Rabbits were euthanized according to standard protocols. At necropsy, the abdominal organs were inspected for serosal hemorrhage and bowel edema, and the degree of liquidity of cecal contents was observed and recorded. Transmural sections from the distal ileum, cecum, proximal colon, and distal colon were excised and fixed in 10% buffered formalin for sectioning. Tissues were stained with hematoxylin and eosin (H&E) or with Giemsa. Microscopic examination of histopathology was based on ten sequential, well-oriented, 400× fields from each sample. Bacterial enteroadherence was graded as the percentage of surface area in the field which is covered by closely adherent bacteria (Sjogren et al., 1994). Edema depth was quantitated with an ocular micrometer by measuring the distance from the muscularis mucosa to the muscularis propria. Heterophils are counted in the mucosa, in fields immediately adjacent to the muscularis mucosa extending luminally to the limits of the 250 μm diameter field (40× objective). Counts from ten fields are tabulated, averaged and expressed as heterophils per high power field. Vascular changes, including endothelial swelling, adherent heterophiles, endothelial denudation and thrombus formation were measured separately in sequential vessels in the mucosa, submucosa, and serosa and graded from 0 to 4 scales (Sjogren et al., 1994). A composite score for vascular changes based on summation of the scores for the four individual parameters was calculated for each of the three tissue compartments.

Detection of Antibodies Specific to RDEC-I Intimin.

For serum and mucosal antibody detection, sera were prepared and bile was aspirated from the gallbladders. A maltose-binding protein (MBP)-intimin fusion protein was constructed by cloning PCR-amplified 843-bp fragment containing the C-terminal 280aa portion of RDEC-I intimin into the pMAL-p2 (New England Biolabs, Beverly, Mass.) according to manufacturer's instructions. The MBP-intimin fusion protein was isolated from B. coli periplasm by affinity chromatography (Again et al., 1997). Sera IgG or bile IgA specific to RDEC-I intimin was determined by ELISA as previously described (McKee et al., 1996). Briefly, microtiter wells (LabTeck) were coated with MBP-intimin fusion protein at the concentration of 4 μg/ml in bicarbonate buffer at pH 9.6. Serial dilutions of rabbit sera or bile were added, and bound antibodies were detected with HRP-conjugated sheep anti-rabbit IgG or goat anti-rabbit IgA and developed with ABT peroxidase substrate (KPL, Gaithersburg, Md.).

Statistical Analysis.

Values for differences in rabbit weight gain, bacterial adherence, and histological findings between experimental groups were compared by the Student T-Test Results Frame Shift Mutation Resulted in Intimin Truncation.

A single nucleotide deletion was made at 2565 nt in the eae coding sequence of RDEC-I (SEQ ID NO: 4). As a result of the frame shift, a stop codon is introduced 24 bp immediately after deletion (FIG. 3B). Thus, the intimin C-terminal 81 residues (860-939aa) containing a disulfide loop was truncated and replaced by a series of new eight residues (NVR-QIAQI, residues 18-25 of SEQ ID NO:6; FIG. 3A). Therefore, the predicted truncated intimin is composed of 866 residues, which is 73 aa shorter than the native intimin molecule.

Conjugation of RDEC-I with conjugative strain TSA0l (SM10 containing suicide plasmid pCVD442; Donnenberg et al., 1991) yielded numerous colonies, one of which was cultured overnight in LB broth without antibiotics and subsequently plated on LB containing 5% sucrose. Individual colonies grown on LB supplemented with sucrose were examined for antibiotic resistance profile. The Amp-resistant bacteria were selected to further characterized by the fluorescent actin staining (FAS) test on HEp-2 cells (Karaolis et al., 1997). Four isolates that were negative by FAS assay (data not shown) were recovered. Nucleotide sequencing of PCR amplicons using primers Agin1/Agin2 for the FAS-negative isolates showed a nucleotide deletion at the position of 2565 nt in the eae gene. One of these isolates was designated as RDEC-1Δeae and used in subsequent study.

Because the truncated intimin has 73 fewer residues than the native intimin, a molecular weight shift is expected for the truncated intimin. The predicted sizes for the native and truncated intimins are 101.7-kDa and 97.0-kDa, respectively. Since post-translational modification of intimin eliminates the signal peptide of 39 aa (Zhu et al., 1995), the mature intimins of RDEC-I or RDEC-1 Δeae are 97.1-kDa or 89.2-kDa, respectively. Consistent with previous observations (Zhu et al., 1995), Coomassie brilliant blue staining of SDS-PAGE-separated OMP extracts from the WT strain RDEC-I revealed an intimin protein band with estimated molecular mass of 97-kDa (FIG. 3C). However, this 97-kDa-protein band was missing in strain RDEC-1 Δeae. Rather, a protein band with estimated molecular mass of 90-kDa was present for RDEC-1 Δeae (FIG. 3C), confirming a molecular weight shift from native intimin expressed by the WT RDEC-I to the truncated intimin expressed by RDEC-1 Δeae.

Effect of the Intimin Mutation on In Vitro Adherence to HEp-2 Cells and In Vivo Pathogenicity The intimin C-terminal 76-aa disulfide loop has been shown to be essential for Tir-bing (Frankel et al., 1995; Hicks et al., 1998; and Luo et al., 2000). Thus, elimination of this disulfide loop is expected to abolish Tir-binding capacity of RDEC-1 Δeae. When examined by HEp-2 cell adherence assay, the mutant strain RDEC-1 Δeae is unable to induce actin accumulation on HEp-2 cells as had been observed for the parent strain RDEC-I (data not shown).

The level of in vivo virulence of the WT RDEC-I and its isogeneic ler mutant, RDEC-1 Δeae was compared. Rabbits inoculated with RDEC-1 Δeae remained clinically normal and they gained an average weight of 488 g by day 14 post inoculation (FIG. 4A). Fecal shedding of RDEC-1 Δeae occurred within 24 hrs and persisted for nearly ten days (FIG. 4B). Light microscopic examination of tissues from ileum, cecum, and colon revealed no mucosal ly adherent bacteria and normal morphology (data not shown).

All rabbits receiving WT RDEC-I developed mild diarrhea ranging from soft stools to watery discharge. These rabbits initially gained as much body weight as those inoculated with RDEC-1Δeae until day three post inoculation but gained less weight than RDEC-1Δeae-inoculated rabbits thereafter. They gained an average weight of 220 g by day 14 post inoculation which is significantly (p<0.006) less than RDEC-1 Δeae group (FIG. 4A). They shed high numbers of inoculated organisms during the whole observation period (FIG. 4B). Consistent with previous studies, typical A/E lesions with cupping of adherent bacteria and effacement microvilli were observed among rabbits inoculated with the WT RDEC-I (data not shown). This initial comparison clearly indicates the attenuated virulence of RDEC-1 Δeae.

Protection of Rabbits Following RDEC-1Δeae Immunization.

Further experiments were carried on to determine the level of protection provided by RDEC-1 Δeae. All RDEC-1Δeae-immunized rabbits discharged normal stool (FIG. 5A) and had an average cumulative weight gain of 170 g by day seven post RDEC-H19A challenge (FIG. 5B). In contrast, all non-immunized rabbits manifested abnormal stools ranging from soft stools to frank watery diarrhea (FIG. 5A). They lost an average of 350 g body weight (50 g/day) during the same period (FIG. 5B). Fecal shedding of inoculated organisms was observed in rabbits of both RDEC-1 Δeae-immunized and PBS control groups. However, the level of fecal bacterial shedding was greatly reduced in RDEC-1Δeae-immunized rabbits compared to PBS control rabbits (p<0.01) (FIG. 5C). While confluent growth of Nal/Tet-resistant RDEC-H19A was observed in fecal pellets of un-immunized rabbits, only approximately 50 CFU per swab inoculation were seen for the RDEC-1Δeae-immunized rabbits.

Major differences in gross appearance of the intestinal tissues were observed between immunized and non-immunized rabbits challenged with virulent RDEC-H19A. All immunized and challenged rabbits exhibited normal appearance of intestinal mucosa (ileum, cecum, and colon). However, non-immunized rabbits showed varying degrees of gross pathological changes, including pale cecum and proximal colon, watery intestinal contents, and edematous and thickened cecal walls.

Figure 1:
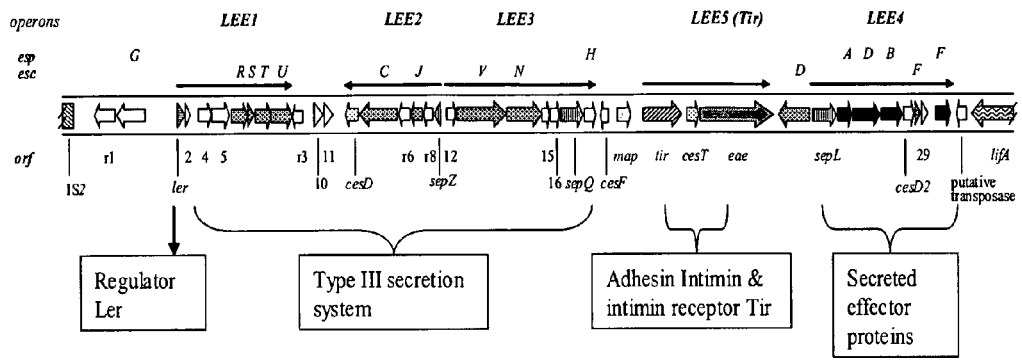
FIG. 1 is a schematic illustration of the genetic organization of RDEC-I LEE pathogenicity island.
Figure 2:
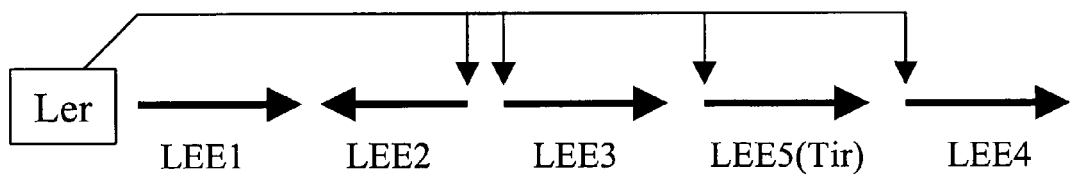
FIG. 2 is a schematic illustration of the regulation of LEE operons by Ler.
Figure 6:
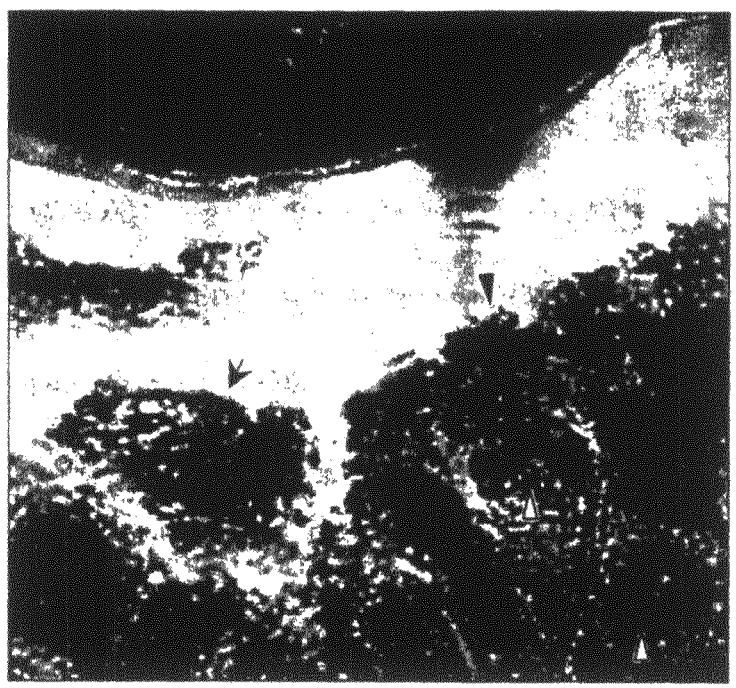
FIG. 6 show histological sections from a non-immunized rabbit challenged with RDEC-H19A showing intimate bacterial adherence and effacement of microvilli. Bacteria are adhering to the cecal enterocytes lining the villi (solid arrow). The intestinal villi became irregular and a cluster of cells has been desquamated from the villi (arrow). The lumina propria was infiltrated with polymorphonuclear leukocytes (semi-solid arrow heads). H&E staining, magnification, ×1,000.

Microscopically, mucosally closely adherent RDEC-H19A were seen covering on 10% surface area of the cecal mucosa (FIG. 5D). The severity of A/E lesions induced by RDEC-Hl9A varied from extensive attachment/effacement to small-scattered focal lesions with a small cluster of adherent bacteria and irregularity of intestinal mucosa. In areas of adherence, the epithelial cells became irregular with reduced cytoplasm. Frequent clusters of cells were observed to be desquamated from the mucosal surface (FIG. 6). The A/E lesions, when observed, were most severe in the cecum and in the proximal colon (data not shown). However, less than 1% of the cecal surface had observable adherent bacteria among the RDEC-1Δeae-immunized rabbits (FIG. 5D). Where bacteria attached, the integrity of epithelial cells remains unchanged.

Figure 7A:
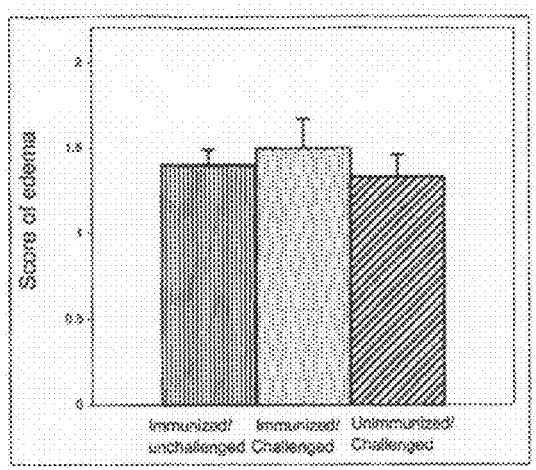
FIGS. 7A-7D are graphs showing comparisons between un-immunized/challenged (vertical line), immunized/challenged (semi-solid), and immunized/un-challenged (hatched columns) rabbits of histopathological findings for edema (FIG. 7A), heterophiles (FIG. 7B), vascular abnormalities (FIG. 7C), and thrombus formation (FIG. 7D). Bars represent standard errors.
Figure 7B:
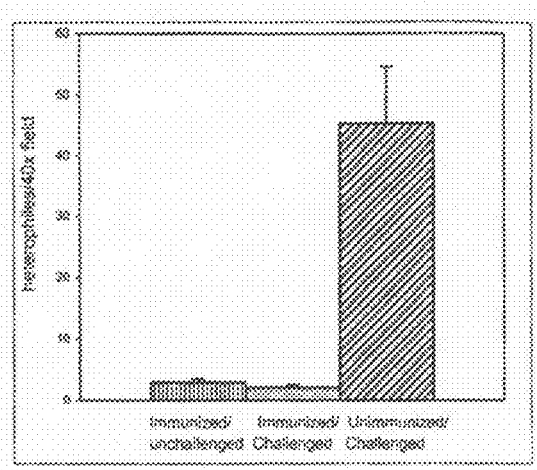
Figure 7C:
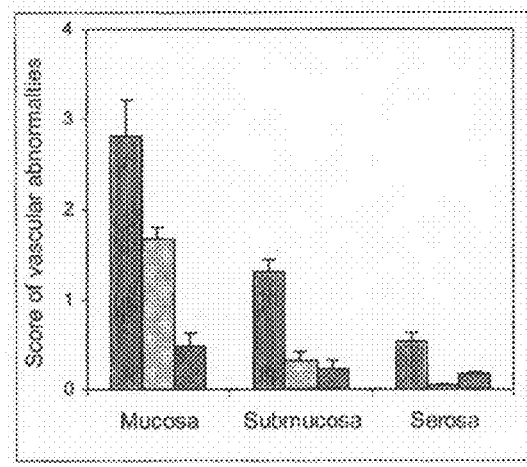
Figure 7D:
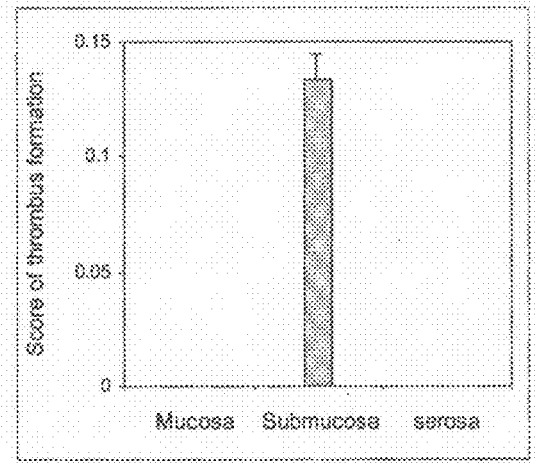

The WT RDEC-Hl9A induced marked submucosal edema in rabbits of all groups (FIG. 7A). This pathology correlates with the thickened cecal wall seen on gross examination (Sjogren et al., 1994). RDEC-H19A induced inflammatory infiltrates of polymorphonuclear of heterophiles among unimmunized rabbits but not immunized ones (FIG. 7B). Vascular changes in the mucosa, submucosa, or serosa were seen among unimmunized rabbits (FIG. 7C). However, decreased vascular changes were observed in the mucosa of immunized rabbits as compared to those observed in the un-immunized/challenged rabbits. The vessels in the submucosa and serosa appeared as normal as in the immunized-non-challenged rabbits. Thrombus formation (rare) was only observed in the submucosa of immunized rabbits (FIG. 7D).

Immune Responses.

Figure 8:
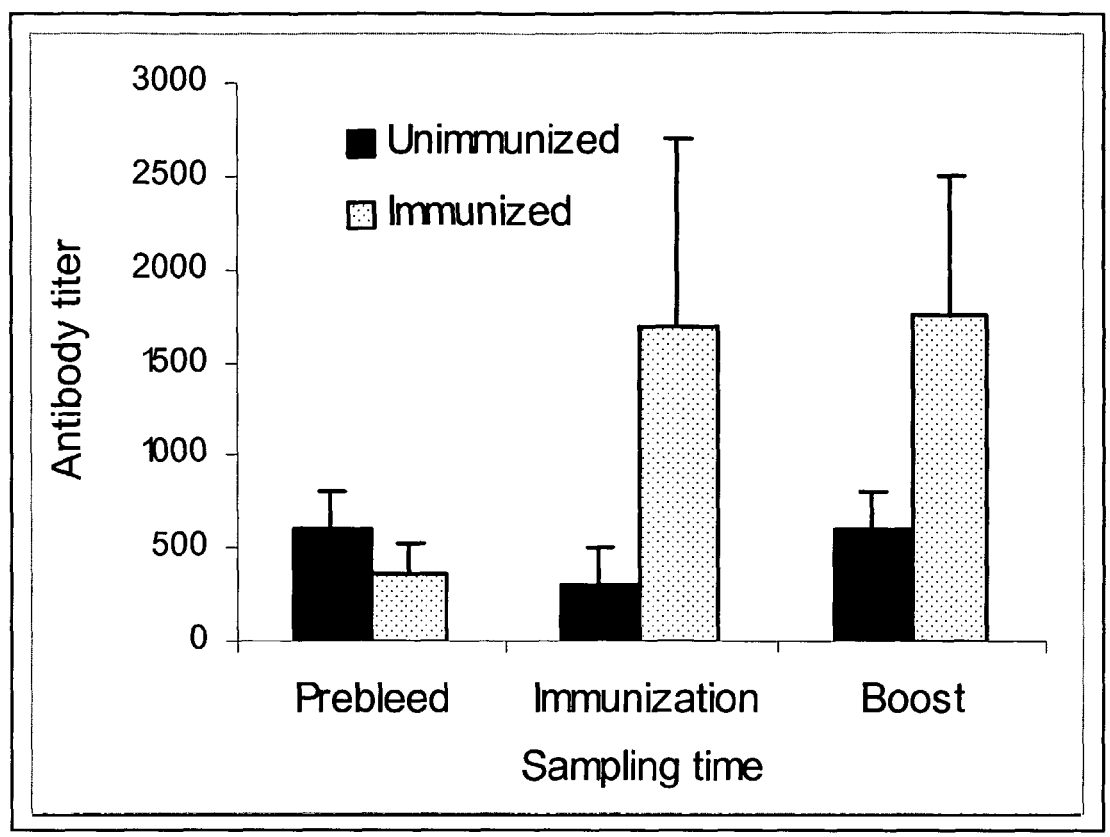
FIG. 8 is a graph showing rabbit serum IgG titers specific to MBP-Int280 following immunization with RDEC-l Δeae. Bars designate standard errors.

Serum and biliary antibodies specific to RDEC-I intimin were measured by ELISA using RDEC-I intimin-MBP fusion protein. Among PBS control rabbits, the intimin-specific IgG titer maintained the same low level during sampling period. However, intimin-specific IgG sharply increased following immunization with RDEC-1Δeae but did not show further increase following boost (FIG. 8). Biliary IgA specific for intimin was not detected in any group (data not shown).

Discussion

Interaction of intimin to its receptor, Tir, plays a key role in intimate adherence of AEEC to the host intestinal mucosa (Jerse et al., 1990; Kaper et al., 2004; and Kenny et al., 1997). Early studies demonstrated that the isogeneic intimin mutants are deficient in virulence as examined in human volunteers (Donnenberg et al., 1993a), in piglets (Donnenberg et al., 1993b) and in rabbits (Marches et al., 2000). Further supporting this is the fact that intimin immune responses can modulate the outcome of A/E organism infection as antibodies specific to intimin blocked intimin-mediated attachment (Dean-Nystrom et al., 2002 and Ghaem-Maghami et al., 2001). These results establish that intimin may serve as a putative candidate protein for attenuation as well as a crucial vaccine component. Functional and structural studies at molecular level on intimin further suggest that it is feasible to attenuate bacterial virulence while retaining its immunogenicity by one single step to eliminate the Tir-binding domain located in the D3 region of native intimin.

To test this hypothesis, the laboratory of the present inventors have constructed in the current study an eae mutant by a single nucleotide deletion to truncate the C-terminal 81 residues containing a disulfide loop essential for intimin function. It was demonstrated that RDEC-1Δeae is unable to induce A/E lesions in vitro and in vivo indicating successful attenuation of virulence of the WT RDEC-I. The results in this Example are in full agreement with previous reports that defined mutation in the eae attenuated virulence of human EPEC, EHEC, and rEPEC strains (Sonnenberg et al., 1991; Donnenberg et al., 1993a and 1993b and Marches et al., 2000). Donnenberg and Kaper created an internal 1848-bp deletion in EPEC eae gene (Donnenberg et al., 1991) and demonstrated that while all of the human volunteers received WT EPEC developed diarrhea, the isogeneic eae mutant caused diarrhea among only 4 of 11 individuals (Donnenberg et al., 1993a). In a separate study, the isogeneic eae mutant of EHEC strain 86-24 (0157:H7) generated by replacing the internal 1.1-kb eae DNA with a 2.9-kb NDA fragment containing a Tet marker was unable to colonize in the experimentally inoculated piglets (Donnenberg et al., 1993). In another rEPEC strain belonging to the serogroup O103:H2, an insertion of aphT encoding Kan resistance in the eae gene (between 993 nt and 994 nt) disrupted the expression of intimin and abolished bacterial virulence when tested by experimental inoculation of it natural rabbit host (Marches et al., 2000).

One of the unique features of the eae mutant constructed in the current study is the preservation of the remaining intimin molecule unaltered while the intimin functional D3 domain is truncated. This novel strategy retains immunogenicity of intimin which constitutes an important component of the attenuated live bacterial vaccines. The elevated serum IgG levels specific to intimin only seen among rabbits immunized with the isogeneic RDEC-1Δeae is an indication that the truncated intimin retains sufficient immunogenicity to boost immune responses to intimin. This specific immunity, combined with immunity to serotype-specific antigens and other as-yet unidentified factors, may contribute to the protection of rabbits from A/E pathological effects caused by virulent RDEC-H19A. Although a significant increase of specific IgA responses in biles of immunized rabbits was not observed it may be necessary to recover antibodies from the biles of immunized animals prior to challenge to determine the level of secretory IgA immunity.

Although New Zealand White Rabbits lack Stx receptors in the kidney glomeruli, Stx receptors are present in the microvascular endothelium of the intestine, in particular in the cecum, and Stx-induced vascular lesion are evident in the intestinal mucosa following RDEC-H19A challenge (Sjogren et al., 1994) Thus, this RDEC-H19A infection model is appropriate to evaluate the effectiveness of RDEC-1Δeae as vaccine candidate to prevent toxin-induced vascular lesions. The presence of HC and Stx-related histopathological alterations in non-immunized rabbits but the absence of clinical illness and lesions in RDEC-1Δeae-immunized rabbits indicates protection of rabbits from Stx-induced pathological effects by RDEC-H19A. This protection likely results from the prevention of bacterial intimate adherence to the intestinal mucosa.

Furthermore, although intimin mutation abolishes the capacity of RDEC-I to attach closely to the intestinal epithelial cells, RDEC-1Δeae are still able to persist in the rabbit intestinal tract for over ten days. This persistence suggests that multiple adhesive factors, in addition to the intimin, are involved in RDEC-I colonization. RDEC-I express plasmid encoded AF/R1 fimbriae which mediates a species-specific mucosal attachment by interacting with a sialo-glycoprotein complex on the microvillus (Berendson et al., 1983; Cantey et al., 1999; and Rafiee et al., 1991). Studies also implicate the filamentous EspA-containing surface appendages in attachment of A/E organisms (Ebel et al., 1998). In addition, in nearly all AEEC, a large molecular weight protein Efa1 (EHEC factor for adherence)/LifA (lymphocyte inhibitory factor) has been shown to be an adhesive factor (Badea et al., 2003; Klapproth et al., 2000; and Nicholls et al., 2000), RDEC-I express EspA and LifA/Efa1 homologue (Zhu et al., 2001). In a separate study, the laboratory of the present inventors have demonstrated that the LifA/Efa1 plays a crucial role in in vivo colonization of RDEC-I because deletion mutation in the lifA/efa1 gene resulted in significantly reduced bacterial colonization by 100-fold (Mao et al., 2003). Thus, these adhesive factors may contribute collectively to the prolonged presence in the intestinal tract by the RDEC-I intimin mutant, independent of intimin-Tir binding. This persistence of the RDEC-1Δeae in the intestinal tract is favorable to promote the development of local immunity against subsequent infection.

The hallmark of pathogenicity of EHEC is the production of Stx implicated in the development of HUS (Griffin et al., 1991; Kaper et al., 2004; Noel et al., 1997; and O'Brien et al., 1992). Eliciting active immunity against Stx represents another an attractive option for the development of an EHEC vaccine. Challenge studies showed effective protection induced by immunization with Stx-toxoid (Ludwig et al., 2002), the A or B subunit (Bielaszewska et al., 1997), STX-liposome conjugates (Uchida et al., 2003), DNA vaccines (Capozzo et al., 2003), or purified mutant form of the toxin (Ishikawa et al., 2003). Another approach to prevent the toxin-induced consequences of EHEC infection is the use of toxin binding agents. Several such agents, with Stx neutralizing capacity, have been developed utilizing the trisaccharide moiety of globotriaosyl ceramide which can bind and inhibit Stx cytotoxic activity. One such neutralizer, called Synsorb PK, has been the subject of clinical trials (Armstrong et al., 1995). The Stx binding agents, based on carbosilane dendrimer, a series of carbosilane dentrimers having silicon core and branch points and, trisaccharides of GB3 at their terminals, referred to as SUPER TWIG, has been shown to markedly inhibit Stx-binding and stx-cytotoxicity in vivo (Nishikawa et al., 2002). In another report, a series of linear polymers of acrylamide, each with a different density of trisaccharide of globotriaosylceramide (Gb3), has been shown specifically bound to both Stx1 and Stx2 with high affinity and markedly inhibited the cytotoxic activities of these toxins (Watanabe et al., 2004). However, these binding agents have limitations, since they need to be continually given to patients to provide toxin-neutralizing activity. Although approaches in eliciting immunity specific to or in neutralizing the toxin activity would protect against death caused by Stx(s) produced during EHEC infection, they could not prevent the spread of infection. However, an attenuated live EHEC vaccine, such as the eae mutant constructed in this Example is expected to provide more effective protection against EHEC infection by preventing bacterial colonization by a majority of clinically relevant EHEC strains. A truncated attenuated eae mutant has more attractive features that make it an effective attenuated mucosal vaccine candidate. They are noninvasive enteric pathogens in nature and are well studied at the molecular level. They are able to colonize in the intestinal tract and induce potent mucosal and systemic humoral responses; and they are safe and immunogenic. Thus, this attenuated EHEC strain shows great promise as an effective vaccine candidate for the prevention of EHEC infection.

Example 2

A LEE Encoded Regulator (ler) Mutant of Rabbit Enteropathogenic *Escherichia coli* is Attenuated, Immunogenic, and Protects Rabbits from Lethal Challenge with the Wild-type Virulent Stain The nucleotide sequence of ler and the upstream regions of rEPEC strain E22(O103:H2) was determined, a defined deletion mutation in the ler gene in the wild-type strain was constructed and the role of ler on virulence and on immunogenicity was examined by in vitro and in vivo assays. The protective efficacy of the rEPEC ler mutant strain was further determined by challenging rabbits with the WT virulent strain following immunization with the isogeneic ler mutant. The results demonstrate that the Ler of EPEC O103:H2 is critical for both in vitro pathogenic effects and in vivo virulence and that immunization with this isogeneic ler mutant protected rabbits from fatal challenge with the virulent WT parent strain.

Materials and Methods
Bacterial Strains and Culture Conditions.
Bacterial strains and plasmids used in this study are listed in Table 2. The rEPEC strain E22 (O103:H2) was originally isolated from a rabbit with diarrhea (Marches et al., 2001). A nalidixic acid (Nal) resistant derivative of E22 was selected as described by Hane (Hane et al., 1969) and designated E22N. The laboratory *E. coli* strain DH5α was used for plasmid transformation except for suicide plasmids (pCVD442 and derivatives), which were maintained in *E. coli* SY327 or SM10 (Donnenberg et al., 1991). Bacterial strains were stored at −80° C. in Luria-Bertani (LB) broth containing 20% glycerol and grown on LB agar, LB broth, or MacConkey agar supplemented with appropriate antibiotic (s) at the following concentrations: Ampicillin (Amp), 50 µg/ml; kanamycin (Kan), 50 µg/ml, Nal, 50 µg/ml.

TABLE 2

Strains and plasmids used in this study (Example 2)

| Strains or plasmids | Relevant characteristics | Source or reference |
|---|---|---|
| *E. coli:* | | |
| E22 | rEPEC O103:H2 | Marches et al., 2001 |
| E22N | E22 derivative, Nal$^R$ | This study |
| SY327 | SY327 λpir, intermediate recipient for suicide vector pCVD442 | Donnenberg et al., 1991 |
| SM10 | SM10 λpir, recipient for suicide vector pCVD442 to serve as donor strain, Kan$^R$ | Donnenberg et al., 1991 |
| ECB132 | SM10 (pECBl 19), Amp$^R$, Kan$^R$ | This study |
| E22Δ/er | An isogeneic ler mutant of E22N, Nal$^R$ | This study |
| Plasmids: | | |
| pCR2.1 Topo | PCR cloning vector | Invitrogen |
| pECB049 | pCR2.1:: Δ/er | This study |
| pCVD442 | Suicide vector, Amp$^R$ | Donnenberg et al., 1991 |
| pECB119 | pCVD442:: Δ/er, Amp" | This study |

DNA Sequence Determination of rEPEC ler Region.
The ler gene and upstream −600 bp region were cloned using primers B750f and B751r (Table 3). For PCR amplification, PCR SUPERMIX high fidelity mixture (Gibco BRL, Rockville, Md.) was mixed with template DNA (E22N bacterial suspension in distilled water, 94° C. for 10 min) and the primers, while amplification was performed on the PTC-200 DNA Engine (MJ Research Inc., Waltham, Mass.) using the following protocol: 33 amplification cycles of denaturation at 94° C. for 60 s, primer annealing at 55° C. for 60 s, and elongation at 72° C. for 90 s, followed by a final extension step at 72° C. for 10 min. The entire reaction mixture was then analyzed by agarose gel electrophoresis and the DNA bands excised and purified with QIAquick gel extraction kit (QIAGEN, Valencia, Calif.) according to the manufacturer's instructions. The purified DNA was then sent for automated sequencing and analysis of nucleotide and amino acid sequences were performed with BLAST programs offered by the National Center for Biotechnology Information (NCBI, NIH, Bethesda, Md.)

Generation of a Defined rEPEC ler Mutant.

Recombinant DNA techniques were performed according to standard procedures (Sambrook et al., 2001). Oligonucleotides (Table 3) were designed to generate a 300 bp internal deletion in the ler gene by single-overlap extension PCR (SOE PCR) using denatured bacteria as DNA template (Senanayake et al., 1995). Two pairs of primers (B650f/B648r and B647f/B649r) were used to independently amplify the 5'- or 3'-region of ler including flanking sequences, respectively. Primers B648r and B647f contain 18 bp stretches complementary to each other. PCR amplicons from the above two separate PCR reactions were gel-purified as described above, mixed, and used as DNA templates for the second PCR amplification to achieve assembly using primers B650f and B649r. The resultant 1,350-bp PCR product, containing an internal deletion of 300 bp (from 44 to 343 nt) in the ler gene, was purified and subsequently cloned into pCR2.1-TOPO vector (Invitrogen, Carlsbad, Calif.) to generate plasmid pECB049. The nucleotide sequence of the insert was determined by DNA sequencing as described above. Plasmid pECB04 9 was then digested with Sac I and Xba I endonucleases and the DNA fragment containing the mutated ler was then ligated with the suicide plasmid pCVD442 (Donnenberg et al., 1991) digested with Sac I and Xba I to yield plasmid pECB119 which was transformed into E. coli SY327 (λpir) containing the pir gene necessary for replication of pCVD442 Plasmid pECB119 was then prepared from SY327 and subsequently transformed into strain SM10 (λpir) (which contains the conjugal functions of plasmid pCVD442 so that the plasmid can be transferred to the recipient strain for mutagenesis) and plated onto LB agar supplemented with Amp and Kan to yield strain ECB132.

Conjugation between the recipient WT E22N and the donor ECB132 was performed to achieve the desired defined mutation of Ler (Donnenberg et al., 1991). Replacement of the chromosomal ler gene with this in-frame, non-polar mutated ler was confirmed by PCR using two sets of primers (B650f/B649r, or B650f/B810r). Primers B650f and B649r yield fragments of 1650 bp or 1350 bp for the intact or mutated ler, respectively, whereas primers B650f and B810r yield a 778 bp fragment only in the presence of the intact ler but yield no product for the mutated ler.

TABLE 3

Oligonucleotides used in this study (Example 2)

| Oligo | Sequence | Position in the RDEC-I LEE |
|---|---|---|
| B750f | 5'-ccggaattc/ cgaatggtacggttatgc (SEQ ID NO: 7) | EcoRI/3979-3996 |
| B751r | 5'-cgcggatcc/ agttcagttatcgttatcatt (SEQ ID NO: 8) | BamHI/4931-491 1 |
| B650f | 5'-gggatagatatgggaata (SEQ ID NO: 9) | 3951-3968 |
| B648r | 5'-cttcggtgtccttcacaa/ tgtgcgaattagtttcca (SEQ ID NO: 10) | 4868-4851/4550-4533 |
| B647f | 5'-ttgtgaaggacaccgaag (SEQ BD NO: 11) | 4851-4868 |
| B649r | 5'-attacgagtagaactact (SEQ ID NO: 12) | 5600-5583 |
| B810r | 5'-cgagcaaggccatcatcagg (SEQ ID NO: 13) | 4728-4709 |

Examination of Secreted Protein Profiles.

Bacterial secreted proteins were prepared as described (Sperandio et al., 1999). Briefly, overnight culture of bacteria in LB were adjusted to an optical density of 1.0 at 600 nm and 100 µl of such bacterial suspensions were added into 100 ml DMEM containing 5% fetal bovine serum. After overnight growth at 37° C., the bacterial cells were removed by centrifugation at 4° C. and phenylmethylsulfonyl fluoride was added to the supernatants to a final concentration of 1 mM (Zhu et al., 1995) Supernatants were then concentrated using a Filtron Stirred Cell with MW cutoff of 3-kDa (Filtron Technology Corporation, MA) and resuspended in PBS to a final volume of 1 ml. A total of 20 µl of such a preparation was separated by SDS-PAGE on 12% gel system and protein bands were visualized by silver staining as described (Zhu et al., 1995).

Initial Examination of In Vivo Virulence.

The in vivo virulence of the rEPEC isogeneic ler mutant was examined by experimental inoculation of two-month old New Zealand White rabbits. Rabbits were fasted overnight and un-sedated animals (six per group) were inoculated intragastrically via a pediatric feeding tube with 10 ml 10% bicarbonate solution to neutralize gastric contents followed by the inoculum. Inocula consisted of a total volume of 3 ml of PBS containing WT parent rEPEC E22N or E22Δ2er or PBS (control group) (Table 4). Finally, the tube was flushed with 5 ml sterile PBS to ensure complete delivery of inocula into the stomach.

Rabbits were examined daily for clinical signs of diarrhea and their weights were determined daily. Fecal samples were graded as normal pellets, soft stools, and watery or bloody diarrhea. Rabbits that lost greater than 20% body weight or demonstrated severe watery or mucoid diarrhea or bloody diarrhea were euthanized and recorded as non-survival s. Fecal bacterial shedding was determined semi-quantitatively on MacConkey agar supplemented with appropriate antibiotics. In brief, rectal swabs were rolled onto agar plates and grown overnight at 37° C. and scored as 0 (no CFU), 1+ (1-50 CFU), 2+ (50-200 CFU), 3+ (>200 CFU), or 4+ (confluent growth).

At sacrifice, rabbits were euthanized according to standard protocols to obtain histological sections of the intestine and quantitative bacterial counts of the inoculated strains. For comparison of virulence of WT E22 and its isogeneic ler mutant, animals were sacrificed at five days, since extreme weight loss in the group receiving strain E22N demanded sacrifice at this time. At necropsy, the degree of gross cecal and colonic edema, and degree of liquidity of cecal contents were observed and recorded. Counts of E. coli in cecal contents were determined by plating serial 10-fold dilutions of weighed cecal contents on MacConkey agar supplemented with appropriate antibiotics and expressed as CFU/g. For histological examination, a fragment of cecum was fixed in 10% neutral buffered formalin, processed, cut into 5-micron sections, and stained with hematoxylin-erosin (H&E) or Giemsa (Zhu et al., 1994). Ten sequential, well-oriented, 400× fields were examined from at least two sections from each slide. Enteroadherence was graded as percent surface area covered by closely adherent bacteria (Sjogren et al., 1994 and Agin et al., 1999).

Immunization and Challenge Studies:

To determine if vaccination with the isogeneic ler mutant would provide protection, two groups of rabbits (8 in each group) were immunized with a single orogastric dose of the isogeneic ler mutant, or received PBS. Rabbits were monitored for clinical signs of disease and bacterial shedding as described above. Two weeks following immunization, serum was drawn to determine antibody titers and two rabbits in each group (preselected at random) were sacrificed for histopathological evaluation. The remaining rabbits (6/group) were challenged with the parent WT E22N (FIGS. 13A-13D). Rabbits were euthanized if demanded by severe weight loss or observed for an additional eleven days prior to sacrifice.

Examination of Immune Responses.

Sera were collected from rabbits one day prior to, and two weeks post immunization. Specific serum IgG immune responses against the C-terminal 280aa portion of jS-intimin or whole bacterial cells were tested by ELISA. The maltose-binding-protein (MBP)-intimin fusion was purified as described (Agin et al., 1999). For ELISA, microtiter plates (Immulon, Dynatech) were coated with 100 µl of purified MBP-intimin fusion protein (4 µg/ml) in 50 mM bicarbonate coating buffer (pH 9.6) and dried overnight at 37° C. For the whole bacterium ELISA, overnight-grown bacteria were suspended in the coating buffer to an optical density of 1.0 at 660 nm and diluted four times (Zhu et al., 1994). A volume of 100 µl of the diluted bacterial suspension was added to the wells of microtiter plates and dried overnight at 37° C. The ELISA procedure was performed as described (Zhu et al., 1994).

Statistical Analysis.

Values for differences in rabbit weight gain, enteroadherence (% surface area) and antibody titers between experimental groups were compared by the Student T-Test.

Nucleotide Sequence Accession Number.

The nucleotide sequence for rEPEC E22 ler (FIG. 9) and upstream region determined in this Example has been assigned GenBank accession number AF328682.

Results

Nucleotide Sequence Analysis of Ler Region of rEPEC O103.H2.

Figures 9A, 9B:
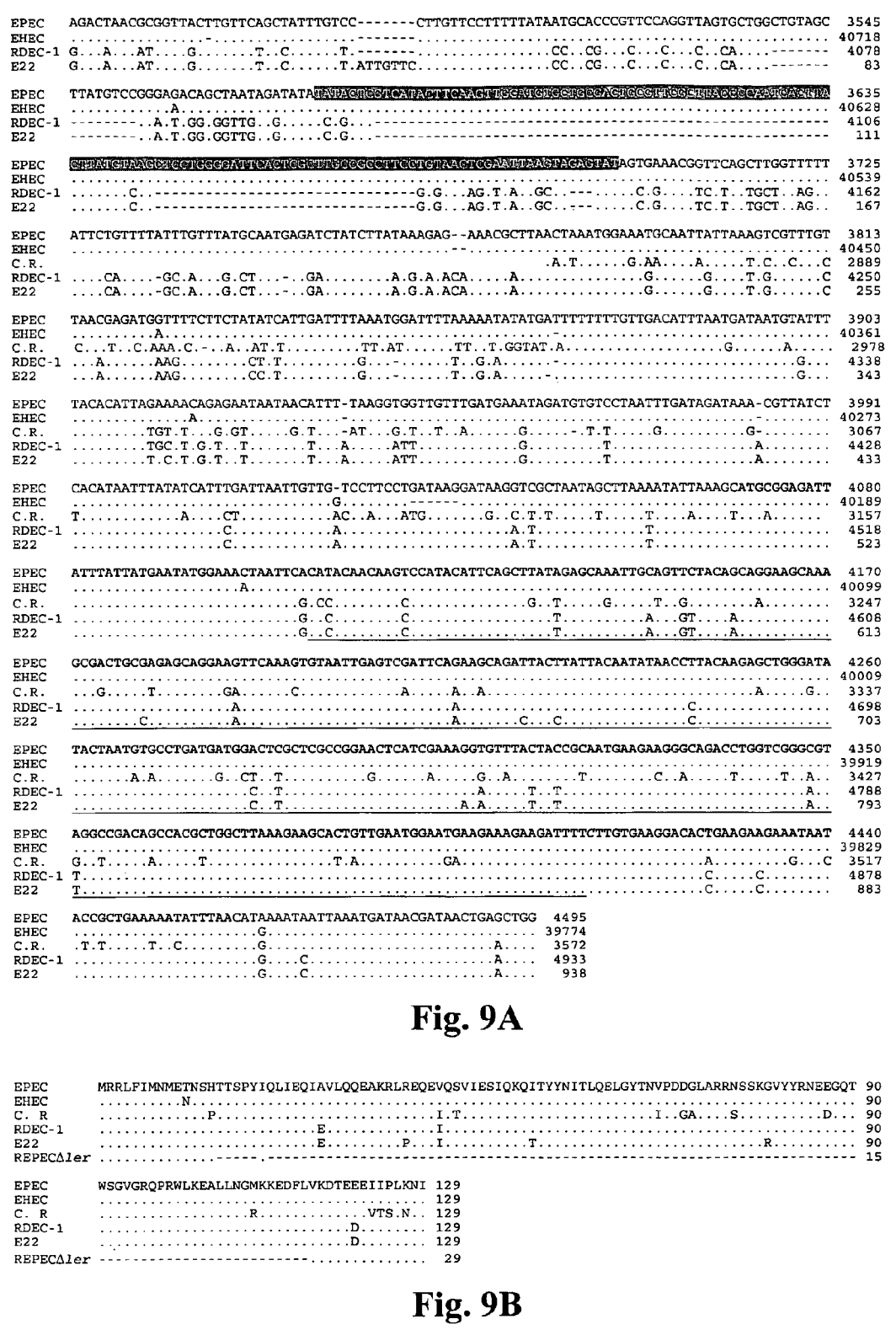

The laboratory of the present inventors demonstrated previously that proteins (Tir, intimin and Esps) encoded in the LEE of rEPEC strains RDEC-I (015:H-) and O103-.H2 share high homology (Zhu et al., 2001). However, the nucleotide sequence of the ler region of rEPEC strain E22 (O103:H2) was unknown. A DNA fragment containing the ler and its upstream region of strain E22 was obtained by PCR using primers derived from RDEC-I LEE. Direct sequencing of the 938-bp DNA PCR product showed high homology (99%) to the corresponding region of the RDEC-I LEE (4003-4933 nt, FIG. 9A). In contrast, this 938-bp DNA fragment from rEPEC O103:H2 shares 86% and 85% to the corresponding LEE regions of hEPEC (E2348/69, GenBank accession no. AF022236), and EHEC (EDL933, GenBank accession no. AF071034), respectively (FIG. 9A).

The structural ler gene of strain E22 demonstrated over 95% identity at the nucleotide level to the ler of hEPEC, EHEC, or rEPEC strain RDEC-I. However, E22 ler shares only 87% identity at the nucleotide level with the ler of C. rodentium (Deng et al., 2001). The deduced peptide sequence of Ler of rEPEC O103:H2 contains 129 residues and shares 98% identity with the RDEC-I Ler, 95% with the Lers of EPEC and EHEC (FIG. 9B).

Construction and Characterization of Ler Mutation in rEPEC O103.

A two-step SOE-PCR was used to generate a 300-bp in-frame deletion internal to the ler gene (Senanayake et al., 1995). A 1350 bp DNA fragment containing the ler deletion was cloned into pCR2.1-Topo vector to generate pECB04 9, which was used for confirmatory sequencing and subsequent cloning. Nucleotide sequencing of pECB049 indicated a 300-bp deletion in ler (from 44 to 343 nt of ler coding sequence) corresponding to 4551-4850 nt of the RDEC-I LEE (Zhu et al., 2001) without alteration of the remaining sequences (FIG. 9A). Thus, a deletion of 100 aa (from aa 15 to 114) was generated in the Ler central region (FIG. 9B).

The ler deletion mutation was subsequently introduced into the strain E22 chromosome by site-directed mutagenesis (Donnenberg et al., 1991). Colonies obtained following selection on LB plates supplemented with 5% sucrose were verified for ler mutation by PCR using two pairs of primers, B650f/B649r or B650f/B810r (Table 3). PCR amplification using primers B650f and B649r yielded a 1650-bp fragment for the intact ler from the WT parent strain E22 or a 1350-bp fragment for the mutated ler. Whereas PCR using primers B650f and B810r yielded a fragment of 778 bp for the intact ler, no amplification product for the ler mutant was seen because primer B810r is derived from the sequences internal to the deleted ler fragment. One such ler mutant strain designated as E22ΔJer, was selected for further characterization.

Effect of Ler Mutation on the Production of Bacterial Secreted Proteins.

Figure 10:
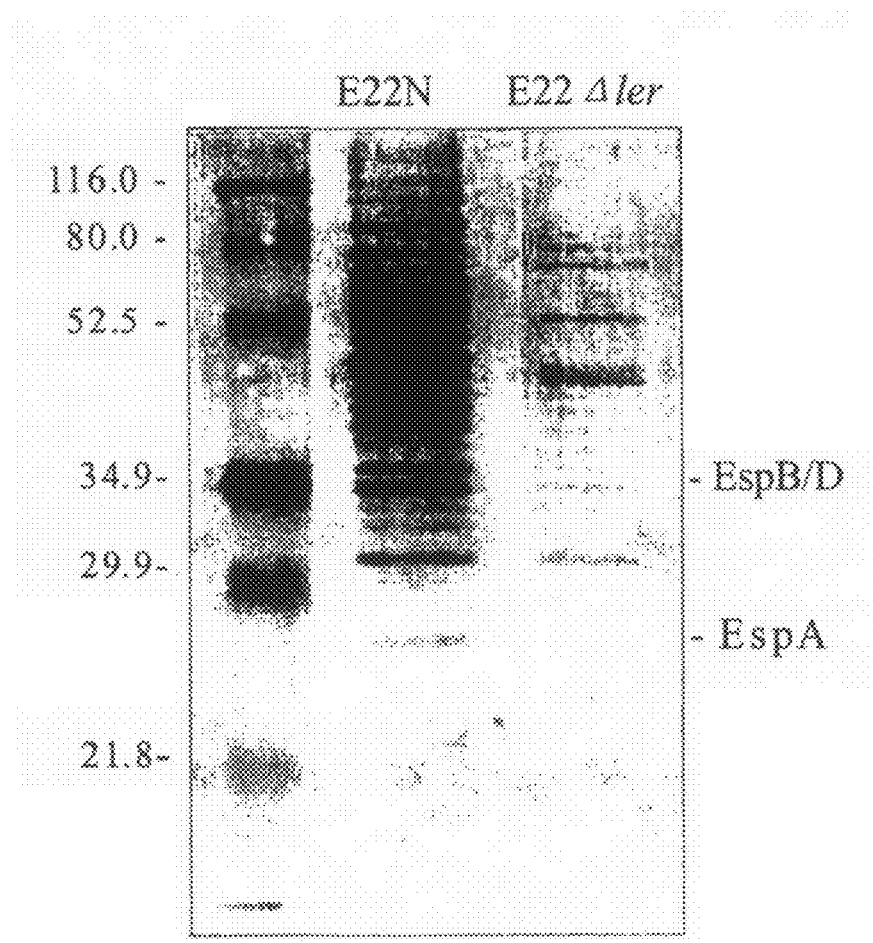
FIG. 10 is a gel showing secreted protein profiles of WT rEPEC (E22) and its derivative mutant E22Δler. Proteins were separated by 12% SDS-PAGE and visualized by silver staining. The positions of protein standards (in kDa) are indicated on the left.

As previously described for EPEC, disruption of Ler markedly abrogated the secretion of LEE-encoded proteins (Mellies et al., 1999). To investigate the role of Ler of rEPEC, secreted protein profiles of WT E22N and its derivative E22Δler were compared using standardized culture supernatants. Silver staining (FIG. 10) of SDS-PAGE-separated proteins from strain E22N revealed at least twenty-four protein bands including EspB/D and EspA. The secreted protein profile for E22Δ2er demonstrated markedly decreased expression of the majority of these bands including the LEE-encoded EspB/D and EspA, as identified by their relative molecular mass. These results for the LEE-encoded secreted proteins are in accordance with the findings of Elliott et al. and Mellies et al. (Elliott et al., 2000 and Mellies et al., 1999).

Effect of ler Mutation on In Vivo Virulence.

The level of in vivo virulence of the WT E22N and its isogeneic ler mutant E22Δler was compared. Following inoculation with $6 \times 10^5$ E22N large numbers of NaI-resistant E. coli were shed in stools (Fig. HA) such that confluent growth was observed within three days post inoculation. Loss of body weight began within 48 h and continued until sacrifice (Fig. HB). The average body weight loss was over 180 g (Fig. 11B) such that all the animals required euthanasia by day five post inoculation (Fig. 11C). One rabbit required euthanasia on day 3, three on day 4, and the remaining two on day 5. Although rabbits inoculated with E22N remained clinically normal for 24 h post inoculation, by day 2, two thirds of the rabbits had soft stools or watery diarrhea. Subsequently, all rabbits developed severe clinical illness characterized by severe diarrhea with weight loss requiring euthanasia (Table 4). At necropsy, severe colonic and cecal edema and liquid cecal contents were seen. Bacterial counts of WT rEPEC in cecal contents averaged $4 \times 10^9$ CFU per gram (range from $3 \times 10^8$ to $1 \times 10^{10}$). Microscopic examination confirmed cecal submucosal edema and demonstrated extensive focal lesions with mucosally adherent bacteria covering approximately 50% of the mucosal surface (FIG. 12A). Extensive bacterial attachment to the intestinal mucosa was associated with severe effacement of the apical surface and distortion of the architecture of the epithelial cells (FIG. 12A). This light microscopic appearance is characteristic of A/E lesions (Marches et al., 2001). These lesions were seen in all animals receiving the WT strain (Table 4). These results are consistent with previous reports that the WT parent rEPEC strain cause high morbidity and mortality in weaned rabbits (Marches et al., 2001).

Single Dose Vaccination with E22ΔLer Protects Rabbits from Challenge with Virulent Parent Strain.

It was next determined if vaccination with the attenuated E22Δ2er would induce immune responses and protect rabbits from lethal challenge with the virulent WT. All rabbits (8 per group) orogastrically inoculated with either a single dose of $1 \times 10^8$ E22Δ2er or PBS appeared normal following immunization. They consistently gained body weight and discharged normal stools. Fecal shedding of NaI-resistant bacteria was observed for all rabbits receiving E22Δ2er but not for rabbits receiving PBS (data not shown). Examination of tissues from two E22Δ2er or PBS-inoculated rabbits sacrificed two weeks post immunization revealed no abnormalities. These data confirmed with the initial study in the laboratory of the present inventors that E22Δ2er is well tolerated in rabbits.

Figure 13A:
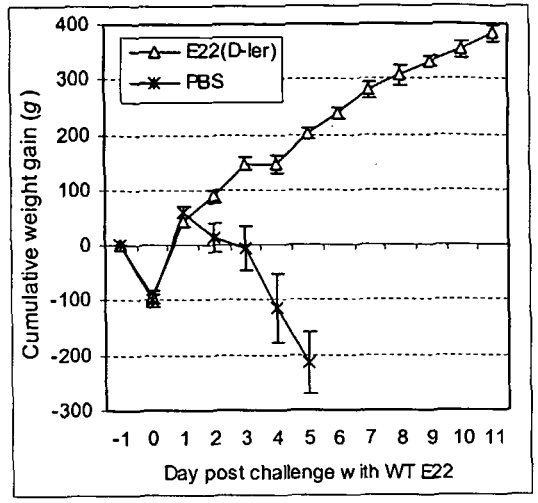
Figure 13B:
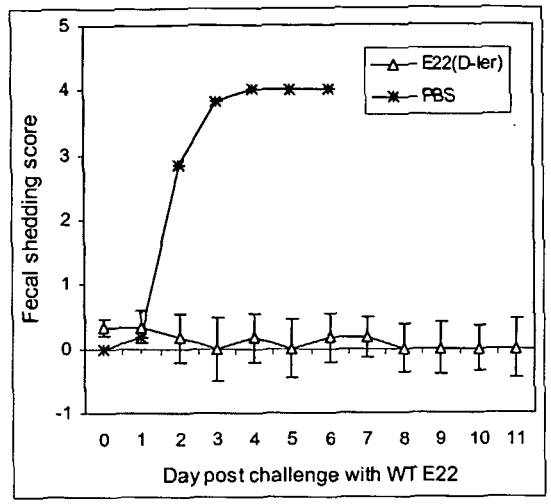
Figure 13C:
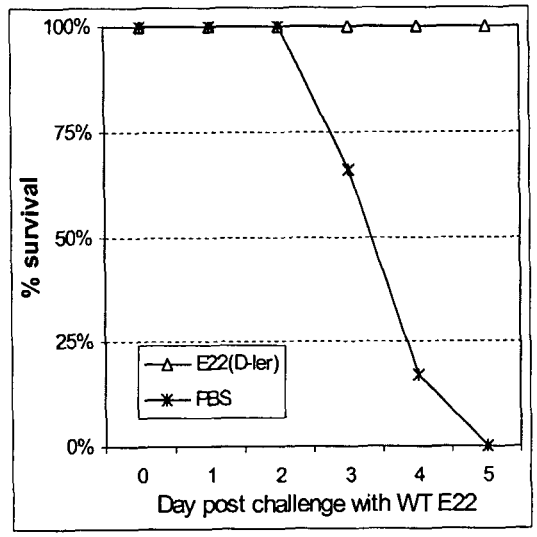

Following challenge with $2 \times 10^5$ WT E22 two weeks post immunization, E22Δle:r-vaccinated rabbits continued to gain weight with an average of 32 g/day (FIG. 13A, Table 4). Only low level fecal bacterial shedding of the challenge strain was observed in these rabbits (FIG. 13B). All immunized animals remained clinically normal without evidence of diarrhea, and all survived until being sacrificed at day eleven post challenge (FIG. 13C).

TABLE 4

Summary of clinical presentations and pathognomonic A/E lesions observed among experimentally inoculated rabbits

| Inoculation Strain (dose, CFU) | Challenge strain (dose, CFU) | Cumulative weight gain or loss (g) [b] | No. of rabbits with diarrhea [a]/ total rabbits (%) | No. of rabbits showing A/E lesions [c]/total no. examined (%) |
|---|---|---|---|---|
| Pathogenicity study: | | | | |
| E22N ($6 \times 10^5$) | N/A | $-217 \pm 57$ [d] | 6/6 (100%) | 6/6 (100%) |
| E22Δ/er($1 \times 10^8$) | N/A | $168 \pm 16$ [e] | 0/6 (0%) | 0/6 (0%) |
| Protection study: | | | | |
| E22Δ/er($1 \times 10^8$) | E22N ($2 \times 10^5$) | $382 \pm 14$ [e] | 0/6 (0%) | 0/6 (0%) |
| PBS | E22N ($2 \times 10^5$) | $-213 \pm 54$ [f] | 6/6 (100%) | 6/6 (100%) |

[a] Watery or bloody diarrhea
[b] Cumulative weight gain (+) or loss (−) post inoculation. Mean ± standard errors
[c] As determined by light microscopy
[d] Rabbits sacrificed 3-5 days post challenge
[e] Rabbits sacrificed 11 days post challenge
N/A, not applicable Following inoculation with $1 \times 10^8$ E22Δ2er rabbits shed the inoculated bacteria from the second day post inoculation to the end of the observation period (Fig. 11A). All six rabbits remained clinically normal showing normal rates (35 g/day) of weight gain (Fig. 11B) and normal stool consistency. Rabbits inoculated with E22Δler were then sacrificed five days post inoculation in order to permit comparison with rabbits inoculated with WT strain. Intestinal tissues, from ileum to distal colon, of all rabbits inoculated with E22Δ2er remained grossly normal. Bacterial counts of E22Δler in cecal contents averaged $3 \times 10^5$ CFU per gram (range from $1 \times 10^4$ to $1 \times 10^6$). Microscopically, the brush border appeared intact and deformation of intestinal mucosal architecture was not observed in the cecum. Small, scattered bacterial clusters were occasionally observed associated with normal brush borders resulting in an estimate of only 0.18% (p<0.0027 vs. WT) of the surface of the cecum covered by non-intimately adhering bacteria (FIG. 12B). This association was clearly distinct from the intimate adherence pattern exhibited by the WT parent E22N (FIG. 12A). This initial comparison clearly shows the diminished virulence of E22Δler.

All rabbits in the non-immunized PBS group began to lose weight on the second day post challenge and lost an average of 43 g/day until sacrifice (FIG. 13A). These animals all shed high levels of E22N by day 2 following challenge (FIG. 13B). Two days post-challenge, all rabbits in the PBS control group shed soft stools and subsequently all developed watery or bloody diarrhea. Severe diarrhea and loss of body weight necessitated sacrifice of these rabbits at day 5 as in our initial study.

The bacterial challenge strain was recovered from the cecal contents of all PBS control rabbits (ranging from $1 \times 10^7$ to $1.6 \times 10^8$), but from only one rabbit receiving E22Δ2er (data not shown). Microscopically, cecal tissues from E22Δler-immunized or PBS group rabbits collected before challenge, and from all E22Δ2er-immunized rabbits following challenge, revealed no adherent bacteria (Table 4). The brush borders appeared intact and deformation of intestinal mucosal architecture was not seen. In contrast, PBS control rabbits challenged with WT E22 developed cecal submucosal edema and demonstrated extensive focal lesions with bacteria intimately adherent to the mucosa following challenge with the WT parent strain (Table 4). The severe diarrhea and extensive A/E lesions observed in PBS control rabbits are consistent with the pathogenicity study and with previous reports from the laboratory of the present inventors that the WT E22 is highly virulent (Marches et al., 2001).

Detection of Immunoglobulin Specific to Bacterial Surface Antigens and to Intimin.

Figure 13D:
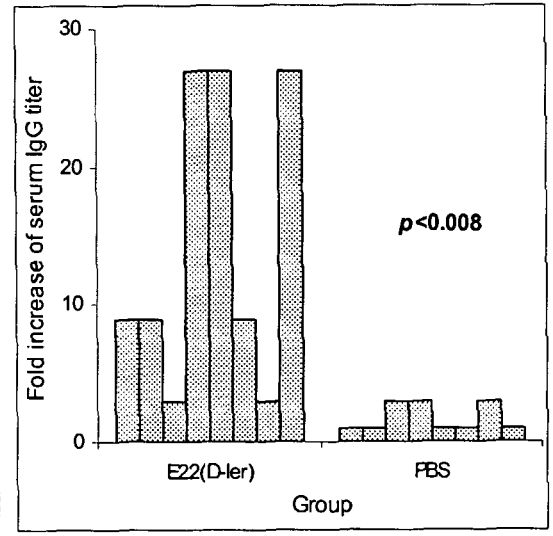

Antibodies present in sera were measured by ELISA using the whole bacterial and purified MBP-intimin (FIG. 13D). Rabbits immunized with E22Δler exhibited three to twenty-seven fold increases of serum IgG specific to bacterial surface antigens expressed on whole cells of E22. In contrast to the positive results for antibodies to whole bacteria, rises in serum antibody titer specific to the C-terminal domain of β-intimin was not observed among rabbits immunized with E22Δ2er or receiving PBS (data not shown).

Discussion

In the current study in this Example, the characterization of a defined ler mutant of rEPEC and evaluation of such isogeneic ler mutant as vaccine candidate are reported. Inactivation of Ler decreases secretion of LEE-encoded proteins. More importantly, it was demonstrated here that the in frame deletion mutation in the ler gene abolishes the in vivo capacity of rEPEC to cause disease in rabbits. This is the first in vivo demonstration of the effect of a Ler mutation of an A/E E. coli strain.

Ler belongs to the H—NS family of DNA-binding proteins that play a crucial role in the global gene regulation of enteric bacteria (Mellies et al., 1999). Although H—NS does not exhibit a high DNA sequence specificity, a number of H—NS-responsive promoters have been shown to contain regions of intrinsic DNA curvature located either upstream or downstream of the transcription start point (Rimsky et al., 2001). Bustamante et al showed that Ler acts as an antirepressor protein that overcomes the H—NS-mediated repression of LEE-encoded genes (Bustamante et al., 2001). To accomplish this, Ler displaces H—NS bound to a DNA fragment upstream of LEE operons thereby-increasing transcriptional activity (Haack et al., 2003 and Sanchez-Sanmartin et al., 2001). Thus, inactivation of Ler promotes down-regulation of LEE-encoded virulence factors by H—NS, resulting in diminished TTSS-secreted effector proteins as observed in the current study. Similarly, an in-frame non-polar deletion mutation in the ler decreased protein secretion, altered the profile of secreted proteins, and strongly diminished adherence to cultured HEp-2 cells (Mellies et al., 1999).

In the current study, the reduction in the density of secreted LEE-encoded proteins together with the disappearance of several other secreted protein bands in the ler mutant was observed. This suggests that Ler has profound regulatory effects which may alter the expression of the genes encoded on the LEE and outside the LEE. In hEPEC, Ler activates the expression of espC (encoding an autotransportor/enterotoxin) contained within a second PAI (Elliott et al., 2000). In human EHEC inactivation of ler upregulated some fimbrial gene expression (Elliott et al., 2000 and Ogierman et al., 2000).

The in vivo study here demonstrated that inactivation of Ler prevents rEPEC from adhering intimately to the rabbit intestinal mucosa in vivo. Animals receiving the ler mutant demonstrated no clinical evidence of disease even though the experimental inoculation of the mutant dose was over two logs greater than the WT. These results indicate a profound effect of the Ler in up-regulating in vivo virulence. These in vitro results are in full agreement with previous studies that Ler is essential for in vivo intimate A/E adherence. In a naturally occurring ler mutant of an O157:H-EHEC with a single base substitution resulting in a change of H $e_{57}$ to Thr, the adherence of bacteria to HEp-2 cells was significantly reduced (Ogierman et al., 2000). Furthermore, a ler mutant of murine A/E pathogen C. rodentium failed to induce A/E lesions in mice (Deng et al., 2004). Taken together, these results suggest a common mechanism of LEE-encoded virulence gene regulation by Ler among hEPEC, EHEC, C. rodentium and rEPEC (Elliott et al., 1998; Perna et al., 1998; and Deng et al., 2001).

It is well known that the specific binding of intimin and Tir play a key role in the formation of A/E lesions by A/E organisms. However, additional chromosomal and plasmid factors may serve as accessory factors in the mechanism of infection. rEPEC O103:H2 expresses the chromosomally encoded adhesive factor/rabbit 2 (AF/R2), which is a member of K88 adhesin family (Fiederling et al., 1997), and distinct from the adhesin AF/R1 found in the rEPEC 015:H-strain RDEC-I (Cantey et al., 1999 and Wolf et al., 1988 and 1990). Moreover, another plasmid-encoded rEPEC adherence locus (ral) has been identified in rEPEC strain 83/39 (O15:H-) (Adams et al., 1997). Although the isogeneic ler mutant of rEPEC has lost the ability, present in the WT, to adhere intimately to rabbit intestinal mucosa and induce effacement of microvilli, it is nevertheless able to colonize the rabbit intestine and shed at a measurable level for 10 days indicating that there may have been some in vivo replication resulting in their prolonged persistence. Since inactivation of Ler has markedly decreased the expression of virulence factors involved in intimate bacterial attachment, the observed prolonged bacterial persistence is likely independent of Tir interaction with intimin. This suggests that in the ler mutant there may be an upregulation of expression of additional accessory molecules which may facilitate colonization by bacterial attachment to the intestinal mucosa or other mechanisms (Nataro et al., 1998 and Elliott et al., 1997)

The immunization studies in this Example indicate that the defined isogeneic ler mutant of rEPEC is immunogenic after a single dose immunization. The significant increase in serum IgG titers directed to the whole bacterial cells in E22Δler vaccinated rabbits, but not in rabbits receiving PBS, suggests that the mucosal delivery of the attenuated rEPEC ler mutant induces host immune responses which protected rabbits from the lethal effects of the WT virulent strain. Because inactivation of Ler resulted in decreased production of proteins encoded on the LEE, including intimin, it is not unexpected that no antibody titers specific to intimin was detected. It is likely that the target of the immunization strategy in this study was bacterial-associated antigens independent of the LEE such as serogroup-specific lipopolysaccharide.

Previous studies on vaccination against AEEC organisms involved the inactivation of the eae or tir genes of hEPEC (Donnenberg et al., 1993) EHEC (Donnenberg et al., 1993), rEPEC O103:H2 (Marches et al., 2001), or C. rodentium (Ghaem-Maghami et al., 2001). As specific binding between intimin and Tir plays a key role in the intimate attachment of A/E organisms to host cells, inactivation of either intimin, or Tir, or both, attenuated in vivo virulence of these vaccine candidates. However, since multifactorial determinants are involved in the mechanisms of A/E infection, full attenuation may not be achieved by inactivation of intimin and/or Tir. For example, an eae mutant of hEPEC still caused diarrhea in 4 of 11 volunteer individuals, compared to 11 of 11 who ingested the WT (Donnenberg et al., 1993). Many rEPEC strains, including E22 (O103:H2), also express the novel effector Cif (for cycle inhibiting factor), which blocks the cell cycle $G_2$ to M transition, and induces the formation of stress fibers through the recruitment of focal adhesions (Bustamante et al.

2001). Although it is not encoded in the LEE, Cif is a type III effector (Marches et al., 2003). Thus, full attenuation of A/E organisms may require inactivation of additional virulence determinants. In this study, we targeted the global regulator ler in order to down-regulate not only intimin and tir, but also the TTSS and secreted proteins so that such mutants have diminished capacity to inject bacterial proteins into the host cells. Compared to the eae/tir mutants previously studied, a ler mutant may provide a safer vaccine candidate. On the other hand, inactivation of Ler might be expected to provide more limited protective immunity because of the diminished production of virulence-associated proteins encoded on the LEE or other TTSS-secreted proteins encoded out side the LEE. These virulence proteins may be required to elicit cross protective immunity to infections caused by A/E organisms of differing serotype.

Example 3

Live, Attenuated Bacterial Vaccine Against Shiga Toxin-Producing Enterohemorrhagic *Escherichia coli* (STEC/EHEC) for Cattle The present inventors are developing live attenuated bacteria for use as vaccines against Shiga toxin-producing *E. coli* (STEC), also known as enterohemorrhagic *E. coli* (EHEC), in cattle. The approach is to construct isogeneic double mutants targeting both the stx and the eae, ler or tir genes to fully attenuate STEC/EHEC. Along with the mutation to inactivate the Shiga toxin gene to abolish production of the Shiga toxin, inactivation of Ler (locus of enterocyte effacement-encoded regulator) and/or modification of the translocated intimin receptor would sufficiently attenuate bacterial virulence but retain good immunogenicity. Thus, defined isogeneic mutants will be constructed among STEC strains representing the most prevalent serogroups 0157, 026, and 0111.

General Materials and Methods and Experimental Systems

Bacterial Strains:

STEC strains (Table 5) are selected with maximum available phenotypic and genotypic information to ensure obtaining the desired results. The primary 0157:H7 strain to be used for construction of vaccine candidate will be strain 86-24 (0157:H7) which was isolated from a case of HUS in Walla Walla, Wash. EHEC 86-24 is a Streptomycin (Str)-resistant Stx2-producing strain, which has been well characterized for its virulence mechanisms and genetic background and used in a variety of animal models of pigs, cattle, and sheep (Donnenberg et al., 1993b; Sperandio et al., 2001; Torres et al., 2003; and Tzipori et al., 1995). Strain 86-24 carries the long polar (LP) fimbria homologue which has been shown to participate in the interaction of *E. coli* 0157:H7 with eukaryotic cells by assisting in microcolony formation (Stevens et al., 2002 and Torres et al., 2003). The eae mutant of 86-24 was deficient in inducing F-actin accumulation in HEp-2 cells and was incapable of attaching intimately to colonic epithelial cells in a newborn piglet model of infection (Donnenberg et al., 1993b). In one-week-old calves, 86-24 was shed in the feces for a mean of 30 days (Sanderson et al., 1999). STEC strains belonging to 026 and 0111 were human isolates. The prevalence of these strains in STEC outbreaks has been increasingly recognized (Bopp et al., 1987). STEC 026 strain was isolated from human HC. It carries Stx2-converting phage and the LEE pathogenicity island (Marques et al., 1986 and Zhu et al., 2001). The laboratory of the present inventors have previously demonstrated high homology of eae gene between STEC 026 strains and REPEC strain RDEC-I (Zhu et al., 2001). However, STEC 026 strain 08566 appears to carry γ-type intimin of STEC 0157:H7 (strain EDL933) and demonstrated adherence to HEp-2 cells in a localized manner and were positive by the fluorescence actin staining (FAS) test that is considered to correlate with the ability to cause attaching and effacing lesions in vivo (Scotland et al., 1990). STEC strain E45035, serotype 0111:H-, was isolated from the feces of a patient with HUS and it carries eae and stx1, but not stx2 (Willshaw et al., 1992). Strain E45035 is able to adhere to cultured cells and to colonize and persist in the intestinal tract of calves (Nicholls et al., 2000 and Stevens et al., 2002). The strains are obtained from the STEC Center at the National Food Safety and Toxicology Center at Michigan State University (shigatox.net/stec). The STEC Center is designed to facilitate research on STEC by providing a standard reference collection of well-characterized strains and a central on-line accessible database.

TABLE 5

List of strains

| Strain | Serotype | Origin snd relevant features |
|---|---|---|
| 86-24 | O157:H7 | Human, Stx2, γ-intimin |
| 08566 | O26 | Human, Stx2 |
| E45035 | O111:H- | Stx1, γ-intimin |

Genetic Methods:

It is desirable that the vaccines strains contain no antibiotic resistant marker. Therefore, deletion mutations will be constructed by single-overlap extension PCR(SOE PCR) as illustrated in FIG. 14. In this technique, primers derived from the targeted gene(s) are designed for desired deletion mutation. Primers B and C contain a 20-bp stretch complementary to each other. SOE-PCR is a simple two-step PCR technique for generating deletions of a wide range of sizes. This technique was used to generate deletion mutations of up to 8,000 base pairs in the HfA gene in RDEC-I. In the first step PCR amplification, PCR SUPERMIX high fidelity mixture (Invitrogen, Carlsbad, Calif.) will be mixed with template DNA (bacterial suspension in distilled water, 94° C. for 10 min) and the primers (A and B for 5'-fragment, or C and D for 3'-fragment), while amplification is performed on the PTC-200 DNA Engine (MJ Research Inc., Waltham, Mass.) using the following protocol: 33 amplification cycles of denaturation at 94° C. for 60 s, primer annealing at 55° C. for 60 s, and elongation at 72° C. for 90 s, followed by a final extension step at 72° C. for 10 min. The entire reaction mixture will then be analyzed by agarose gel electrophoresis and the DNA bands excised and purified. PCR amplicons from the above two separate PCR reactions will then be used as DNA templates for the second PCR amplification using primers A and D to achieve assembly. The resultant PCR product containing an internal deletion will be purified and subsequently cloned into pCR2.1-TOPO vector (Invitrogen, Carlsbad, Calif.). The resultant plasmid will be prepared and sent for automated sequencing. The plasmid containing the desired deletion mutation will be digested with Sac I and Xba I endonucleases and the DNA fragment containing the mutated gene will then be cloned into suicide plasmid pCVD442 (Donnenberg et al., 1991) digested with Sac I and Xba I. The plasmid pCVD442 will be transformed into *E. coli* SY327 (λpir), which contains the pir gene necessary for replication of plasmid pCVD442. Plasmid from *B. coli* SY327 will be prepared and subsequently transformed into strain SMlO (λpir) which contains the conjugal functions of plasmid pCVD442 so that the plasmid can be transferred to the recipient strain for mutagenesis. Conjugation between the recipient WT STEC and the donor SMlO (pCVD442::Δxgene) will be performed to achieve the desired defined mutation (Donnenberg et al., 1991). To verify the desired mutation, primers (A and B) overlapping the entire deletion are used in PCR amplification and the amplicon size is compared between the WT and the mutant strains. Additional primer (E) derived from the deleted fragments will be used in PCR at the same time. Thus, PCR amplification using primers A and E will yield a product for the WT but no PCR product for the mutant. All these mutants are in-frame and non-polar.

Preparation and Examination of Outer Membrane Proteins.

Bacterial outer membrane proteins (OMP) will be examined to determine the molecular weight shift of intimin and compare between the WT and isogenic eae mutant. OMP will be prepared by the method as previously described (Zhu et al., 1995). Briefly, bacterial cells will be lysed by two passages through a French press cell. The cytoplasmic membrane proteins will be solubilized with 1.67% N-lauroylsarcosine, followed by centrifugation at 200,000×g for 90 min. The protein content of the resuspended pellet containing bacterial OMPs will be determined by the Micro BCA protein assay reagent. The OMP pellet will then be examined by sodium dodecyl sulfate-polyacrylamide gel electrophoresis (SDS-PAGE) using a discontinuous buffer system by the method of Laemmli in a mini-gel apparatus. Separated protein bands will be viewed by Commassie Blue™ staining (Zhu et al., 1995).

Preparation and Examination of Secreted Proteins.

The level of secreted protein production by the isogenic ler mutants will be determined by examination of secreted proteins. Bacterial secreted proteins will be prepared from overnight culture in DMEM containing 5% fetal bovine serum. After removal of bacteria by centrifugation at 4° C. phenylmethylsulfonyl fluoride will be added to the supernatants to a final concentration of 1 mM (Zhu et al., 1995). Supernatants will then be concentrated using a Filtron Stirred Cell with MW cutoff of 3-kDa (Filtron Technology Corporation, MA). The concentrated proteins will be suspended in PBS to a final volume of 1 ml. A total of 20 ul of such a preparation was separated by SDS-PAGE on 12% gel system and protein bands will be visualized by Commassiae Blue™ staining (Zhu et al., 1995).

In Vitro Bacterial Adhesion to Epithelial Cells.

For both qualitative and quantitative adhesion assays, STEC strains and their isogeneic mutants will be evaluated for their ability to adhere to HeLa or CHO (for STEC strain 0111) cell monolayers as described (Torres et al., 2002). Cells are seeded at $1\times10^5$ cells/ml to yield a semi-confluent cell monolayer. Bacterial strains are grown in LB broth overnight at 37° C. and added to tissue culture cells replenished with fresh DMEM at a concentration of $10^7$ bacteria per well for 3 or 6 h at 37° C. Then the cell monolayers are washed, fixed and stained with Giemsa and viewed by light microscopy, or bacteria are recovered with 0.1% Triton X-100™ in PBS and plated on LB agar or MacConkey agar plates containing proper antibiotic for quantification. Data are expressed as the percentage of the original inoculums recovered from duplicate wells and are the mean of at least three separate experiments. A modified protocol that can be used for the HeLa cell adherence assay is as follows below:

HeLa Cell Adherence Assay

Day 1
  Pour 1 ml of a HeLa cell suspension ($1\times10^5$ cell/ml) into 24-well plates containing cover slips)
  Culture bacteria (including positive and negative controls) in LB containing appropriate antibiotics at 37° C. O/N Day 2
  Wash all wells 3× with antibiotic-free DMEM media
  Add 1 ml complete media (DMEM containing 10% FBS and appropriate antibiotics, 1% mannose)
  Add 20 ul of each O/N culture bacteria to respective well (duplicate or triplicate the sample)
  Swirl to mix
  Incubate for 3 h in 5% CO2
  Take off media, add fresh media containing appropriate antibiotics
  Incubate for additional 3 h
  Wash cells 4× with PBS to remove non-adherent bacteria (For bacteria counting, lyse the cell with 200 ul 0.1% Triton-100™ in PBS, count bacteria by limited dilution, data are expressed as the percentage of the original inocula recovered from triplicate wells)
  Fix cells with methanol for 5 min at RT/pour off
  Stain with 10% Giemsa stain for 15 min at RT/pour off
  Rinse wells with $dH_2O$ until clear (5-6 times)
  Leave the last $dH_2O$ in the wells
  Remove coverslips using tweezers (be careful to remove the coverslips)
  Place on copy of grid to dry (air dry or use hair drier)
  When dry label slides
  Fix coverslips to slides using clear nail polish
  Let dry/read slides and record assay.

Stx Assay.

Shiga toxin production by the WT STEC and their isogeneic mutants will be tested by cytotoxicity assay as described (Bitzan et al., 2003). Bacterial whole lysates will be prepared from overnight cultures of STEC strains and their isogenic mutants by two passages through a French Press. Protein content of extracts will be determined by using BCA Protein Assay in a 96 microwell plate (BioRad). Confluent cells (Vero, or HeLa) in 96-well plates will be grown in the presence of serial-diluted toxin preparations for 48 h. Quantitative cytotoxicity will be determined by crystal violet staining (Bitzan et al., 2003). Specifically, the protocol for the Stx assay is as follows below:

Stx Assay

Preparation of Bacterial Cell Lysates:
  1. Bacteria for analysis will include EHEC wild type and their isogenic mutants.
  2. Grow bacteria in 5O mls of Penassay Broth overnight at 37° C.
  3. Harvest bacteria by centrifugation at 5,000 RPM for 15 minutes. Remove supernatant and weigh wet pellets.
  4. Spin supernatant at 5,000 RPM followed by passage through a 0.2 micron filter to sterilize. Keep samples refrigerated at 4 degrees.
  5. Wash pellet with 5 mls of PBS twice. Resuspend in PBS at a final volume of 4 mls.
  6. Disrupt bacteria by two passages through a French Press at 15,000 psi. Wash press between each sample with 70% ETOH and DI water.
  7. Weigh out 3.9 grams of each lysate sample and store the remaining material (approximately 2 mls). Ultracentrifuge the weighed lysate at 100,000 g (70,000 RPM) for 60 minutes.
  8. Determine protein content of extracts using BCA Protein Assay in 96 microwell plate.

Cytotoxicity Assay:
1. Preparation of cells (HeLa or HEp-2). Add 100 ul HeLa cells (at a concentration of $2 \times 10^5$ cells/ml) to 96-well microtiter plate.
2. Incubate at 37° C. in 5% $CO_2$ for 24 h so that they become just confluent.
3. Make serial dilution of Stx preparation (use commercial Stx as control at the same time) in complete tissue culture medium.
4. Tissue culture medium alone (toxin control) in wells of a microtiter plate and positive Stx will be used as controls
5. Incubate at 37° C. in a 5% $CO_2$ incubator.
6. Observe at 24 h and 48 h.
7. Rinse wells with PBS, aspirate all liquid. Fix cells with 70 ul of 70% methanol per well for 1 min.
8. Remove methanol. Add 70 ul of crystal violet stain for at least 20 min. Rinse microtiter plate generously with tap water until no more dye is flowing off and air-dry.
9. Elute bound stain from cells with 200 ul 50% (v/v) ethanol.
10. Read absorbance at 490 nm or 550 nm in microplate reader.

Oral and Rectal Inoculation of Mice.

Mice have been extensively used in the studies to evaluate the induction of systemic and local immunity and experimental results demonstrate that rectal immunization could be an effective new vaccination method (Kelanthous et al., 1998; Mitchell et al., 2003a; and Nakase et al., 2001). As mice model for rectal immunization provides the simplest and valuable means to assess the immunogenicity, mice will be used to examine the immunogenicity of the STEC vaccine constructs. BALB/c female mice, 4-6 wks, will be grouped as listed in Table 8. For each immunization, a single colony of STEC mutant strain will be grown in Luria-Bertani (LB) broth for 15 h at 37° C. The cultures will be diluted at 1:100 in the same medium and incubated for 4 h at 37° C. The bacteria in logarithmic growth will be harvested by centrifugation for 20 min at 2,000×g and resuspended into sterilized PBS. The bacterial concentration in the suspension will be estimated from the optical density at 600 nth and adjusted with PBS to yield approximately $5 \times 10^{10}$ CFU which will be further confirmed by plating dilutions. A 20-μl bacterial suspension will be used for immunizations, with approximately $10^9$ CFU per inoculum. For oral immunization, mice are deprived of food 2 h before and 1 h after immunization. They will be fed with 30 μl of 10% sodium bicarbonate to neutralize stomach acidity 5 min prior to immunization and then given 20 μl of inoculum. For rectal immunization, mice will be fasted for 12 h before immunization. Mice will be anesthetized by intraperitoneal injection with 100 μl (per 10 g of body weight) of both 0.2% Rompun™ in PBS (Bayer) and 10 mg of Ketavet™ (Parker Davis) per ml. Inoculum (20 μl) will be gently introduced with a yellow tip into the rectum. Mice will be positioned with the rectum facing upwards for about 45 min to reduce leakage of the inoculum.

Determination of Bacterial Numbers in Feces.

Feces from mice will be collected and suspended in PBS. The w/v ratio will be recorded as dilution factor. 10 ul of bacterial suspension will be plated on MacConkey agar containing appropriate antibiotics.

Measurement of Antigen-Specific IgG and IgA Antibodies:

Sera IgG and fecal IgA will be examined by ELISA for specific antibodies to intimin and to the whole bacteria. To prepare γ-intimin for ELISA, the coding sequence for the C-terminal portion, the last 280 amino acid, of STEC will be amplified by PCR using primers, 5'-ttctacacaaaccgcatag (SEQ ID NO: 27) and 3'-tcaaaccaaggccagcatta (SEQ ID NO:28), derived from O157:H7 LEE sequence and cloned into pBAD-topo vector. The intimin-tag fusion protein will be induced with arabinose and purified.

Blood samples will be taken from the tail veins or orbital sinus of live animals and from the portal veins of killed animals. Sera will be collected pre-inoculation and fourteen days after last inoculation. For fecal IgA, three to six pieces of freshly voided feces will be collected into 1.5-ml centrifuge tubes, frozen at −20° C., and subsequently vacuum dried in a Speed Vac Concentrator. After net dry weighs are recorded, PBS containing 5% nonfat dry milk and protease inhibitors is added to samples at a ratio of 20 ul per mg dry feces. Following extensive vortexing and centrifugation at 16,000×g for 10 min, the clear supernatants will be collected and stored for ELISA (Hopkins et al., 1995). IgA antibody in mouse intestinal secretions will be determined by the method described by Elson, et al (Edson et al., 1984). Each mouse will be placed on a 12 cm×12 cm square of galvanized wire mesh placed within a Petri dish which contains a solution of protease inhibitors (0.1 mg/ml soybean trypsin inhibitor). The lavage solution will be given intragastrically at 15 min intervals using a blunt tipped feeding needle. Thirty minutes after the last dose of lavage solution the mice are given 0.1 mg pilocarpine I/P. A discharge of intestinal contents will be collected and vortexed vigorously, then centrifuged. The supernatant will be collected with addition of PMSF (Edson et al., 2004).

ELISA will carried out as described by Zhu et al (104) with minor modifications. Briefly, microtiter plates (Immulon, Dynatech) will be coated with 100 μl of purified intimin antigens (4 μg/ml) in 50 mM bicarbonate coating buffer (pH 9.6) and dried overnight at 37° C. For the whole bacterium ELISA, overnight-grown bacteria (the eae mutant strain) will be suspended in the coating buffer to an optical density of 1.0 at 660 nm and diluted four times. A volume of 100 μl of the diluted bacterial suspension will be added to the wells of microtiter plates and dried overnight at 37° C. The plates will then be washed and blocked with 5% skimmed milk in TTSB. Sera and fecal IgA preparations at various dilutions will be added to the wells containing intimin or bacterial antigens followed by conjugated anti-mice IgG or IgA (KPL). A phosphatase substrate system (pNPP, KPL) will be added and the reaction will be stopped by addition of 0.5 M NaOH, and read at 405 nm using a microplare reader (Zhu et al., 1995).

Statistical Analysis.

Statistical significance will be determined by Student's t-test for bacterial counts and antibody titers.

Proposed Experiments

Deletion of Genes Encoding Shiga Toxin in EHEC

Stx(s) is a major virulence factor implicated in the pathogenesis of STEC. Both Stx1 and Stx2 are bacteriophage encoded. The live attenuated vaccine strains according to the present invention will be non-Stx-producers. Thus, any genes encoding Stx(s) (stx1AB and stx2AB) will be mutated in STEC 0157, 026, and 0111.

To abolish the production of Stx1 and Stx2, the Stx1 and Stx2-coding sequences, stx1A/stx1B and stx2A/stx2B will be deleted. Because immunity specific to Stx is not desired for STEC vaccine for cattle, the StxAB genes will be deleted in their entirety. A deletion mutation by single-overlap extension PCR (SOE PCR) as illustrated in FIG. 14. Primers are designed to delete the coding sequence for stx1A/Stx1B, stx2A/stx2B including the flanking sequence between A and B gene (Table 6). Thus, a 1228-bp or 1260-bp deletion will be made for stx1AB or stx2AB, respectively. Either the stx1AB or the stx2AB genes, whichever is present in a particular strain, will be deleted from all the strains. Genotypic characterization of the mutants will be performed by PCR using primers flanking the deletion region. Single copy of deleted gene will be verified further by PCR including a primer derived from the deletion fragment. To ensure the accuracy of PCR, the WT STEC will be used as a positive control and an E. coli K-12 strain will be used as a negative control.

TABLE 6

Primers used to create deletion mutations
Note: *, f-forward, r-reverse; #, primers derived sequence data

| Primer name | Strain GenBank accession # | Position | Primer Location | |
|---|---|---|---|---|
| Stx2AB | | | | |
| 2AP | EDL933 Y 10775 | 6711-6730 | aggaaggtgcgaccgtaatt | (SEQ ID NO: 29) |
| 2Br | | 7383-7364 | atacaggtgttcctttggc | (SEQ ID NO: 30) |
| 2Cf | | 7364-7383/ 8625-8644 | tgccaaaaggaacacctgtat ggcataacctgattcgtgg | (SEQ ID NO: 31) |
| 2Dr | | 9300-9281 | gtgcctggctcctctggtgt | (SEQ ID NO: 32) |
| 2Ef | | 7861-7881 | tcatatctggcgttaatgga | (SEQ ID NO: 33) |
| Stx1A | | | | |
| 1Af | EDL933 AE005442 | 5800-5819 | catcaccttctgcgacaatc | (SEQ ID NO: 34) |
| 1Br | | 6475-6466 | cttagaatagctcagtgaaa | (SEQ ID NO: 35) |
| 1Cf | | 6475-6466/ 7703-7722 | tttcactgagctattctaagattacac a atactccttg ag | (SEQ ID NO: 36) |
| IDr | | 8377-8358 | gtgctctgacacctgtatag | (SEQ ID NO: 37) |
| IEf | | 6781-6800 | tgtatattttaagtattgca | (SEQ ID NO: 38) |
| Intimin (RDEC-I) | | | | |
| eae1Af | RDEC-I AF200363 | 27201-27220 | tcccccgggggaggggcaaaagt gccagaac | (SEQ ID NO: 39) |
| eae1Br | | 27956-27937 | tttgttttcggcatcaaaat | (SEQ ID NO: 40) |
| eae1Cf | | 27956-27937/ 28197-28216 | attttgatgcc gaaaacaaagtc ga c taatttaattacatctcaaatc | (SEQ ID NO: 41) |
| eae1Dr | | 28901-28920 | tcccccgggggattcttcctgttatc gggata | (SEQ ID NO: 42) |
| eae1Ef | | 27651-27671 | ggtgataaagtgaccgtaat | (SEQ ID NO: 43) |
| Intimin (EHEC) | | | | |
| eaeAf | EDL933 AF071034 | 15781-15800 | acgccaggagttgcaggatg | (SEQ ID NO: 44) |
| eaeBr | | 16460-16480/ 16721-16740 | cctattatgctgatgctatggtcg actaattccataaccacccggc | (SEQ ID NO: 45) |
| eaeCf | | 16721-16740 | catagcatcagcataatagg | (SEQ ID NO: 46) |
| eaeDr | | 17321-17340 | ggttatattttttgatcaaa | (SEQ ID NO: 47) |
| eaeEf | | 16501-16520 | tagacatttggagtattaac | (SEQ ID NO: 48) |
| Ler | | | | |
| lerAf | EDL933 AF071034 | 39308-39327 | ttgctggactcagtgtctct | (SEQ ID NO: 49) |
| lerBr | | 39812-39793/ 40161-40142 | tgaatatggaaaataattcataac atgaaataattaaatg | (SEQ ID NO: 50) |
| IerCf | | 40142-40161 | tgaattattttccatattca | (SEQ ID NO: 51) |
| IerDr | | 40718-40699 | caggttagtgctggctgtag | (SEQ ID NO: 52) |
| lerEr | | 39981-39962 | tgcctgatgatggactcgct | (SEQ ID NO: 53) |
| Tir | | | | |
| tirAf | EDL933 AF071034 | 19292-19930 | caggcgcatcggatttaca | (SEQ ID NO: 54) |
| tirBr | | 19953-19934/ 21402-21420 | gtaaatccgatgcgcctggtcgac atatatccataatcattta | (SEQ ID NO: 55) |

TABLE 6-continued

Primers used to create deletion mutations
Note: *, f-forward, r-reverse; #, primers derived sequence data

| Primer name | Strain GenBank accession # | Position | Primer Location | |
|---|---|---|---|---|
| tirCf | | 21402-21420 | caggcgcatcggatttaca | (SEQ ID NO: 56) |
| tirDr | | 22003-22022 | ctggtgtatagcatggcctt | (SEQ ID NO: 57) |
| tirEf | | 20741-20760 | ccagataatcaaaaagttaa | (SEQ ID NO: 58) |

Fully attenuating EHEC virulence by modifying the bacterial adhesion protein intimin (encoded by the eae gene) or the translocated intimin receptor (tir), or by inactivating the regulator Ler (lex-), which up-regulates the expression of virulence genes.

The studies in Examples 1 and 2 show that mutation in the eae and ler genes attenuated bacterial virulence while retaining their immunogenicity. The eae mutant appears ideal since the truncation of the C-terminal Tir binding domain (TBD) will retain the immunodominant region of intimin and be able to induce antibody production which has been shown to be protective. Moreover, the eae truncation will not affect the expression of proteins encoded on the LEE and outside the LEE, which may enhance immune responses against EHEC. Because Ler is a central regulator for the genes encoded on the LEE, it is expected that the attenuated mutant strains will not express ler-regulated protein expression, such as Tir and other secreted proteins.

A second deletion mutation targeted on the LEE PAI (eae or ler) will be generated.

1) The eae mutation. The previously constructed eae-mutant as described in Example 1 contains one single nucleotide deletion and selection of such mutants by either PCR or by cell adherence assay is laborsome and not practical. Instead, a 228-bp deletion mutation will be generated which will eliminate the C-terminal binding domain for easier identification by PCR using primers derived from the LEE nucleotide sequence. As a result, the defined truncated intimin retains its immunogenicity while losing the functional domain (FIG. 15). The complete eae nucleotide sequence is known for EHEC strains. The primers for the generation of eae mutants are derived from STEC strain O157:H7 strain EDL933 (Table 6). For strain 08566 and E45035, the direct sequences of eae genes are not known. However, it has been shown that the intimins of STEC 026 are β-intimins. Thus, primers were designed based on RDEC-I LEE sequence and they will be used for strain 08566 (Agin et al., 1996 and Zhu et al., 2001). The β- and γ-intimins are predominant among serogroup 0111 (China et al., 1999; Tarr et al., 2002; and Zhu et al., 2001). It can only be assumed that the eae gene of strain E45035 is homologous to RDEC-I. Therefore, primers derived from RDEC-I LEE will be used to generate eae deletion mutation for 0111.

2) The ler mutation. The studies in Example 2 demonstrated that deletion mutation in ler attenuated virulence of REPEC. The same strategy will be used to generate 330-bp in the ler of STEC strains using primers derived from STEC 0157 (Table 6).

The deletion of stxAB genes (stx1AB and/or stx2AB) will make EHEC non-toxic, and inactivation of either eae or ler will abolish A/E capacity of EHEC strains. Thus, a double mutation will fully attenuate bacterial virulence and make them harmless to cattle and safe for the environment.

Although the defined deletion mutations contain no selective marker, PCR-based identification of mutants is simple and straightforward. According to the previous studies with the rabbit EPEC strain in the laboratory of the present inventors, the percentage of occurrence of desired mutants selected from LB containing sucrose can range from 2 to 8 percent. If the eae and ler genes of 026 and 0111 are divergent from EHEC 0157 or RDEC-I, the eae and ler genes and flanking sequences will be determined from strain 08566 and E45035 using PCR products and the primers for the construction of defined deletion will be designed accordingly.

The nucleotide sequences of the stx, eae, ler and tir genes and their GenBank accession numbers for various *E. coli* strains are listed in Table 7.

TABLE 7

| Stx, eae, ler and tir sequences | | |
|---|---|---|
| | SEO ID NO: | GenBank Accession no. |
| Stx1AB | 62 | AE005174 |
| Stx2AB | 63 | Y10775 |
| RDEC-I eae | 4 | AF200363 |
| EHEC 0157 eae | 59 | AF071034 |
| RDEC-I ler | 20 | AF200363 |
| EHEC 0157 ler | 16 | AF071034 |
| EPEC 0127 ler | 14 | AF022236 |
| REPEC 0103 (E22) ler | 22 | AF328682 |
| RDEC-I tir | 60 | AF200363 |
| EHEC 0157 tir | 61 | AF071034 |

Characterization of the mutants by examination of protein profiles and in vitro assays for Stx production and adherence to cultured cell lines Deletion of Stx coding sequence would make the EHEC non-Stx-productive. Truncation of the C-terminus of intimin will result in a molecular weight shift for the intimin molecule. The deduced size for the native and truncated STEC intimins are approximately 101.7-kDa and 97.0-kDa, respectively. Since post-translational modification of intimin eliminates the signal peptide of 39 aa (Zhu et al., 1995), the mature intimins of STEC or their isogeneic eae mutants are 97-kDa for WT STEC or 89-kDa for truncated intimin, respectively. Inactivation of Ler will have a profound negative effect on the LEE-encoded secreted protein. Reduced production of secreted proteins, such as EspA, espB, EspD, is expected. As intimin and other LEE-encoded proteins play a key role in bacterial adherence, inactivation of eae or ler would abolish adherence of the mutants to cultured cell surface.

1) Stx assay. Stx assay will be performed at the time the stx1AB and/or stx2b mutants are obtained.

2) Examination of intimin. OMP will be prepared and examined for STEC and their isogenic eae mutants. Intimin expressed by the WT and their isogeneic eae mutants will be compared to view the molecular weight shift of intimin.

3) Examination of secreted protein profile. Secreted protein will be prepared and examined for STEC and their isogenic ler mutants. Secreted protein profile will be compared between the WT and their isogeneic mutants.

4) Adherence assay. Bacterial adherence to cultured cells will be performed qualitatively and quantitatively for all the mutants. HeLa cells will be used for the adherence assay, except that CHO cell line will be used for STEC O111. Cells are seeded at ~1-2×10$^5$ cells/ml to yield a semi-confluent monolayer and further cultured for 3 to 6 h in the presence of bacteria and are subjected for Giemsa staining or recovered with 0.3% Triton X-100™ in PBS for numeration (Torres et al., 2003). The above in vitro characterizations of isogenic mutants are aimed to characterize the relevant phenotypes of the mutants. These experiments will provide relevant information to confirm their genotypic alternations.

Evaluation of Immunogenicity of Live, Attenuated Vaccine Strains by Experimental Oral and Intrarectal Immunization in Mice In Examples 1 and 2, it was demonstrated that protection of rabbits following immunization with attenuated isogeneic mutants is correlated with immune responses specific to pathogenic A/E organism. To test all the mutants for their immunogenicity in cattle is not practical. Studies demonstrated that STEC may induce relatively high levels of antigen-specific fecal IgA antibody (Funatogawa et al., 2002; and Nagano et al., 2003a and 2003b) and that rectal immunization could be an effective new vaccination method (Kleanthous et al., 1998; Mitchell et al., 2003a; and Nakase et al., 2001). Therefore, a mouse model is chosen to assess the immunogenicity of the vaccine candidates. STEC strains of serogroups O157, O26, or O111, containing double [ΔeaeΔstx (Ior2) AB, or ΔlerΔstx (Ior2) AB] mutations will be given to mice to evaluate immune response to bacterial LPS and/or to intimin.

1) Immunization of Mice. Groups of mice will be used for each mutant strain or vaccination route (Table 8). Sera will be collected pre-vaccination and 2 weeks after final boost (FIG. 16).

TABLE 8

Treatment groups of mice

| Group | Strain | Serotype | Genotype | No of mice. | Immunization |
|---|---|---|---|---|---|
| 1 | 86-24 | O157:H7 | ΔStx2AB/Δeae | 16 | Oral |
| 2 | | | ΔStx2AB/Δeae | 16 | Rectal |
| 3 | | | ΔStx2AB/Δler | 16 | Oral |
| 4 | | | ΔStx2AB/Δler | 16 | Rectal |
| 5 | Control | | PBS | 16 | PBS |
| 6 | 08566 | O26 | ΔStx2AB/Δeae | 16 | Oral |
| 7 | | | ΔStx2AB/Δeae | 16 | Rectal |
| 8 | | | ΔStx2AB/Δler | 8 | Oral |
| 9 | | | ΔStx2AB/Δler | 8 | Rectal |
| 10 | Control | | PBS | 16 | PBS |
| 11 | E45035 | O111:H- | ΔStx1AB/Δeae | 16 | Oral |
| 12 | | | ΔStx1AB/Δeae | 16 | Rectal |
| 13 | | | ΔStx1AB/Δler | 8 | Oral |
| 14 | | | ΔStx1AB/Δler | 8 | Rectal |
| 15 | Control | | PBS | 16 | PBS |

2) Determination of fecal bacterial shedding following vaccination. Fecal bacterial shedding will be determined once a week to monitor bacterial colonization. Bacterial suspension will be plated on MacConkey agar with appropriate antibiotics.

3) ELISA for sera IgG and fecal IgA: ELISA will be used to determine antigen-specific levels of Igs in sera and fecal samples, focusing on the immunogenicity of STEC 1157:H7 isogenic mutants. Therefore, for O157:H7 derivatives, the IgG and IgA antibodies titers specific to the whole bacteria and intimin will be determined in sera and intestinal secretion, respectively, at day 0, 14, and 28 following first immunization. Sera will be collected from the remaining mice at day 0 and day 28. IgA samples from the intestinal secretion and feces will be collected at the time of sacrifice for the remaining mice.

Challenge of Vaccinated Mice with Wild-Type EHEC to Determine the Level of Protection Once immunogenicity is determined, the optimal immunization regimen will be used in the challenge studies. Reduced bacterial shedding in feces among vaccinated mice will indicate the level of protection as described for passive administration of hyperimmune colostrums (Dean-Nystrom et al., 2002).

Challenge with a StrR, non-Shiga toxin producing O157 strain will be performed two weeks after boost immunization. Mice immunized with vaccine candidate orally or intrarectally will be challenged. To promote colonization, mice will be given drinking water that contains streptomycin for 3 days before orogastric administration of the challenge strain (as described for oral vaccination). Un-inoculated mice will be used as controls.

Feces will be collected from each mouse for ten days. Feces will be weighed and then suspended in PBS. The fecal wt/final volume ratio will represent the dilution factor. lO μl of fecal suspensions will be plated on MacConkey agar containing appropriate antibiotics. To determine bacterial numbers in cecal contents, excised cecum will be vigorously washed three times with 10-ml PBS serially diluted and plated on MacConkey (str). Mouse weight will be recorded daily.

Statistical significance will be determined by Student's t-test for bacterial counts, antibody titers and weight changes.

Example 4

In this example, an attenuated live STEC vaccine candidate deficient in cell adherence and Shiga-toxin production was constructed. Oral or rectal immunization of mice with this attenuated mutant strain induced measurable serum IgG and fecal IgA specific to O157 lipopolysacharide antigen. Following experimental challenge with an intact intimin O157:H7 strain, vaccinated mice demonstrated significant reduction of intestinal colonization when compared to the naive mice. Immunization of animals with this double mutant represents a novel and practical vaccination strategy to induce effective local mucosal immunity, thereby reducing or preventing STEC colonization in the gut.

Materials and Methods

Bacterial Strains, Plasmids, and Cultural Conditions.

Bacterial strains and plasmids are listed in Table 9. The prototype STEC 86-24 (O157:H7) was obtained from the STEC Center at the National Food Safety and Toxicology Center at Michigan State University. The laboratory *E. coli* strain DH5α was used for plasmid transformation except for suicide plasmids (pCVD442 and derivatives), which were maintained in *E. coli* SY327 or SMlO (Donnenberg, 1991). Bacterial strains were stored at −80° C. in Luria-Bertani (LB) containing 20% glycerol and grown on LB agar or LB broth or MacConkey agar. Appropriate antibiotics were added to the media when needed at the following concentrations: carbenicillin (Car), 50 μg/ml; Nalidixic acid (Nal), 50 μg/ml; Streptomycin (Str), 25 μg/ml.

TABLE 9

Strains and plasmids used in this study (Example 4)

| Strains or plasmids | Relevant characteristics | Source or reference |
|---|---|---|
| *E. coli:* | | |
| 86-24 | EHEC O157:H7, Stx2, Str$^R$ | Zhu et al., 1995 |
| SY327 | SY327 λpir, intermediate recipient for suicide vector pCVD442 | Donnenberg et al., 1991 |
| SM10 | SM10 λpir, recipient for suicide vector pCVD442 to serve as donor strain, Kan$^R$ | Donnenberg et al., 1991 |
| O157Δeae | An isogeneic eae mutant of 86-24, Str$^R$ | This study |
| 0157 AeaeAstx2'AB | An isogeneic eaeIestx2Ab mutant of 86-24, Str$^R$ | This study |
| Plasmids: | | |
| pCR2.1 Topo | PCR cloning vector | Invitrogen |
| pCVD442 | Suicide vector, Amp$^R$ | Donnenberg et al., 1991 |
| pE525 | pCR2.1::Δeαei57 | This study |
| pE538(SM10) | pCVD442::Aeael57 | This study |
| pE462 | VCR2A::Astx2AB | This study |
| pE488(SM10) | vCVO442::Astx2AB | This study |

Generation of a Defined Deletion Mutation.

Recombinant DNA techniques were performed according to standard procedures (Sambrook, 2001). The defined deletion mutations in the eae or stx2AB genes were generated by single-overlap extension PCR (SOE PCR) (Senanayake, 1995). For PCR amplification, PCR SUPERMIX high fidelity mixture (Gibco BRL, Rockville, Md.) was mixed with template DNA (86-24 bacterial suspension in distilled water, 94° C. for 10 min) and the primers, while amplification was performed on the PTC-200 DNA Engine (MJ Research Inc., Waltham, Mass.) using the following protocol: 33 amplification cycles of denaturation at 94° C. for 60 s, primer annealing at 55° C. for 60 s, and elongation at 72° C. for 90 s, followed by a final extension step at 72° C. for 10 min (Zhu, 2005a). To create the intimin truncation, a 240-bp fragment at the intimin C-terminus was deleted by PCR using primers (Table 10) derived from the eae gene of EHEC 0157:H7. The initial PCR used primers eaeAf/eaeBr or eaeCf/eaeDr, respectively. Primers eaeBr and eaeCf contain a 20 bp stretch overlapping each other. The subsequent PCR using initial PCR amplicon with the primers eaeAf/eaeDr generated a DNA fragment yielding a 240-bp deletion at the C-terminal domain of intimin. The entire coding sequence for stx2A and stx2B was deleted by SOE PCR using primers (Table 10) derived from known sequence of 0157:H7 (Perna, 2001). The initial PCR amplification used primers 2Af/2Br or 2Cf/2Dr, respectively. The subsequent PCR using 2Af/2Dr generated a DNA fragment yielding a 1241-bp deletion. The primers 2Br and 2Cf contain a 20 bp stretch overlapping each other for assembling DNA fragments obtained by initial PCR. The resultant DNA fragment harbors an internal deletion of 1,241 bp to eliminate the entire Stx2A and Stx2B coding sequences

TABLE 10

Primers used to create defined deletion mutations

| Primer | GenBank accession # | Position | Primer Location |
|---|---|---|---|
| eae | | | |
| eaeAf | AF071034 | 15781-45800 | acgccaggagttgcaggatg (SEQ ID NO: 44) |
| eaeBr | | 16460-16480/ 16721-16740 | cctattatgctgatgctatggtcg (SEQ ID NO: 45) actaattccataaccaccccggc |
| eaeCf | | 16721-16740 | catagcatcagcataatagg (SEQ ID NO: 46) |
| eaeDr | | 17321-17340 | ggttatattttttgatcaaa (SEQ ID NO: 47) |
| eaeEf | | 16501-16520 | tagacatttggagtattaac (SEQ ID NO: 48) |
| STX2AB | | | |
| 2aF* | Y10775 | 6711-6730 | aggaaggtgcgaccgtaatt (SEQ ID NO: 29) |
| 2Br | | 7383-7364 | atacaggtgttccttttggc (SEQ ID NO: 30) |
| 2Cf | | 7364-7383/ 8625-8644 | tgccaaaaggaacacctgtat (SEQ ID NO: 31) ggcataacctgattcgtgg |
| 2Dr | | 9300-9281 | gtgcctggctcctctggtgt (SEQ ID NO: 32) |
| 2Ef | | 7861-7881 | tcatatctggcgttaatgga (SEQ ID NO: 33) |
| tir | | | |
| tirAf | AF071034 | 19292-19930 | caggcgcatcggatttaca (SEQ ID NO: 54) |
| tirBr | | 19953-19934/ 21402-21420 | gtaaatccgatgcgcctggtcgac (SEQ ID NO: 55) atatatccataatcatttta |
| tirCf | | 21402-21420 | caggcgcatcggatttaca (SEQ ID NO: 56) |
| tirDr | | 22003-22022 | ctggtgtatagcatggcctt (SEQ ID NO: 57) |
| tirEf | | 20741-20760 | ccagataatcaaaaagttaa (SEQ ID NO: 58) |

Note:
*, f-forward, r-reverse; #, primers derived sequence data

The SOE PCR products for eae and stx2AB harboring defined deletion mutation were purified and subsequently cloned into cloning vector pCR2.1-TOPO (Invitrogen), which were then prepared and being sequenced. Subcloning of DNA fragments containing deleted eae or stx2AB to the suicide vector pCVD442 was performed and transformed into strain SY327 and then into SM10 as previously described (Zhu, 2005a). Conjugation between the recipient WT strain 86-24 and the donor SM10 (pCVD442:Δeae) or SM10 (pCVD442::Δstx2AB) was performed to achieve the desired defined mutation (Zhu, 2005a). To verify deletion mutations in the WT background, primers (A and D) overlapping the entire deletion and an additional primer (E) derived from within the deleted fragments were used for PCR amplification and the amplicon size was compared between the WT and the mutant strains. Thus, PCR amplification using primers A and E yielded a product for the intact genes but yielded no PCR product for the mutated genes.

In Vitro Adherence Assay.

The cell adherence assay for the WT O157:H7 and its isogeneic mutant was performed on HeLa monolayers as described (Tories, 2002; Zhu, 1994). Briefly, HeLa cells were seeded at $1 \times 10^5$ cells/ml and grown overnight to yield a semi-confluent cell monolayer. Bacterial strains were grown in LB broth overnight at 37° C. and added to tissue culture cells replenished with fresh DMEM at a concentration of 107 bacteria per well and grown at 37° C. for 3 or 6 h. The cell monolayers were then washed, fixed and either stained with Giemsa and viewed by light microscopy, or treated with 0.1% Triton X-100™ in PBS in order to lyse the cells and disperse the adherent bacteria. This cell lysate was plated on MacConkey agar plates supplemented with Str for viable bacteria counting.

Cytotoxicity Assays.

Bacterial whole lysates were prepared from overnight cultures by two passages through a French Press. The bacterial pellets were removed by centrifugation. Protein content of extracts was determined by using BCA Protein Assay (Bio-Rad) according to manufacturer's instructions. Microcytotoxicity was analyzed on HeLa cells and compared to the parent WT strain as described (Gentry, 1980). The last dilution of the sample in which 50% of the cells detached from the plate surface was considered the 50% cytotoxic dose (CD50).

Oral and Rectal Immunization of Mice.

BALB/c female mice, 4-6 week-old, were used for vaccination studies. For each immunization, a single colony of STEC mutant strain was grown in LB broth for 15 h at 37° C. The cultures were diluted at 1:100 in the same medium and incubated at 37° C. for additional 4 h to obtain logarithmic growth. The bacterial cells were harvested by centrifugation at 2,000×g for 20 min and resuspended with sterilized PBS. The bacterial concentration in the suspension was determined by optical density at 600 nm and adjusted with PBS to yield approximately $5 \times 10^{10}$ CFU/ml. The viable counts were determined by limited dilution method. A 20 µl bacterial suspension was used for vaccinations, with approximately 109 CFU per inoculum. For oral immunization, mice were deprived of food 2 h before and 1 h after vaccination. They were fed with 30 µl of 10% sodium bicarbonate to neutralize stomach acidity 5 min prior to immunization and then given 20 µl of inoculum. For rectal immunization, mice were fasted for 12 h before immunization. Mice were anesthetized by intraperitoneal injection with 100 µl (per 10 g of body weight) of both 0.2%. Rompun™ in PBS (Bayer) and 10 mg of Ketavet™ (Parker Davis) per ml. The inoculum (20 µl) was gently introduced with a yellow tip into the rectum. Mice were positioned with the rectum facing upwards for about 45 min to reduce leakage of the inoculum.

Determination of Bacterial Numbers in Feces.

Feces from mice were collected and suspended in PBS. The w/v ratio was recorded as dilution factor. 10 ul of bacterial suspension was plated on MacConkey agar supplemented with appropriate antibiotics.

Preparation of Serum and Intestinal Secretions by Wash Out.

Sera were collected pre-inoculation and fourteen or twenty-eight days after last inoculation. Blood samples were taken from portal veins of killed animals. IgA antibody in mouse intestinal secretions was prepared by the method described by Elson et al (Elson, 1984). Each mouse was placed on a 12 cm×12 cm square of galvanized wire mesh placed within a Petri dish which contained a solution of protease inhibitors (0.1 mg/ml soybean trypsin inhibitor). The lavage solution was given intragastrically at 15 min intervals using a blunt tipped feeding needle. Thirty minutes after the last dose of lavage solution the mice were given 0.1 mg pilocarpine I/P to promote peristalsis. Discharged intestinal contents were collected and vortexed vigorously, then centrifuged. The supernatant was collected with addition of PMSF.

Measurement of Antigen-Specific IgG and IgA Antibodies:

O157 LPS was prepared by the phenol extract method. Sera IgG and fecal IgA specific antibodies to O157 LPS was examined by ELISA as described (Agin, 2005; Zhu, 1995) with minor modifications. Briefly, microtiter plates (Immulon, Dynatech) were coated with 100 µl of O157 LPS (10 µg/ml) in 50 mM bicarbonate coating buffer (pH 9.6) and dried overnight at 37° C. The plates were blocked with 10% skimmed milk in PBS. Sera and IgA preparations at various dilutions were added to the wells followed by conjugated anti-mice IgG or IgA (KPL). A phosphatase substrate system (pNPP, KPL) was added and the reaction was stopped by addition of 0.5 M NaOH and read at 405 nm using a microplate reader (Zhu, 1995; 2005b).

Statistical Analysis.

Comparisons of the values for in vitro adherence, antibody titers, and neutralization titers between experimental groups were made with Student's t test. Differences were considered significant when the P value was ≤0.05.

Results

Generation of Defined Deletion Mutation in the eae and stx2AB Genes.

As previously reported, a truncated intimin mutant retains its immunogenicity and protectivity (Agin, 2005). The laboratory of the present inventors thus created an intimin mutant by deleting the C-terminal 80 aa, which is responsible for binding Tir. Initial PCR amplification using primers eaeAf/eaeBr or eaeCf/eaeD obtained amplicons of 720 or 620-bp, respectively (data not shown). Subsequent PCR using primers eaeAf/eaeDr obtained a PCR product of 1,320 bp, which was then cloned into pCR2.1-topo vector to obtain plasmid pE525. Nucleotide sequencing of the insert indicated a 240-bp deletion at the C-terminal domain of intimin without alternating the remaining flanking sequences.

By using the same strategy, a deletion of 1,241-bp was made in the stx2AB gene. The initial PCR using primers 2Af/2Br and 2Cf/2Dr obtained 673 and 696-bp, respectively, whereas subsequent PCR using primers 2Af/2Dr obtained a 1,349 bp fragment which was cloned into pCR2.1 vector to obtain plasmid pE462. Nucleotide sequencing indicated deletion of the entire coding sequence for Stx2A and Stx2B including the flanking sequence between stx2A and stx2B while the remaining sequences flanking the stx2AB remained unchanged.

The DNA fragments containing the defined deletion mutation (Δeae or Δstx2AB) were obtained from pE525 and pE462, respectively, by digesting with endonucleases Sad and Xbal and subcloned into delivery suicide plasmid pCVD442 digested with Sacl and Xbal, thus obtaining plasmids pE538 (Δeae) or pE488 (Δstx2AB). Both of these plasmids were maintained into strain SY327 and subsequently transformed into conjugative strain SMlO.

Construction of Isogenic eae and stx2AB Mutants of 0157: H7.

An isogenic eae mutant on the WT EHEC strain 86-24 background was first generated and subsequently an additional stx2AB mutation was generated. Conjugation between 86-24 and SMlO harboring suicide delivery plasmid pE53 8 containing defined eae deletion mutation yielded numerous colonies. PCR amplification using primer eaeAf/eaeDr indicated that these resultant conjugates contained both the intact and mutated eae. One conjugate was selected to grow in LB broth without selection and subsequently selected on LB containing 5% sucrose. Allelic exchange of the native eae with mutated eae was confirmed by PCR using two sets of primers (eaeAf/eaeDr, or eaeFf/eaeDr) as described (Zhu, 2005a). Primers eaeAf/eaeBr and eaeFf/eaeDr yielded respective 1,560 bp or 840 bp fragment for the intact eae, respectively, whereas yielded only a 1,320 bp fragment for the mutated eae (data not shown). One such mutant was designated as O157 Δeae which was used for further studies.

The additional stx2AB mutation was generated in a similar manner except that conjugation was made between O157_leae and SMlO harboring pE488 containing the mutated stx2AB fragment. Following selection on LB supplemented with sucrose, allelic exchange of native stx2AB by mutated stx2AB was confirmed by PCR using two sets of primers (2Af/2Dr, or 2Ff/2Dr). Primers 2Af/2Dr and 2Ff/2Dr yielded fragments of respective 2,590 bp or 1,440 bp for the intact stx2AB, whereas they yielded only 1,349 bp for the deletion-mutated stx2AB (data not shown). One such final double mutant was designated as O151ΔeaeΔstx.

Intimin Molecular Shift.

The truncation of 80 residues at the C-terminal portion of intimin was further verified. The predicted sizes for the native and truncated intimins are approximately 101.8 or 93.1-kDa, respectively. Because post-translational modification of intimin eliminates a signal peptide of 39 aa (Zhu, 1995), the mature intimins of EHEC 0157:H7 WT or its isogenic eae mutant are 97.3-kDa or 88.6-kDa, respectively. Coomassie brilliant blue staining of SDS-PAGE-separated OMP extracts from the WT 86-24 revealed an intimin protein band with estimated molecular mass of 97-kDa (Data not shown). However, this 97-kDa-protein band was absent in strain O157Z\eae and a protein band with an estimated molecular mass of 89-kDa appeared.

Adherence on HeLa Cells.

When examined on HeLa cells, O157 Δeae showed significant ($p<0.013$) reduction on bacterial adherence when compared to the WT parent strain (FIGS. 17A-18B). While the WT 86-24 form microcolonies on about 47% of cells, the isogenic eae mutant form microcolonies on only 5% of cells.

Cytotoxicity.

Cytotoxicity to HeLa cells was compared between the WT and its isogenic stx2AB mutant. While the WT strain 86-24 demonstrated a LD50 of $1.2\times10^4$/mg, the isogenic eae mutant showed nearly two log reduction of the toxicity to HeLa cells (data not shown).

Colonization of 0157ΔEaeΔStx2AB Following Vaccination.

All mice were negative for the Str-resistant *E. coli* before vaccination. Nearly all mice, vaccinated either via oral or rectal route, shed Str-resistant *E. coli* 24 h following initial inoculation of 0157 ΔeaeΔstx2AB (FIG. 19). The total viable counts in the fecal pallets reached $1\times10^9$ CFU/ml (oral vaccination) or $1\times10^9$ CFU/ml (rectal vaccination) at day six post vaccination. The pattern of fecal shedding of vaccinated bacteria was similar, since day 8 post vaccination between animals receiving the vaccine strain orally or rectally reaching $3\times10^7$ CFU/ml. PCR of random selected Str-resistant CFUs using primers for the eae (eaeAf/eaeDr) or stx2AB (2Ar/2Dr) revealed two DNA bands corresponding to the mutated eae or stx2AB genes indicating they were vaccinated 0157 ΔeaeΔstx2AB.

The pattern for fecal bacterial shedding following boost oral or rectal vaccination at day 14, either via oral or rectal route, appeared very similar too. At day 22 post vaccination, only one mouse in the oral vaccination group shed some Str-resistant bacteria. While other mice were negative for Str-resistant bacteria, three out of seven mice shed nearly $2\times10^8$ bacteria at day 29 post vaccination. Fecal shedding was observed among two rabbits at day 25, 28, or 30 days post vaccination.

Bacteria Recovery Following Challenge with O157Δstx2AB.

Fecal shedding of challenged O157Δstκ2AB occurred the following day of challenge (FIG. 20). The mice in the naive group shed the highest numbers reaching nearly $10^{10}$ CFU/g within the first 6 days following challenge. Mice vaccinated with O151 ΔeaeΔstx2AB either by the oral or rectal route shed significantly less ($p<0.05$) of the challenge bacteria than those in naïve group. Six days following challenge, similar numbers of bacteria was recovered from all groups.

Detection of 0157 LPS-Specific IgG in Serum and IgA in Intestinal Secretion.

Mice in the oral vaccination group showed two-fold increases of serum IgG at day 28 following vaccination (FIG. 21A). The serum IgG titers at day 0, 14, and 28, in rectal vaccination were similar (FIG. 21B). Comparison of serum IgG titers at day 28 showed two fold increases among oral vaccination group over the remaining two groups (FIG. 22). IgA specific to 0157 LPS showed slight increase among oral vaccination mice over the remaining two groups (FIG. 23).

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Adams L M, Simmons C P, Rezmann L, Strugnell R A, Robins-Browne R M. Identification and characterization of a K88- and CS31A-like operon of a rabbit enteropathogenic *Escherichia-coli* strain which encodes fimbriae involved in the colonization of rabbit intestine. *Infect Immun;* 65:5222-30 (1997).

Adu-Bobie, J., Frankel, G., Bain, C, Goncalves, A. G., Trabulsi, L. R., Douce, G., Knutton, S., and Dougan, G. Detection of intimins alpha, beta, gamma, and delta, four intimin derivatives expressed by attaching and effacing microbial pathogens. *J. Clin. Microbiol.* 36:662-668 (1998).

Adu-Bobie, J., L. R. Trabulsi, M. M. Carneiro-Sampaio, G. Dougan, and G. Frankel. Identification of immunodominant regions within the C-terminal cell binding domain of intimin alpha and intimin beta from enteropathogenic *Escherichia coli. Infect. Immun.* 66:5643-5649 (1998).

Agin, T. S. and M. K. Wolf. Identification of a family of intimins common to *Escherichia coli* causing attaching-effacing lesions in rabbits, humans, and swine. *Infect. Immun.* 65:320-326 (1997).

Agin, T. S. Boedeker E. C. Johnson L. A. Thate T. E. Russell R. S. Towards a vaccine for Shiga toxin-producing *Escherichia coli* (STEC): Protection against hemorrhagic colitis in an animal model following immunization with a rabbit enteropathogenic *E. coli* (REPEC) strain expressing truncated intimin. Abstracts of the 99th Gen. Mtng. ASM (1999)

Agin, T. S., Cantey, J. R., Boedeker, E. C, and Wolf, M. K. Characterization of the eaeA gene from rabbit enteropathogenic *Escherichia coli* strain RDEC-I and comparison to other eaeA genes from bacteria that cause attaching-effacing lesions. *FEMS Microbiol. Lett.* 144:249-258 (1996)

Agin, T S, C. Zhu, L A. Johnson, T E. Thate, Z. Yang, E C. Boedeker. Protection against hemorrhagic colitis in an animal model by oral immunization with isogeneic rabbit enteropathogenic *Escherichia coli* attenuated by truncating intimin. *Infect. Immun.* 73:6608-6619 (2005).

Ahmed Z U, Sarker M R, Sack D A. Protection of adult rabbits and monkeys from lethal shigellosis by oral immunization with a thymine-requiring and temperature-sensitive mutant of *Shigella flexneri. Vaccine,* 8:153-58 (1990).

An H, Fairbrother J M, Dubreuil J D, Harel J. Cloning and characterization of the eae gene from a dog attaching and effacing *Escherichia coli* strain 4221. *FEMS Microbiol Lett,* 148:239-45 (1997).

Armstrong, G. D., P. C. Rowe, P. Goodyer, E. Orrbine, T. P. Klassen, G. Wells, A. MacKenzie, H. Lior, C. Blanchard, and F. Auclair. A phase I study of chemically synthesized verotoxin (Shiga-like toxin) Pk-trisaccharide receptors attached to chromosorb for preventing hemolytic-uremic syndrome. *J. Infect. Dis.* 171:1042-1045 (1995).

Badea, L., Doughty, S., Nicholls, L., Sloan, J., Robins-Browne, R. M., and Hartland, E. L. Contribution of Efa1/LifA to the adherence of enteropathogenic *Escherichia coli* to epithelial cells. *Microb. Pathog.* 34:205-215 (2003).

Banatvala, N., Griffin, P. M., Greene, K. D., Barrett, T. J., Bibb, W. F., Green, J. H., and Wells, J. G. The United States National Prospective Hemolytic Uremic Syndrome Study: microbiologic, serologic, clinical, and epidemiologic findings. *J. Infect. Dis.,* 183:1063-1070 (2001).

Berendson, R., C. P. Cheney, P. A. Schad, and E. C. Boedeker. Species-specific binding of purified pili (AF/R1) from the *Escherichia coli* RDEC-I to rabbit intestinal mucosa. *Gastroenterology* 85:837-845 (1983).

Bielaszewska, M., I. Clarke, M. A. Karmali, and M. Petric. Localization of intravenously administered verocytotoxins (Shiga-like toxins) 1 and 2 in rabbits immunized with homologous and heterologous toxoids and toxin subunits. *Infect Immun.* 65:2509-16 (1997).

Bitzan, M. and Karch, H. Serological methods for the detection of STEC infections. In "*E. coli* Shiga toxin methods and protocols" (D. Philpott and F. Ebel, Eds.), pp. 27-43. Human Press Inc (2003).

Blanco, J. E., Blanco, M., Alonso, M. P., Mora, A., Dahbi, G., Coira, M. A., and Blanco, J. Serotypes, virulence genes, and intimin types of Shiga toxin (verotoxin)-producing *Escherichia coli* isolates from human patients: prevalence in Lugo, Spain, from 1992 through 1999. *J. Clin. Microbiol.* 42:311-319 (2004a).

Blanco, M., Blanco, J. E., Mora, A., Dahbi, G., Alonso, M. P., Gonzalez, E. A., Bernardez, M. I., and Blanco, J. Serotypes, virulence genes, and intimin types of Shiga toxin (verotoxin)-producing *Escherichia coli* isolates from cattle in Spain and identification of a new intimin variant gene (eae-xi). *J. Clin. Microbiol.* 42:645-651 (2004a).

Blanc-Potard A B, Solomon F, Kayser J, Groisman E A. The SPI-3 pathogenicity island of *Salmonella enterica. J. Bacteriol.* 81:998-1004 (1999).

Black et al., *J. infect. Dis.,* 155:1260-1265 (1987)

Boedeker E C, Cheney C P. Infection of rabbits with *E. coli* strain RDEC-I: a model for infections of human infants with enteropathogenic *E. coli* (EPEC) strains. In C. J. Pfeiffer (ed.), Animal Models of Intestinal Disease. Boca Raton: CRC Press, p 27-40 (1985).

Bopp, C. A., Greene, K. D., Downes, F. P., Sowers, E. G., Wells, J. G., and Wachsmuth, I. K. Unusual verotoxin-producing *Escherichia coli* associated with hemorrhagic colitis. *J. Clin. Microbiol.* 25:1486-1489 (1987).

Borie, C. F., Monreal, Z., Martinez, J., Arellano, C, and Prado, V. Detection and characterization of enterohaemorrhagic *Escherichia coli* in slaughtered cattle. *Zentralbl. Veterinarmed.* 44:273-279 (1997).

Boyce, T. G., Swerdlow, D. L., and Griffin, P. M. *Escherichia coli* 0157:H7 and the hemolytic-uremic syndrome. *N. Engl. J. Med.* 333:364-368 (1995).

Bustamante, V. H., Santana, F. J., Calva, E., and Puente, J. L. Transcriptional regulation of type III secretion genes in enteropathogenic *Escherichia coli*: Ler antagonizes H—NS-dependent repression. *Mol. Microbiol.* 39:664-678 (2001).

Butterton J R, Boyko S A, Calderwood S B. Use of the *Vibrio cholerae* irgA gene as a locus for insertion and expression of heterologous antigens in cholera vaccine strains. *Vaccine,* 11:1327-35 (1993)

Butterton J R, Ryan E T, Acheson D W K, Calderwood S B. Co-expression of the B subunit of Shiga Toxin 1 and EaeA from enterohemorrhagic *Escherichia coli* in *Vibrio cholerae* vaccine strains. *Infect Immun,* 65:2127-35 (1997).

Calderwood S B, Auclair F, Donohue R A, Keusch G T., Mekalanos J J. Nucleotide sequence of the Shiga-like toxin genes of *Escherichia coli*. *Proc Natl Acad Sci USA,* 84:4364-8 (1987).

Camguilhem R, Milon A. Biotypes and 0 serogroups of *Escherichia coli* involved in intestinal infections of weaned rabbits: clues to diagnosis of pathogenic strains. *J Clin Microbiol* 27:743-7 (1989).

Cantey J R, Inman L R. Diarrhea due to *Escherichia coli* strain RDEC-I in the rabbit: the Peyer's patch as the initial site of attachment and colonization. *J Infect Dis,* 143:440-6 (1981)

Cantey, J. R. and R. K. Blake. Diarrhea due to *Escherichia coli* in the rabbit: a novel mechanism. *J. Infect. Dis.* 135: 454-462 (1977)

Cantey, J. R., R. K. Blake, J. R. Williford, and S. L. Moseley. Characterization of the *Escherichia coli* AF/R1 pilus operon: novel genes necessary for transcriptional regulation and for pilus-mediated adherence. *Infect. Immun.* 67:2292-2298 (1999).

Capozzo, A. V., V. Pistone Creydt, G. Dran, G. Fernandez, S. Gomez, L. V. Bentancor, C. Rubel, C. Ibarra, M. Isturiz, and M. S. Palermo. Development of DNA vaccines against hemolytic-uremic syndrome in a murine model. Infect. Immun. 71:3971-3978 (2003)

Carter, A. O., Borczyk, A. A., Carlson, J. A., Harvey, B., Hockin, J. C, Karmali, M. A., Krishnan, C, Korn, D. A., and Lior, H. A severe outbreak of *Escherichia coli* 0157:H7-associated hemorrhagic colitis in a nursing home. *N. Engl. J. Med* 317:1496-1500 (1987).

China, B., Jacquemin, E., Devrin, A. C, Pirson, V., and Mainil, J. Heterogeneity of the eae genes in attaching/effacing *Escherichia coli* from cattle: comparison with human strains. *Res. Microbiol.* 150:323-332 (1999).

Curtiss R III, Goldschmidt R M, Fletchhall N B, Kelly S M. Avirulent *Salmonella typhimurium* delta cya delta crp oral vaccine strains expressing a streptococcal colonization and virulence antigen. *Vaccine,* 6:155-60 (1988).

Dean-Nystrom, E. A. Bovine *Escherichia coli* 0157:H7 infection medel. Jn "*E. coli* Shiga Toxin methods and protocols" (D. Philpott and F. Ebel, Eds.), pp. 329-338. Human Press Inc. (2003)

Dean-Nystrom, E. A., L. J. Gansheroff, M. Mills, H. W. Moon, and A. D. O'Brien. Vaccination of pregnant dams with intimin (0157) protects suckling piglets from *Escherichia coli* O157:H7 infection. *Infect. Iirmun.* 70:2414-2418 (2002).

Deng, W., J. L. Puente, S. Gruenheid, Y. Li, B. A. Vallance, A. Vazquez, J. Barba, J. A. Ibarra, P. O'Donnell, P. Metalnikov, K. Ashman, S. Lee, D. Goode, T. Pawson, and B. B. Finlay. Dissecting virulence: Systematic and functional analyses of a pathogenicity island. *Proc. Natl. Acad. Sci. U.S.A* 101:3597-3602 (2004)

Deng, W., Y. Li, B. A. Vallance, and B. B. Finlay. Locus of enterocyte effacement from *Citrobacter rodentium*: sequence analysis and evidence for horizontal transfer among attaching and effacing pathogens. *Infect. Iwwun.* 69:6323-6335 (2001)

Desvaux M, Parham N J, Henderson I R. The autotransporter secretion system. *Res Microbiol.* 155:53-60 (2004).

Donnenberg, M. S. and J. B. Kaper. Construction of an eae deletion mutant of enteropathogenic *Escherichia coli* by using a positive-selection suicide vector. *Infect. Iπonun.* 59:4310-4317 (1991).

Donnenberg, M. S., Tacket, C. O., James, S. P., Losonsky, G., Nataro, J. P., Wasserman, S. S., Kaper, J. B., and Levine, M. M. Role of the eaeA gene in experimental enteropathogenic *Escherichia coli* infection. *J. Clin. Invest* 92:1412-1417 (1993).

Donnenberg, M. S., Tzipori, S., McKee, M. L., O'Brien, A. D., Alroy, J., and Kaper, J. B. The role of the eae gene of enterohemorrhagic *Escherichia coli* in intimate attachment in vitro and in a porcine model. *J Clin Invest* 92:1418-1424 (1993).

Doyle, M P. Focusing on Cattle to Reduce the Incidence of *Escherichia coli* 0157 Infections in Humans. Absrt. 0-19, 5th International Symposium on 'Shiga Toxin (Verocytotoxin)—*Producing Escherichia coli Infections*, Scotland (2003)

Ebel, F., T. Podzadel, M. Rohde, A. U. Kresse, S. Kramer, C. Deibel, C. A. Guzman, and T. Chakraborty. Initial binding of Shiga toxin-producing *Escherichia coli* to host cells and subsequent induction of actin rearrangements depend on filamentous EspA-containing surface appendages. *Mol. Microbiol.* 30:147-161 (1998).

Edson, C. O., Ealding, W., and Lefkoowitz, J. A lavage technique allowing repeated measurement of IgA antibody in mouse intestinal secretions. *J. Immunol. Methods* 67:101-08 (1984).

Elliott S J, Kaper J B. Role of type 1 fimbriae in EPEC infections. *Microb Pathog* 23:113-8 (1997).

Elliott, S. J., L. A. Wainwright, T. K. McDaniel, K. G. Jarvis, Y. K. Deng, L. C. Lai, B. P. McNamara, M. S. Donnenberg, and J. B. Kaper. The complete sequence of the locus of enterocyte effacement (LEE) from enteropathogenic *Escherichia coli* E2348/69. *Mol. Microbiol.* 28:1-4 (1998).

Elliott, S. J., Sperandio, V., Giron, J. A., Shin, S., Mellies, J. L., Wainwright, L., Hutcheson, S. W., McDaniel, T. K., and Kaper, J. B. The locus of enterocyte effacement (LEE)-encoded regulator controls expression of both LEE- and non-LEE-encoded virulence factors in enteropathogenic and enterohemorrhagic *Escherichia coli*. *Infect. Immun.* 68:6115-6126 (2000).

Elson, C. O., Ealding, W., and Lefkoowitz, J. (1984) A lavage technique allowing repeated measurement of IgA antibody in mouse intestinal secretions. J. Immunol. Methods 67, 101-08. 2004.

Fiederling F, Boury M, Petit C, Milon A. Adhesive factor/rabbit 2, a new fimbrial adhesin and a virulence factor from *Escherichia coli* 0103, a serogroup enteropathogenic for rabbits. Infect Immun, 65:847-51 (1997).

Frankel, G, A. D. Philips, M. Novakova, M. Batchelor, S. Hicks, and G. Dougan. Generation of *Escherichia coli* intimin derivatives with differing biological activities using site-directed mutagenesis of the intimin C-terminus domain. *Mol. Microbiol.* 29:559-570 (1998).

Frankel, G., A. D. Phillips, M. Novakova, H. Field, D. C. Candy, D. B. Schauer, G. Douce, and G. Dougan. Intimin from enteropathogenic *Escherichia coli* restores murine virulence to a *Citrobacter rodentium* eaeA mutant: induction of an immunoglobulin A response to intimin and EspB. *Infect. Iwinun.* 64:5315-5325 (1996).

Frankel, G., D. C. Candy, E. Fabiani, J. Adu-Bobie, S. Gil, M. Novakova, A. D. Phillips, and G. Dougan, Molecular characterization of a carboxy-terminal eukaryotic-cell-binding domain of intimin from enteropathogenic *Escherichia coli*. *Infect. Immun.* 63:4323-4328 (1995).

Frankel, G., Lider, O., Hershkoviz, R., Mould, A. P., Kachalsky, S. G., Candy, D. C. A., Cahalon, L., Humphries, M. J., and Dougan, G. The cell-binding domain of intimin from enteropathogenic *Escherichia coli* binds to betal integrins. *J. Biol. Chem.* 271:20359-20364 (1996).

Funatogawa, K., Ide, T., Kirikae, F., Saruta, K., Nakano, M., and Kirikae, T. Use of immunoglobulin enriched bovine colostrum against oral challenge with enterohaemorrhagic *Escherichia coli* O157:H7 in mice. *Microbiol. Immunol.* 46:761-766 (2002).

Galan J E, Nakayama K, Curtiss R III. Cloning and characterization of the asd gene of *Salmonella typhimurium*: use in stable maintenance of recombinant plasmids in *Salmonella* vaccine strains. *Gene,* 94:29-35 (1990).

Galen J E, Nair J, Wang J Y, Wasserman S S, Tanner M K, Sztein M B, et al. Optimization of plasmid maintenance in the attenuated live vector vaccine strain *Salmonella typhi* CVD 908-htrA. *Infect Immun,* 67:6424-33 (1999).

Gentry M K, Dalrymple J M. Quantitative microtiter cytotoxicity assay for Shiga toxin. *J Clin. Microbiol.,* 12:361-6 (1980).

Gentschev I, Dietrich G, Goebel W. The *E. coli* α-hemolysin secretion system and its use in vaccine development. *Trend Microbiol.* 10:39-45 (2002).

Gentschev I, Hess J, Goebel W. Change in the cellular localization of alkaline phosphatase by alteration of its carboxy-terminal sequence. *MoI Gen Genet,* 222:211-6 (1990).

Gentschev I, Sokolovic Z, Mollenkopf H J, Hess J, Kaufmann S H, Kuh M, et al. *Salmonella* strain secreting active listeriolysin changes its intracellular localization. *Infect. Immun.* 63:4202-5 (1995).

Ghaem-Maghami, M., C. P. Simmons, S. Daniell, M. Pizza, D. Lewis, G. Frankel, and G. Dougan. Intimin-specific immune responses prevent bacterial colonization by the attaching-effacing pathogen *Citrobacter rodentium*. *Infect. Immun.* 69:5597-5605 (2001)

Gray L, Mackman N, Nicaud J M, Holland I B. The carboxy-terminal region of haemolysin 2001 is required for secretion of the toxin from *Escherichia coli*. *MoI Gen Genet,* 205:127-33 (1986).

Griffin, P. M. and R. V. Tauxe. 1991. The epidemiology of infections caused by *Escherichia coli* 0157:H7, other enterohemorrhagic *E. coli*, and the associated hemolytic uremic syndrome. Epidemiol. Rev. 13:60-98.

Gyles, C. L. *Escherichia coli* verotoxins and other cytotoxins. In "*Escherichia coli* in domestic animals and humans" (C. L. Gyles, Ed.), pp. 365-398. *CAB international* (1994)

Haack K R, Robinson C L, Miller K J, Fowlkes J W, Mellies J L. Interaction of Ler at the LEE5 (tir) operon of enteropathogenic *Escherichia coli*. *Infect Immun,* 71:384-92 (2003).

Hane M W, Wood T H. *Escherichia coli* K-12 mutants resistant to nalidixic acid: genetic mapping and dominance studies. *J Bacterid,* 99:238-41 (1969).

Hartland, E. L., M. Batchelor, R. M. Delahay, C. Hale, S. Matthews, G. Dougan, S. Knutton, I. Connerton, and G. Frankel. Binding of intimin from enteropathogenic *Escherichia coli* to Tir and to host cells. *MoI. Microbiol.* 32:151-158 (1999).

Hess J, Gentschev I, Goebel W, Jarchau T. Analysis of the haemolysin secretion system by PhoA-HlyA fusion proteins. *MoI Gen Genet,* 224:201-8 (1990).

Hicks, S., Frankel, G., Kaper, J. B., Dougan, G., and Phillips, A. D. Role of intimin and bundle-forming pili in enteropathogenic *Escherichia coli* adhesion to pediatric intestinal tissue in vitro. *Infect. Immun.* 66:1570-1578 (1998).

Hoiseth S K, Stocker B A. Aromatic-dependent *Salmonella typhimurium* are non-virulent and effective as live vaccines. Nature, 291:238-9 (1981).

Hone D, Attridge S, van den Bosch L, Hackett J. A chromosomal integration system for stabilization of heterologous genes in *Salmonella* based vaccine strains. *Microb Pathog,* 5:407-18 (1988).

Hopkins, S., Kraehenbuhl, J. P., Schodel, F., Potts, A., Peterson, D., De Grandi, P., and Nardelli-Haef liger, D. A recombinant *Salmonella typhimurium* vaccine induces local immunity by four different routes of immunization. *Infect. Iznmun.* 63:3279-3286 (1995).

Hovde, C. J., Austin, P. R., Cloud, K. A., Williams, C. J., and Hunt, C. W. Effect of cattle diet on *Escherichia coli* O157:H7 acid resistance. *Appl. Environ. Microbiol.* 65:3233-3235 (1999).

Hovde, C. J., Calderwood, S. B., Mekalanos, J. J., and Collier, R. J. Evidence that glutamic acid 167 is an active-site residue of Shiga-like toxin I. *Proc. Natl. Acad. Sci. U.S.A,* 85: 2568-2572 (1988).

Ishikawa, S., K. Kawahara, Y. Kagami, Y. Isshiki, A. Kaneko, H. Matsui, N. Okada, and H. Danbara. Protection against Shiga toxin 1 challenge by immunization of mice with purified mutant Shiga toxin 1. *Infect Immun.* 71:3235-9 (2003).

Jackson M P. Structure-function analyses of Shiga toxin and the Shiga-like toxins. *Microb Pathog,* 235-142. Department of Immunology and Microbiology, Wayne State University School of Medicine, Detroit, Mich. 48201 (1990).

Jackson, M. P., Wadolkowski, E. A., Weinstein, D. L., Holmes, R. K., and O'Brien, A. D. Functional analysis of the Shiga toxin and Shiga-like toxin type II variant binding subunits by using site-directed mutagenesis. J. Bacteriol. 172:653-657 (1990).

Janke, B. H., Francis, D. H., Collins, J. E., Libal, M. C, Zeman, D. H., and Johnson, D. D. Attaching and effacing *Escherichia coli* infections in calves, pigs, lambs, and dogs. *J. Vet. Diagn. Invest* 1:6-11 (1989).

Jerse, A. E., J. Yu, B. D. Tall, and J. B. Kaper. A genetic locus of enteropathogenic *Escherichia coli* necessary for the production of attaching and effacing lesions on tissue culture cells. *Proc. Natl. Acad. Sci. U.S.A* 87:7839-7843 (1990).

Judge, N. A., Mason, H. S., and O'Brien, A. D. Plant cell-based intimin vaccine given orally to mice primed with intimin reduces time of *Escherichia coli* O157:H7 shedding in feces. *infect. Ixmun.* 72:168-175 (2004).

Kaper J B, Nataro J P, Mobley H L. Pathogenic *Escherichia coli. Nat Rev Microbiol.,* 2:123-40 (2004).

Kaper, J. B., Enterohemorrhagic *Escherichia coli. Curr. Opin. Microbiol.* 1:103-108 (1998).

Kaper, J. B., J. P. Nataro, and H. L. Mobley. Pathogenic *Escherichia coli. Nat Rev Microbiol.* 2:123-40 (2004).

Karaolis, D. K., T. K. McDaniel, J. B. Kaper, and E. C. Boedeker. Cloning of the RDEC-I locus of enterocyte effacement (LEE) and functional analysis of the phenotype on HEp-2 cells. *Adv. Exp. Med. Biol.* 412:241-245 (1997).

Karmali, M. A., Petric, M., Lim, C, Fleming, P. C, Arbus, G. S., and Lior, H. The association between idiopathic hemolytic uremic syndrome and infection by verotoxin-producing *Escherichia coli. J. Infect. Dis.* 151:775-782 (1985).

Kawahara, M., Matsuo, K., Nakasone, T., Hiroi, T., Kiyono, H., Matsumoto, S., Yamada, T., Yamamoto, N., and Honda, M. Combined intrarectal/intradermal inoculation of recombinant *Mycobacterium bovis bacillus* Calmette-Guerin (BCG) induces enhanced immune responses against the inserted HIV-I V3 antigen. *Vaccine* 21:158-166 (2002).

Kenny, B., Devinney, R., Stein, M., Reinscheid, D. J., Frey, E. A., and Finlay, B. B. Enteropathogenic *E. coli* (EPEC) transfers its receptor for intimate adherence into mammalian cells. *Cell* 91:511-520 (1997).

Ketley J M, Kaper J B, Herrington D A, Losonsky G, Levine M M. Diminished immunogenicity of a recombination-deficient derivative of *Vibrio cholerae* vaccine strain CVD103. Infect Immun., 58:1481-84 (1990).

Killham K, Jones D. Survival of *Escherichia coli* O157 in Environmental Matrices. Absrt. P-24, 5th International Symposium on 'Shiga Toxin (Verocytotoxin)—Producing *Escherichia coli* Infections', Scotland (2003)

Klapproth, J. M., I. C. Scaletsky, B. P. McNamara, L. C. Lai, C. Mal strom, S. P. James, and M. S. Donnenberg. A large loxin from lathogenic *Escherichia coli* strains that inhibits lymphocyte activation. *Infect. Iwmun.* 68:2148-55 (2000).

Klauser T, Kramer J, Otzelberger K, Pohlner J, Meyer T F. Characterization of the *Neisseria* IgA beta-core, the essential unit for outer membrane targeting and extracellular protein secretion. *J Mol Biol,* 234:579-93 (1993).

Kleanthous, H., Myers, G. A., Georgakopoulos, K. M., Tibbitts, T. J., Ingrassia, J. W., Gray, H. L., Ding, R., Zhang, Z. Z., Lei, W., Nichols, R., Lee, C. K., Ermak, T. H., and Monath, T. P. Rectal and intranasal immunizations with recombinant urease induce distinct local and serum immune responses in mice and protect against *Helicobacter pylori* infection. *Infect. Immun.* 66:2879-2886 (1998).

Konieczny M P, Suhr M, Noll A, Autenrieth I B, Alexander S M. Cell surface presentation of recombinant (poly-) peptides including functional T-cell epitopes by the AIDA autotransporter system. *FEMS Immunol Med Microbiol,* 27:321-32 (2000).

Lattemann C T, Maurer J, Gerland E, Meyer T F. Autodisplay: functional display of active beta-lactamase on the surface of *Escherichia coli* by the AIDA-I autotransporter. *J. Bacteriol.* 182:3726-33 (2000).

Levine M M, Kaper J B, Herrington D, Ketley J, Losonsky G, Tacket C O, et al. Safety, immunogenicity, and efficacy of recombinant live oral cholera vaccines, CVD 103 and CVD 103-HgR. *Lancet,* 2:467-70 (1988).

Levine et al., *J. Clin. Invest.,* 79:888-902 (1987)

Low J C, Besser T E Mahajan A Gunn G J Pearce M C McKendrick I J Smith D G E and Gaily D L. Lymphoid Follicle-Dense Mucosa at the Terminal Rectum is the Principal Site of Colonization of Enterohaemorrhagic *Escherichia coli* O157:H7 in the Bovine Host. Absrt. P-129, 5th International Symposium on 'Shiga Toxin (Verocytotoxin)—Producing *Escherichia coli* Infections', Scotland (2003)

Ludwig, K., M. A. Karmali, C. R. Smith, and M. Petric. Cross-protection against challenge by intravenous *Escherichia coli* verocytotoxin 1 (VT1) in rabbits immunized with VT2 toxoid Can. *J. Microbiol.* 48:99-103 (2002).

Luo, Y., E. A. Frey, R. A. P fuetzner, A. L. Creagh, D. G. Knoechel, C. A. Haynes, B. B. Finlay, and N. C. Strynadka. Crystal structure of enteropathogenic *Escherichia coli* intimin-receptor complex. *Nature* 405:1073-1077 (2000).

Mackman N, Baker K, Gray L, Haigh R, Nicaud J M, Holland I B. Release of a chimeric protein into the medium from *Escherichia coli* using the C-terminal secretion signal of a hemolysin. *EMBO J,* 6:2835-41 (1987).

Marches O, Ledger T N, Boury M, Ohara M, Tu X, Goffaux F, et al. Enteropathogenic and enterohaemorrhagic *Escherichia coli* deliver a novel effector called Cif, which blocks cell cycle G2/M transition. *Mol Microbiol,* 50:1553-67 (2003).

Marches, O., J. P. Nougayrede, S. Boullier, J. Mainil, G. Charlier, I. Raymond, P. Pohl, M. Boury, J. De Rycke, A. Milon, and E. Oswald. Role of Tir and Intimin in the virulence of rabbit enteropathogenic *Escherichia coli* serotype O103:H2. *Infect. Iwmun.* 68:2171-2182 (2000).

Marques, L. R., Moore, M. A., Wells, J. G., Wachsmuth, I. K., and O'Brien, A. D. Production of Shiga-like toxin by *Escherichia coli. J. Infect. Dis.* 154:338-341 (1986).

Matussek, A., Lauber, J., Bergau, A., Hansen, W., Rohde, M., Dittmar, K. E., Gunzer, M., Mengel, M., Gatzlaff, P., Hartmann, M., Buer, J., and Gunzer, F. Molecular and functional analysis of Shiga toxin-induced response patterns in human vascular endothelial cells. *Blood* 102:1323-1332 (2003).

McDaniel T K. Kaper J B. A cloned pathogenicity island from enteropathogenic *Escherichia coli* confers the attaching and effacing phenotype on *E. coli* K-12. *Mol Microbiol,* 23:399-407 (1997).

McKee, M. L. and A. D. O'Brien. Truncated enterohemorrhagic *Escherichia coli* (EHEC) O157:H7 intimin (EaeA) fusion proteins promote adherence of EHEC strains to HEp-2 cells. *Infect. Immun.* 64:2225-2233 (1996).

McNamara, B. P., A. Koutsouris, C. B. O'Connell, J. P. Nougayrede, M. S. Donnenberg, and G. Hecht. Translocated EspF protein from enteropathogenic *Escherichia coli* disrupts host intestinal barrier function. *J. Clin. Invest.* 107: 621-629 (2001).

Mead, P. S., Slutsker, L., Dietz, V., McCaig, L. F., Bresee, J. S., Shapiro, C, Griffin, P. M., and Tauxe, R. V. Food-related illness and death in the United States. *Emerg. Infect. Dis.* 5:607-625 (1999).

Mellies J L, Elliott S L, Sperandio V, Donnenberg M S, Kaper J B. The Per regulon of enteropathogenic *Escherichia coli*: identification of a regulatory cascade and a novel transcriptional activator, the locus of enterocyte effacement (LEE)-encoded regulator (Ler). *Mol Microbiol,* 33:296-306 (1999)

Mellies, J. L., Elliott, S. J., Sperandio, V., Donnenberg, M. S., and Kaper, J. B. The Per regulon of enteropathogenic *Escherichia coli*: identification of a regulatory cascade and a novel transcriptional activator, the locus of enterocyte effacement (LEE)-encoded regulator (Ler). *Mol Microbiol.* 33: 296-306 (1999).

Mesteky, Newby, In: Local immune response of the gut, CRC Press, Newby and Stocks Eds, 143-160 (1987)

Miller J H. Experiments in Molecular Genetics. Cold Spring Harbor: Cold Spring Harbor Laboratory Press (1972).

Mitchell, L. A. and Galun, E. Rectal immunization of mice with hepatitis A vaccine induces stronger systemic and local immune responses than parenteral immunization. *Vaccine,* 21: 1527-1538 (2003a).

Mobassaleh, M., Donohue-Rolf e, A., Jacewicz, M., Grand, R. J., and Keusch, G. T. Pathogenesis of *shigella* diarrhea: evidence for a development ally regulated glycolipid receptor for *shigella* toxin involved in the fluid secretory response of rabbit small intestine. *J. Infect. Dis.* 157:1023-1031 (1988).

Moon, H. W., Whipp, S. C, Argenzio, R. A., Levine, M. M., and Giannella, R. A. Attaching and effacing activities of rabbit and human enteropathogenic *Escherichia coli* in pig and rabbit intestines. *Infect. Immun.* 41:1340-1351 (1983).

Nagano, K., Sugisaki, T., Taguchi, K., Hara, T., Naiki, M., and Mori, H. A murine model of enterohemorrhagic *Escherichia coli* 0157:H7 infection to assess immunopotentiating activity of drugs on mucosal immunity: effect of drugs. *J. Pharmacol. Sci.* 91:219-228 (2003).

Nagano, K., Taguchi, K., Hara, T., Yokoyama, S., Kawada, K., and Mori, H. Adhesion and colonization of enterohemorrhagic *Escherichia coli* 0157:H7 in cecum of mice. *Microbiol. Immunol.* 47:125-132 (2003).

Nakase, H., Okazaki, K., Tabata, Y., Uchida, K., Uose, S., Ohana, M., Nishi, T., Watanabe, T., Matsuura, M., Hisatsune, H., Matsumura, K., Itoh, T., Kawanami, C, and Chiba, T. Rectal immunization with antigen-containing microspheres induces stronger Th2 responses than oral immunization: a new method for vaccination. *Vaccine* 20:377-384 (2001).

Nataro J P, Kaper J B. Diarrheagenic *Escherichia coli*. *Clin Microbiol Rev,* 11:142-201 (1998).

Nataro, J. P. and Kaper, J. B. Diarrheagenic *Escherichia coli*. *Clin. Microbiol. Rev.* 11:142-201 (1998).

Naylor S Low C, 3Besser T 4 Mahajan A 5 Gunn G 6 Pearce M 7 McKendrick 18 Donachie W 9 Smith D. *Escherichia coli* 0157:H7Colonisation of the Bovine GI Tract. Absrt. 0-8, 5th International Symposium on 'Shiga Toxin (Verocytotoxin)—Producing *Escherichia coli* Infections, Scotland (2003)

Nicholls, L., Grant, T. H., and Robins-Browne, R. M. Identification of a novel genetic locus that is required for in vitro adhesion of a clinical isolate of enterohaemorrhagic *Escherichia coli* to epithelial cells. *Mol. Microbiol.* 35:275-288 (2000).

Nishikawa K, Matsuoka K, Kita E, Okabe N, Mizuguchi M, Hino K, Miyazawa S, Yamasaki C, Aoki J, Takashima S, Yamakawa Y, Nishijima M, Terunuma D, Kuzuhara H, Natori Y. A therapeutic agent with oriented carbohydrates for treatment of infections by Shiga toxin-producing *Escherichia coli* 0157:H7. *Proc Natl. Acad. Sci. U.S.A.* 99:7669-7674 (2002).

Noel J M, Wolf M K McQueen C Fleming E Pineiro-Carrero V Boedeker E. RDEC-I infection is protective against challenge with Shiga-like toxin-I producing, isogenic strain (RDEC-H19A): Histologic assessment correlates with clinical protection. E76. Abstracts of the 95th General Meeting ASM. (1995)

Noel, J. M. and Boedeker, E. C. Enterohemorrhagic *Escherichia coli*: a family of emerging pathogens. *Dig. Dis.* 15:67-91 (1997).

Noriega F R, Losonsky G, Wang J Y, Formal S B, Levine M M. Further characterization of delta aroA delta virG *Shigella flexneri* 2a strain CVD 1203 as a mucosal *Shigella* vaccine and as a live-vector vaccine for delivering antigens of enterotoxigenic *Escherichia coli*. *Infect Immun,* 64:23-7 (1996).

O'Brien, A. D., V. L. Tesh, A. Donohue-Rolf e, M. P. Jackson, S. Olsnes, K. Sandvig, A. A. Lindberg, and G. T. Keusch. Shiga toxin: biochemistry, genetics, mode of action, and role in pathogenesis. *Curr. Top. Microbiol. Immunol.* 180:65-94 (1992).

Ogierman M A, Paton A W, Paton J C. Up-regulation of both intimin and eae-independent adherence of shiga toxigenic *Escherichia coli* 0157 by ler and phenotypic impact of a naturally occurring ler mutation. *Infect Immun,* 68:5344-53 (2000).

Ojeda, A., Prado, V., Martinez, J., Arellano, C, Borczyk, A., Johnson, W., Lior, H., and Levine, M. M. Sorbitol-negative phenotype among enterohemorrhagic *Escherichia coli* strains of different serotypes and from different sources. *J. Clin. Microbiol.* 33:2199-2201 (2000).

Omisakin, F., MacRae, M., Ogden, I. D., and Strachan, N. J. Concentration and prevalence of *Escherichia coli* 0157 in cattle feces at slaughter. *Appl. Environ. Microbiol.* 69:2444-2447 (2003).

Oswald, E., H. Schmidt, S. Morabito, H. Karch, 0. Marches, and A. Caprioli. Typing of intimin genes in human and animal enterohemorrhagic and enteropathogenic *Escherichia coli*: characterization of a new intimin variant. *Infect. Immun.* 68:64-71 (2000).

Pallen M J, Chaudhuri R R, Henderson I R. Genomic analysis of secretion systems. *Curr Opin Microbiol,* 6:519-27 (2003).

Park, C. H., Gates, K. M., Vandel, N. M., and Hixon, D. L. Isolation of Shiga-like toxin producing *Escherichia coli* (0157 and non-0157) in a community hospital. *Diagn. Microbiol. Infect. Dis.* 26:69-72 (1996).

Pascual et al. *Immuno. Methods.,* 5:56-72 (1994)

Paton, J. C. and Paton, A. W. Pathogenesis and diagnosis of Shiga toxin-producing *Escherichia coli* infections. *Clin. Microbiol. Rev.* 11:450-479 (1998).

Pearson, G. R., Watson, C. A., Hall, G. A., and Wray, C. Natural infection with an attaching and effacing *Escherichia coli* in the small and large intestines of a calf with diarrhoea. *Vet. Rec.* 124:297-299 (1989).

Peeters J E, Geeroms R, Orskov F. Biotype, serotype, and pathogenicity of attaching and effacing enteropathogenic *Escherichia coli* strains isolated from diarrheic commercial rabbits. Infect Immun; 56:1442-8 (1988).

Perna, N. T., Mayhew, G. F., Posfai, G., Elliott, S., Donnenberg, M. S., Kaper, J. B., and Blattner, F. R. Molecular evolution of a pathogenicity island from enterohemorrhagic *Escherichia coli* O157:H7. *Infect. Imun.* 66:3810-3817 (1998).

Perna N T, Plunkett G 3rd, Burland V. et al. Genome sequence of enterohaemorrhagic *Escherichia coli* 0157:H7. Nature. 409 (6819):529-33 (2001).

Pierard, D., Van Etterijck, R., Breynaert, J., Moriau, L., and Lauwers, S. Results of screening for verocytotoxin-producing *Escherichia coli* in faeces in Belgium. Eur. J. Clin. Microbiol. Infect. Dis. 9:198-201 (1990).

Pospischil, A., Mainil, J. G., Baljer, G., and Moon, H. W. Attaching and effacing bacteria in the intestines of calves and cats with diarrhea. *Vet. Pathol.* 24:330-334 (1987).

Potter, A. A., Klashinsky, S., Li, Y., Frey, E., Townsend, H., Rogan, D., Erickson, G., Hinkley, S., Klopfenstein, T., Moxley, R. A., Smith, D. R., and Finlay, B. B. Decreased shedding of *Escherichia coli* 0157:H7 by cattle following vaccination with type III secreted proteins. *Vaccine* 22:362-369 (2004).

Rafiee, P., H. Leffler, J. C. Byrd, F. J. Cassels, E. C. Boedeker, and Y. S. Kim. A sialoglycoprotein complex linked to the microvillus cytoskeleton acts as a receptor for pilus (AF/R1) mediated adhesion of enteropathogenic *Escherichia coli* (RDEC-I) in rabbit small intestine. *J. Cell Biol.* 115:1021-1029 (1991).

Ramachandran, V., K. Brett, M. A. Hornitzky, M. Dowton, K. A. Bettelheim, M. J. Walker, and S. P. Djordjevic. Distribution of intimin subtypes among *Escherichia coli* isolates from ruminant and human sources. *J. Clin. Microbiol.* 41:5022-5032 (2003).

Rey, J., Blanco, J. E., Blanco, M., Mora, A., Dahbi, G., Alonso, J. M., Hermoso, M., Hermoso, J., Alonso, M. P., Usera, M. A., Gonzalez, E. A., Bernardez, M. I., and Blanco, J. Serotypes, phage types and virulence genes of shiga-producing *Escherichia coli* isolated from sheep in Spain. *Vet. Microbiol.* 94:47-56 (2003).

Rimsky S, Zuber F, Buckle M, Buc H. A molecular mechanism for the repression of transcription by the H—NS protein. *Mol Microbiol*, 42:1311-1323 (2001).

Robins-browne, R. M., Elliot, E., and Desmarchelier, P. Shiga toxin-producing *Escherichia coli* in Australia. In "*Escherichia coli* 0157:H7 and other Shiga Toxing-producing *E. coli*" (J. B. Kaper and A. D. O'Brien, Eds.), ASM Press, Washington (1998).

Ruiz-Olvera P, Ruiz-Perez F, Sepulveda N V, Santiago-Machuca A, Maldonado-Rodriguez, R, Garcia-Elorriaga G, et al. Display and release of the *Plasmodium falciparum* circumsporozoite protein using the autotransporter M is L of *Salmonella enterica*. *Plasmid,* 50:12-27 (2003).

Ruiz-Perez F, Leon-Kempis R, Santiago-Machuca A. Ortega-Pierres G, Barry E, Levine M, et al. Expression of the *Plasmodium falciparum* immunodominant epitope (NANP) 4 on the surface of *Salmonella enterica* using the autotransporter MisL. *Infect Immun,* 70:3611-20 (2002).

Sambrook J, Russell D W. Molecular cloning: a laboratory manual, 3rd ed. Cold Spring Harbor: Cold Spring Harbor Laboratory Press, (2001).

Sanchez-Sanmart in C, Bustamante V H, Calva E, Puente J L. Transcriptional regulation of the orfl9 gene and the tircesT-eae operon of enteropathogenic *Escherichia coli. J Bacterid,* 183:2823-33 (2001).

Sanderson, M. W., Besser, T. E., Gay, J. M., Gay, C. C, and Hancock, D. D. Fecal *Escherichia coli* 0157:H7 shedding patterns of orally inoculated calves. *Vet Microbiol.* 69:199-205 (1999)

Schoonderwoerd, M., Clarke, R. C, van Dreumel, A. A., and Rawluk, S. A. Colitis in calves: natural and experimental infection with a verotoxin-producing strain of *Escherichia coli* 0111:NM. *Can. J. Vet Res.* 52:484-487 (1988).

Scotland, S. M., Willshaw, G. A., Smith, H. R., and Rowe, B. Properties of strains of *Escherichia coli* O26:H11 in relation to their enteropathogenic or enterohemorrhagic classification. *J. Infect. Dis.* 162:1069-1074 (1990).

Senanayake S D, Brian D A. Precise large deletions by the PCR-based overlap extension methods. *Mol Biotech,* 4:13-15 (1995).

Sjogren, R., R. Neill, D. Rachmilewitz, D. Fritz, J. Newland, D. Sharpnack, C. Colleton, T. Fondacaro, P. Gemski, and E. C. Boedeker. Role of Shiga-like toxin I in bacterial enteritis: comparison between isogenic *Escherichia coli* strains induced in rabbits. *Gastroenterology* 106:306-317 (1994).

Sperandio V, Mellies J L, Delahay R M. Frankel G, Crawford, J A, Nguyen W, et al. Activation of enteropathogenic *Escherichia coli* (EPEC) LEE2 and LEE3 operons by Ler. *Mol Microbiol,* 38:781-93 (2000).

Sperandio, V., Mellies, J. L., Nguyen, W., Shin, S., and Kaper, J. B. Quorum sensing controls expression of the type III secretion gene transcription and protein secretion in enterohemorrhagic and enteropathogenic *Escherichia coli. Proc. Natl. Acad. Sci. U.S.A* 96:15196-15201 (1999).

Sperandio, V., Torres, A. G., Giron, J. A., and Kaper, J. B. Quorum sensing is a global regulatory mechanism in enterohemorrhagic *Escherichia coli* 0157:H7. *J. Bacteriol.* 183:5187-5197 (2001).

Stevens, M. P., van Diemen, P. M., Frankel, G., Phillips, A. D., and Wallis, T. S. Efa1 influences colonization of the bovine intestine by shiga toxin-producing *Escherichia coli* serotypes 05 and 0111. *Infect. Immun.* 70:5158-5166 (2002).

Stordeur, P., China, B., Charlier, G., Roels, S., and Mainril, J. Clinical signs, reproduction of attaching/effacing lesions, and enterocyte invasion after oral inoculation of an 0118 enterohaemorrhagic *Escherichia coli* in neonatal calves. *Microbes. Infect.* 2:17-24 (2000).

Sutton R G, Merson M H. Oral typhoid vaccine Ty21a. *Lancet,* 5:523 (1983)

Tacket C O, Hone D M, Losonsky G A, Guers L, Edelman R, Levine M M. Clinical acceptability and immunogenicity of CVD 908 *Salmonella typhi* vaccine strain. *Vaccine,* 10:443-6 (1992).

Takeuchi A, Inman L R, O'Hanley P D, Cantey J R, Lushbaugh W B. Scanning and transmission electron microscopic study of *Escherichia coli* 015 (RDEC-I) enteric infection in rabbits. *Infect Immun,* 19:686-94 (1978).

Tarr, C. L. and Whittam, T. S. Molecular evolution of the intimin gene in 0111 clones of pathogenic *Escherichia coli. J. Bacterid.* 184:479-487 (2002).

Tarr, P. I. and Neill, M. A. Perspective: the problem of non-0157:H7 shiga toxin (Verocytotoxin)-producing *Escherichia coli. J. Infect. Dis.* 174:1136-1139 (1996).

Tatsuno, I., Horie, M., Abe, H., Miki, T., Makino, K., Shinagawa, H., Taguchi, H., Kamiya, S., Hayashi, T., and Sasakawa, C. toxB Gene on pO157 of Enterohemorrhagic *Escherichia coli* 0157:H7 Is Required for Full Epithelial Cell Adherence Phenotype. *Infect. Immun.* 69:6660-6669 (2001).

Tesh, V. L. and O'Brien, A. D. The pathogenic mechanisms of Shiga toxin and the Shiga-like toxins. *Mol Microbiol.* 5:1817-1822 (1991).

Tkalcic, S., Zhao, T., Harmon, B. G., Doyle, M. P., Brown, C. A., and Zhao, P. Fecal shedding of enterohemorrhagic *Escherichia coli* in weaned calves following treatment with probiotic *Escherichia coli*. *J. Food Prot.* 66:1184-1189 (2003).

Torres, A. G. and Kaper, J. B. Multiple elements controlling adherence of enterohemorrhagic *Escherichia coli* 0157:H7 to HeLa cells. *Infect. Immun.* 71:4985-4995 (2003).

Torres, A. G., Giron, J. A., Perna, N. T., Burland, V., Blattner, F. R., Avelino-Flores, F., and Kaper, J. B. Identification and characterization of lpfABCC'DE, a fimbrial operon of enterohemorrhagic *Escherichia coli* 0157:H7. *Infect. Immun.* 70:5416-5427 (2002).

Tzipori, S., Gunzer, F., Donnenberg, M. S., de Montigny, L., Kaper, J. B., and Donohue-Rolf e, A. The role of the eaeA gene in diarrhea and neurological complications in a gnotobiotic piglet model of enterohemorrhagic *Escherichia coli* infection. *Infect. Immun.* 63:3621-3627 (1995).

Uchida, C, Y. Kimura, S. Kubota, and 0, Sasaki. Protective effect of *Pasteurella multocida* cell-free antigen and toxoid against challenge with toxigenic strains of *pasteurella multocida* in mice. J. Vet. Med. Sci. 65:737-740 (2003).

Veiga E, de Lorenzo V, Fernandez L A. Probing secretion and translocation of a beta-autotransporter using a reporter single-chain Fv as a cognate passenger domain. *Mol Microbiol,* 33:1232-43 (1999).

Von Moll L K, Cantey J R. Peyer's patch adherence of enteropathogenic *Escherichia coli* strains in rabbits. *Infect Immun,* 65:3788-93 (1997).

Wandersman C, Delepelaire P. TOIC, an *Escherichia coli* outer membrane protein required for hemolysin secretion. *Proc Natl Acad Sci USA,* 78:4776-80 (1990).

Watanabe M, Matsuoka K, Kita E, Igai K, Higashi N, Miyagawa A, Watanabe T, Yanoshita R, Samejima Y, Terunuma D, Natori Y, Nishikawa K. Oral therapeutic agents with highly clustered globotriose for treatment of Shiga toxigenic *Escherichia coli* infections. *J. Infect. Dis.* 189:360-368 (2004).

Willshaw, G. A., Scotland, S. M., Smith, H. R., and Rowe, B. Properties of Vero cytotoxin-producing *Escherichia coli* of human origin of O serogroups other than O157. J. Infect. Dis. 166:797-802 (1992).

Wolf M K, Andrews G P, Fritz D L, Sjogren Jr. R W, Boedeker E C. Characterization of the plasmid from *Escherichia coli* RDEC-I that mediates expression of adhesin AF/R1 and evidence that AF/R1 pili promote but are not essential for enteropathogenic disease. *Infect Immun*, 56:1846-57 (1988).

Wolf M K, Boedeker E C. Cloning of the genes for AF/R1 pili from rabbit enteroadherent *Escherichia coli* RDEC-I and DNA sequence of the major structural subunit. *Infect Immun*, 58:1124-8 (1990).

Wray, C, McLaren, I., and Pearson, G. R. Occurrence of 'attaching and effacing[1] lesions in the small intestine of calves experimentally infected with bovine isolates of verocytotoxic *E coli*. Vet. Rec. 125:365-368 (1990).

Yamasaki, C, Natori, Y., Zeng, X. T., Ohmura, M., Yamasaki, S., Takeda, Y., and Natori, Y. Induction of cytokines in a human colon epithelial cell line by Shiga toxin 1 (Stx1) and Stx2 but not by non-toxic mutant Stx1 which lacks N-glycosidase activity. *FEBS Lett.* 442:231-234 (1999).

Yokomizo, Y., Watanabe, F., Imada, Y., Inumaru, S., Yanaka, T., and Tsuji, T. Mucosal immunoadjuvant activity of the low toxic recombinant *Escherichia coli* heat-labile enterotoxin produced by *Bacillus brevis* for the bacterial subunit or component vaccine in pigs and cattle. *Vet. Immunol. Immunopathol.* 87:291-300 (2002).

Zhang, W. L., B. Kohler, E. Oswald, L. Beutin, H. Karch, S. Morabito, A. Caprioli, S. Suerbaum, and H. Schmidt. Genetic Diversity of Intimin Genes of Attaching and Effacing *Escherichia coli* Strains. *J. Clin. Microbiol.* 40:4486-4492 (2002).

Zhao, T., Tkalcic, S., Doyle, M. P., Harmon, B. G., Brown, C. A., and Zhao, P. Pathogenicity of enterohemorrhagic *Escherichia coli* in neonatal calves and evaluation of fecal shedding by treatment with probiotic *Escherichia coli*. *J. Food Prot.* 66:924-930 (2003).

Zhou, F., Kraehenbuhl, J. P., and Neutra, M. R. Mucosal IgA response to rectally administered antigen formulated in IgA-coated liposomes. *Vaccine* 13:637-644 (1995).

Zhu C, Agin T S, Elliott S J, Johnson, L A, Thate T E, Kaper J B, et al. Complete nucleotide sequence and analysis of the locus of enterocyte effacement from rabbit diarrheagenic *Escherichia coli* RDEC-I. *Infect Immun*, 69:2107-15 (2001).

Zhu C, Feng S, Thate TcE, Kaper J B, Boedeker E C. Towards a vaccine for attaching/effacing *Escherichia coli*: a LEE encoded regulator Her) mutant of rabbit enteropathogenic *Escherichia coli* is attenuated, immunogenic, and protects pabbits from lethal challenge with the virulent wild-type strain. *Vaccine* (2004)

Zhu, C, J. Harel, F. Dumas, and J. M. Fairbrother. Identification of EaeA protein in the outer membrane of attaching and effacing *Escherichia coli* O45 from pigs. *FEMS Microbiol. Lett.* 129:237-242 (1995).

Zhu C, Harel J, Jacques M, Desautels C, Donnenberg M S, Beaudry M, Fairbrother J M. Virulence properties and attaching-effacing activity of *Escherichia coli* O45 from swine postweaning diarrhea. *Infect Immun*, 62:4153-9 (1994).

Zhu, C, Feng, S, Thate, T, Kaper, J B, and Boedeker, E C. Analysis of the ler (Lee Encoded Regulator) Gene of a Rabbit Enteropathogenic *Escherichia coli* (O103:H2) And Evaluation of Its in vivo Role in Virulence. B7 Abstracts of the 101th *Gen. Mtng. ASM*, Orlando, Fla. (2002).

Zhu, C, Agin, T. S., Elliott, S. J., Johnson, L. A., Thate, T. E., Kaper, J. B., and Boedeker, E. C. Complete nucleotide sequence and analysis of the locus of enterocyte Effacement from rabbit diarrheagenic *Escherichia coli* RDEC-I. *Infect. Iwmun.* 69:2107-2115 (2001).

Zhu, C, S. Feng, T. E. Thate, J. B. Kaper, and E. C. Boedeker. Towards a vaccine for attaching/effacing *Escherichia coli*: A LEE encoded regulator (ler) mutant of rabbit enteropathogenic *Escherichia coli* is attenuated, immunogenic, and protects rabbits from lethal challenge with the wild-type virulent strain. *Vaccine*, In press (2005a).

Zhu, C, F. Ruiz-Perez, Z. Yang, Y. Mao, V. L. Hackethal, K. M. Greco, W. Choy, K. Davis, J. R. Butterton, and E. C. Boedeker. Delivery of heterologous protein antigens via hemolysin or autotransporter systems by an attenuated Ler mutant of rabbit enteropathogenic *Escherichia coli*. *Vaccine*. In press (2005b).

What is claimed is:

1. An isolated, live attenuated, double mutant of enterohemorrhagic *Escherichia coli* (EHEC) O157:H7, *E. coli* O26, or *E. coli* O111 in which the Shiga toxin coding sequence is deleted to abolish its Shiga toxin production and the nucleotide sequence coding for its bacterial adhesion protein, intimin or Eae, is mutated by deletion of the C-terminal Tir-binding domain to eliminate intimin's Tir binding activity while retaining rest of the intimin that comprises the intimin's immunodominant regions.

2. The live attenuated double mutant of claim 1, which contains no antibiotic resistance marker.

3. The live attenuated double mutant of claim 1 comprising a pharmaceutically acceptable carrier.

4. The live attenuated double mutant of claim 1 comprising an adjuvant.

5. The live attenuated double mutant of claim 2 comprising a pharmaceutically acceptable carrier.

6. The live attenuated double mutant of claim 2 comprising an adjuvant.

* * * * *

SEQUENCE LISTING

```
<160> NUMBER OF SEQ ID NOS: 63

<210> SEQ ID NO 1
<211> LENGTH: 34
<212> TYPE: DNA
<213> ORGANISM: Artificial
<220> FEATURE:
<223> OTHER INFORMATION: Synthetic

<400> SEQUENCE: 1
gatgccgaaa acaactgtaa gacaaatagc gcaa                                   34

<210> SEQ ID NO 2
<211> LENGTH: 20
<212> TYPE: DNA
<213> ORGANISM: Artificial
<220> FEATURE:
<223> OTHER INFORMATION: Synthetic
```

-continued

```
<400> SEQUENCE: 2
ccagtattac tgagattaag                                                   20

<210> SEQ ID NO 3
<211> LENGTH: 20
<212> TYPE: DNA
<213> ORGANISM: Artificial
<220> FEATURE:
<223> OTHER INFORMATION: Synthetic

<400> SEQUENCE: 3
tccgggattt gagatgtaat                                                   20

<210> SEQ ID NO 4
<211> LENGTH: 2820
<212> TYPE: DNA
<213> ORGANISM: Escherichia coli
<220> FEATURE:
<221> NAME/KEY: misc_feature
<223> OTHER INFORMATION: RDEC-1 eae
<220> FEATURE:
<221> NAME/KEY: CDS
<222> LOCATION: (1)..(2820)

<400> SEQUENCE: 4
```

| atg | att | act | cat | ggt | ttt | tat | gcc | cgg | acc | cgg | cac | aag | cat | aag | cta | 48 |
|---|---|---|---|---|---|---|---|---|---|---|---|---|---|---|---|---|
| Met | Ile | Thr | His | Gly | Phe | Tyr | Ala | Arg | Thr | Arg | His | Lys | His | Lys | Leu | |
| 1 | | | | 5 | | | | | 10 | | | | | 15 | | |

| aaa | aaa | aca | ttt | att | atg | ctt | agt | gct | ggt | tta | gga | ttg | ttt | ttt | tat | 96 |
|---|---|---|---|---|---|---|---|---|---|---|---|---|---|---|---|---|
| Lys | Lys | Thr | Phe | Ile | Met | Leu | Ser | Ala | Gly | Leu | Gly | Leu | Phe | Phe | Tyr | |
| | | | 20 | | | | 25 | | | | | 30 | | | | |

| gtt | aac | cag | aat | tca | ttt | gca | aat | ggt | gaa | aat | tat | ttt | aaa | ttg | agt | 144 |
|---|---|---|---|---|---|---|---|---|---|---|---|---|---|---|---|---|
| Val | Asn | Gln | Asn | Ser | Phe | Ala | Asn | Gly | Glu | Asn | Tyr | Phe | Lys | Leu | Ser | |
| | | 35 | | | | | 40 | | | | | 45 | | | | |

| tca | gat | tca | aaa | ctg | tta | act | caa | aat | gcc | gct | cag | gat | cgc | ctt | ttt | 192 |
|---|---|---|---|---|---|---|---|---|---|---|---|---|---|---|---|---|
| Ser | Asp | Ser | Lys | Leu | Leu | Thr | Gln | Asn | Ala | Ala | Gln | Asp | Arg | Leu | Phe | |
| 50 | | | | | 55 | | | | | 60 | | | | | | |

| tat | acg | tta | aaa | aca | ggt | gaa | act | gtt | gcc | aat | att | tct | aaa | tca | cag | 240 |
|---|---|---|---|---|---|---|---|---|---|---|---|---|---|---|---|---|
| Tyr | Thr | Leu | Lys | Thr | Gly | Glu | Thr | Val | Ala | Asn | Ile | Ser | Lys | Ser | Gln | |
| 65 | | | | 70 | | | | | 75 | | | | | 80 | | |

| ggt | atc | agt | tta | tcg | gta | att | tgg | tca | ctg | aat | aaa | cat | tta | tac | agt | 288 |
|---|---|---|---|---|---|---|---|---|---|---|---|---|---|---|---|---|
| Gly | Ile | Ser | Leu | Ser | Val | Ile | Trp | Ser | Leu | Asn | Lys | His | Leu | Tyr | Ser | |
| | | | 85 | | | | | 90 | | | | | 95 | | | |

| tcc | gaa | agc | gaa | atg | atg | aag | gct | gga | cct | ggt | cag | cag | atc | att | ttg | 336 |
|---|---|---|---|---|---|---|---|---|---|---|---|---|---|---|---|---|
| Ser | Glu | Ser | Glu | Met | Met | Lys | Ala | Gly | Pro | Gly | Gln | Gln | Ile | Ile | Leu | |
| | | | 100 | | | | | 105 | | | | | 110 | | | |

| cca | ctc | aaa | aaa | ctg | tct | gtt | gaa | tat | agt | gcc | tta | cct | gtc | tta | ggt | 384 |
|---|---|---|---|---|---|---|---|---|---|---|---|---|---|---|---|---|
| Pro | Leu | Lys | Lys | Leu | Ser | Val | Glu | Tyr | Ser | Ala | Leu | Pro | Val | Leu | Gly | |
| | | 115 | | | | | 120 | | | | | 125 | | | | |

| tcg | gca | cct | gtt | gtt | gct | gca | ggt | ggt | gtc | gct | ggt | cat | acg | aat | aaa | 432 |
|---|---|---|---|---|---|---|---|---|---|---|---|---|---|---|---|---|
| Ser | Ala | Pro | Val | Val | Ala | Ala | Gly | Gly | Val | Ala | Gly | His | Thr | Asn | Lys | |
| | 130 | | | | | 135 | | | | | 140 | | | | | |

| atg | act | aaa | atg | tcc | ccg | gac | gcg | act | aaa | agc | aac | acg | acc | gat | gac | 480 |
|---|---|---|---|---|---|---|---|---|---|---|---|---|---|---|---|---|
| Met | Thr | Lys | Met | Ser | Pro | Asp | Ala | Thr | Lys | Ser | Asn | Thr | Thr | Asp | Asp | |
| 145 | | | | | 150 | | | | | 155 | | | | | 160 | |

| aag | gct | cta | aat | tat | gcg | gca | caa | cag | gcc | gcg | agc | ctt | ggt | agc | cag | 528 |
|---|---|---|---|---|---|---|---|---|---|---|---|---|---|---|---|---|
| Lys | Ala | Leu | Asn | Tyr | Ala | Ala | Gln | Gln | Ala | Ala | Ser | Leu | Gly | Ser | Gln | |
| | | | | 165 | | | | | 170 | | | | | 175 | | |

| ctc | cag | tcg | cgc | tca | ctg | aac | ggc | gat | tac | gcg | aaa | gat | acc | gct | ctt | 576 |
|---|---|---|---|---|---|---|---|---|---|---|---|---|---|---|---|---|
| Leu | Gln | Ser | Arg | Ser | Leu | Asn | Gly | Asp | Tyr | Ala | Lys | Asp | Thr | Ala | Leu | |
| | | | 180 | | | | | 185 | | | | | 190 | | | |

| ggt | atg | gcc | agc | agc | cag | gct | tcg | tca | cag | ttg | cag | gcc | tgg | tta | caa | 624 |

```
            Gly Met Ala Ser Ser Gln Ala Ser Ser Gln Leu Gln Ala Trp Leu Gln
                    195                 200                 205 cat tat gga acg gca gag gtt aat ctg cag agt ggt aat aac ttt gac              672
His Tyr Gly Thr Ala Glu Val Asn Leu Gln Ser Gly Asn Asn Phe Asp
210                 215                 220 ggt agt tca ctg gac ttc tta tta ccg ttc tat gat tcc gaa aac atg              720
Gly Ser Ser Leu Asp Phe Leu Leu Pro Phe Tyr Asp Ser Glu Asn Met
225                 230                 235                 240 ctg gca ttt ggt cag gtc ggt gcg cgt tac att gac tcc cgc ttt acg              768
Leu Ala Phe Gly Gln Val Gly Ala Arg Tyr Ile Asp Ser Arg Phe Thr
                245                 250                 255 gca aat tta ggt gct ggc cag cgt ttt ttc ctt cct gaa aat atg ttg              816
Ala Asn Leu Gly Ala Gly Gln Arg Phe Phe Leu Pro Glu Asn Met Leu
            260                 265                 270 ggc tat aac gtc ttc att gat cag gat ttt tct ggt gat aat acc cgt              864
Gly Tyr Asn Val Phe Ile Asp Gln Asp Phe Ser Gly Asp Asn Thr Arg
        275                 280                 285 tta ggt att ggt ggc gaa tac tgg cga gac tat ttc aaa agt agc gtt              912
Leu Gly Ile Gly Gly Glu Tyr Trp Arg Asp Tyr Phe Lys Ser Ser Val
290                 295                 300 aac ggc tat ttc cgc atg agc ggc tgg cat gag tca tac aat aag aaa              960
Asn Gly Tyr Phe Arg Met Ser Gly Trp His Glu Ser Tyr Asn Lys Lys
305                 310                 315                 320 gac tat gat gag cgc ccg gca aat ggt ttt gat atc cgc ttt aat ggc             1008
Asp Tyr Asp Glu Arg Pro Ala Asn Gly Phe Asp Ile Arg Phe Asn Gly
                325                 330                 335 tat tta cca tca tat ccg gca tta ggc gcc aaa ctg atg tac gaa cag             1056
Tyr Leu Pro Ser Tyr Pro Ala Leu Gly Ala Lys Leu Met Tyr Glu Gln
            340                 345                 350 tat tat ggt gat aat gtt gct ttg ttt aat tcc gat aag ttg cag tcg             1104
Tyr Tyr Gly Asp Asn Val Ala Leu Phe Asn Ser Asp Lys Leu Gln Ser
        355                 360                 365 aat cct ggc gcg gcg acc gtt ggt gta aac tac act ccg att cct ctg             1152
Asn Pro Gly Ala Ala Thr Val Gly Val Asn Tyr Thr Pro Ile Pro Leu
370                 375                 380 gtg acg atg ggg atc gat tac cgt cat ggt acg ggt aat gaa aat gat             1200
Val Thr Met Gly Ile Asp Tyr Arg His Gly Thr Gly Asn Glu Asn Asp
385                 390                 395                 400 ctc ctt tac tca atg cag ttc cgt tat cag ttt gat aaa ccg tgg tct             1248
Leu Leu Tyr Ser Met Gln Phe Arg Tyr Gln Phe Asp Lys Pro Trp Ser
                405                 410                 415 caa caa atc gag cca cag tat gtt aac gag tta aga aca tta tcg ggc             1296
Gln Gln Ile Glu Pro Gln Tyr Val Asn Glu Leu Arg Thr Leu Ser Gly
            420                 425                 430 agc cgt tac gat ctg gtt cag cgt aat aac aat att att ctg gag tac             1344
Ser Arg Tyr Asp Leu Val Gln Arg Asn Asn Asn Ile Ile Leu Glu Tyr
        435                 440                 445 aaa aag cag gat att ctt tct ctg aat att ccg cat gat att aat ggt             1392
Lys Lys Gln Asp Ile Leu Ser Leu Asn Ile Pro His Asp Ile Asn Gly
450                 455                 460 act gaa cac agt acg cag aag att caa ttg atc gtt aag agc aaa tac             1440
Thr Glu His Ser Thr Gln Lys Ile Gln Leu Ile Val Lys Ser Lys Tyr
465                 470                 475                 480 ggt ctg gat cgt atc gtc tgg gat gat agc gca tta cgc agt cag ggc             1488
Gly Leu Asp Arg Ile Val Trp Asp Asp Ser Ala Leu Arg Ser Gln Gly
                485                 490                 495 ggt cag att cag cat ggc gga agc caa agc gca caa gac tac cag gct             1536
Gly Gln Ile Gln His Gly Gly Ser Gln Ser Ala Gln Asp Tyr Gln Ala
            500                 505                 510
```

```
att ttg cct gct tat gtg caa ggc ggc agc aat att tat aaa gtg acc     1584
Ile Leu Pro Ala Tyr Val Gln Gly Gly Ser Asn Ile Tyr Lys Val Thr
    515                 520                 525 gct cgc gcc tat gac cga aat ggt aat agt tct aat aat gta cag ctc     1632
Ala Arg Ala Tyr Asp Arg Asn Gly Asn Ser Ser Asn Asn Val Gln Leu
530                 535                 540 act att acc gtt tta ccg aat ggg cag gtt gtg gac cag gtt ggg gta     1680
Thr Ile Thr Val Leu Pro Asn Gly Gln Val Val Asp Gln Val Gly Val
545                 550                 555                 560 acg gac ttt acg gct gat aaa aca tcg gct aaa gcg gat ggc ata gaa     1728
Thr Asp Phe Thr Ala Asp Lys Thr Ser Ala Lys Ala Asp Gly Ile Glu
            565                 570                 575 gct att acc tat acc gcg acg gtt aaa aag aat ggt gta gct cag gct     1776
Ala Ile Thr Tyr Thr Ala Thr Val Lys Lys Asn Gly Val Ala Gln Ala
            580                 585                 590 aat gtc cct gta aca ttt agt att gta tcc ggg act gca act ctt ggg     1824
Asn Val Pro Val Thr Phe Ser Ile Val Ser Gly Thr Ala Thr Leu Gly
        595                 600                 605 gca aat agt gcc aga acg gat ggt aac ggt aag gcg acc gta acg ctg     1872
Ala Asn Ser Ala Arg Thr Asp Gly Asn Gly Lys Ala Thr Val Thr Leu
        610                 615                 620 aag tcg gct acg cca gga cag gtc gtc gtg tct gct aaa acc gcg gag     1920
Lys Ser Ala Thr Pro Gly Gln Val Val Val Ser Ala Lys Thr Ala Glu
625                 630                 635                 640 atg act tcg cca ctt aat gcc agc gcg gtt ata ttt gtt gat caa acc     1968
Met Thr Ser Pro Leu Asn Ala Ser Ala Val Ile Phe Val Asp Gln Thr
            645                 650                 655 aag gcc agt att act gag att aag gct gat aaa aca aca gcg aag gca     2016
Lys Ala Ser Ile Thr Glu Ile Lys Ala Asp Lys Thr Thr Ala Lys Ala
            660                 665                 670 gat ggt tct gat gcg att acc tat act gtc aga gtg atg aag gag ggg     2064
Asp Gly Ser Asp Ala Ile Thr Tyr Thr Val Arg Val Met Lys Glu Gly
        675                 680                 685 gca ccc gta gta gat cag aaa gtg acc ttt tct aag gat ttt ggg acc     2112
Ala Pro Val Val Asp Gln Lys Val Thr Phe Ser Lys Asp Phe Gly Thr
690                 695                 700 ctg aat aag act gaa gca aca acc gat cag aat ggt tat gct act gta     2160
Leu Asn Lys Thr Glu Ala Thr Thr Asp Gln Asn Gly Tyr Ala Thr Val
705                 710                 715                 720 aaa tta tca tcc aat act cct ggc aag gcc att gtt agt gca aaa gtg     2208
Lys Leu Ser Ser Asn Thr Pro Gly Lys Ala Ile Val Ser Ala Lys Val
            725                 730                 735 agt gga gta ggt aca gaa gtt aag gct act acc gtt gag ttt ttt gcc     2256
Ser Gly Val Gly Thr Glu Val Lys Ala Thr Thr Val Glu Phe Phe Ala
            740                 745                 750 ccg ttg agt att gat ggt gat aaa gtg acc gta att ggt act ggt atc     2304
Pro Leu Ser Ile Asp Gly Asp Lys Val Thr Val Ile Gly Thr Gly Ile
        755                 760                 765 acg ggg gct ctg cca aag aac tgg tta cag tat ggt cag gtt aag cta     2352
Thr Gly Ala Leu Pro Lys Asn Trp Leu Gln Tyr Gly Gln Val Lys Leu
        770                 775                 780 cag gca aca ggg ggc aat gga aaa tac aca tgg aaa tcc agt aat act     2400
Gln Ala Thr Gly Gly Asn Gly Lys Tyr Thr Trp Lys Ser Ser Asn Thr
785                 790                 795                 800 aaa att gct tct gtt gat aac tcg gga gtg ata acc tta aat gaa aaa     2448
Lys Ile Ala Ser Val Asp Asn Ser Gly Val Ile Thr Leu Asn Glu Lys
            805                 810                 815 ggg agt gcc aca att act gta gta tct ggt gat aat cag agt gcg aca     2496
Gly Ser Ala Thr Ile Thr Val Val Ser Gly Asp Asn Gln Ser Ala Thr
            820                 825                 830
```

```
tac aca att aat gca ccg ggt agt att gta att gct gtg gat aaa aat    2544
Tyr Thr Ile Asn Ala Pro Gly Ser Ile Val Ile Ala Val Asp Lys Asn
        835                 840                 845 act cga gtt acg tat ttt gat gcc gaa aac aaa tgt aag aca aat agc    2592
Thr Arg Val Thr Tyr Phe Asp Ala Glu Asn Lys Cys Lys Thr Asn Ser
850                 855                 860 gca aat tta gca cag tca aaa gaa cta ttg gcc aat atc tat tca aca    2640
Ala Asn Leu Ala Gln Ser Lys Glu Leu Leu Ala Asn Ile Tyr Ser Thr
865                 870                 875                 880 tgg ggt gct gca aat aaa tat cct tac tat tct ggt tct aaa tca ttg    2688
Trp Gly Ala Ala Asn Lys Tyr Pro Tyr Tyr Ser Gly Ser Lys Ser Leu
                885                 890                 895 act gct tgg att aaa caa tct tct tct gaa cag tca tca ggt gta tca    2736
Thr Ala Trp Ile Lys Gln Ser Ser Ser Glu Gln Ser Ser Gly Val Ser
            900                 905                 910 agc aca tat gat ttg gtt acg aag aac cag ttg atc aat gtt gga gta    2784
Ser Thr Tyr Asp Leu Val Thr Lys Asn Gln Leu Ile Asn Val Gly Val
        915                 920                 925 aac aat aag aat gct ttt tct gtt tgt gta aaa taa                    2820
Asn Asn Lys Asn Ala Phe Ser Val Cys Val Lys
930                 935

<210> SEQ ID NO 5
<211> LENGTH: 939
<212> TYPE: PRT
<213> ORGANISM: Escherichia coli

<400> SEQUENCE: 5

Met Ile Thr His Gly Phe Tyr Ala Arg Thr Arg His Lys His Lys Leu
1               5                   10                  15

Lys Lys Thr Phe Ile Met Leu Ser Ala Gly Leu Gly Leu Phe Phe Tyr
            20                  25                  30

Val Asn Gln Asn Ser Phe Ala Asn Gly Glu Asn Tyr Phe Lys Leu Ser
        35                  40                  45

Ser Asp Ser Lys Leu Leu Thr Gln Asn Ala Ala Gln Asp Arg Leu Phe
    50                  55                  60

Tyr Thr Leu Lys Thr Gly Glu Thr Val Ala Asn Ile Ser Lys Ser Gln
65                  70                  75                  80

Gly Ile Ser Leu Ser Val Ile Trp Ser Leu Asn Lys His Leu Tyr Ser
                85                  90                  95

Ser Glu Ser Glu Met Met Lys Ala Gly Pro Gly Gln Gln Ile Ile Leu
            100                 105                 110

Pro Leu Lys Lys Leu Ser Val Glu Tyr Ser Ala Leu Pro Val Leu Gly
        115                 120                 125

Ser Ala Pro Val Val Ala Ala Gly Gly Val Ala Gly His Thr Asn Lys
    130                 135                 140

Met Thr Lys Met Ser Pro Asp Ala Thr Lys Ser Asn Thr Thr Asp Asp
145                 150                 155                 160

Lys Ala Leu Asn Tyr Ala Ala Gln Gln Ala Ser Leu Gly Ser Gln
                165                 170                 175

Leu Gln Ser Arg Ser Leu Asn Gly Asp Tyr Ala Lys Asp Thr Ala Leu
            180                 185                 190

Gly Met Ala Ser Ser Gln Ala Ser Ser Gln Leu Gln Ala Trp Leu Gln
        195                 200                 205

His Tyr Gly Thr Ala Glu Val Asn Leu Gln Ser Gly Asn Asn Phe Asp
    210                 215                 220
```

```
Gly Ser Ser Leu Asp Phe Leu Leu Pro Phe Tyr Asp Ser Glu Asn Met
225                 230                 235                 240

Leu Ala Phe Gly Gln Val Gly Ala Arg Tyr Ile Asp Ser Arg Phe Thr
            245                 250                 255

Ala Asn Leu Gly Ala Gly Gln Arg Phe Phe Leu Pro Glu Asn Met Leu
            260                 265                 270

Gly Tyr Asn Val Phe Ile Asp Gln Asp Phe Ser Gly Asp Asn Thr Arg
            275                 280                 285

Leu Gly Ile Gly Gly Glu Tyr Trp Arg Asp Tyr Phe Lys Ser Ser Val
            290                 295                 300

Asn Gly Tyr Phe Arg Met Ser Gly Trp His Glu Ser Tyr Asn Lys Lys
305                 310                 315                 320

Asp Tyr Asp Glu Arg Pro Ala Asn Gly Phe Asp Ile Arg Phe Asn Gly
                325                 330                 335

Tyr Leu Pro Ser Tyr Pro Ala Leu Gly Ala Lys Leu Met Tyr Glu Gln
            340                 345                 350

Tyr Tyr Gly Asp Asn Val Ala Leu Phe Asn Ser Asp Lys Leu Gln Ser
            355                 360                 365

Asn Pro Gly Ala Ala Thr Val Gly Val Asn Tyr Thr Pro Ile Pro Leu
370                 375                 380

Val Thr Met Gly Ile Asp Tyr Arg His Gly Thr Gly Asn Glu Asn Asp
385                 390                 395                 400

Leu Leu Tyr Ser Met Gln Phe Arg Tyr Gln Phe Asp Lys Pro Trp Ser
            405                 410                 415

Gln Gln Ile Glu Pro Gln Tyr Val Asn Glu Leu Arg Thr Leu Ser Gly
            420                 425                 430

Ser Arg Tyr Asp Leu Val Gln Arg Asn Asn Asn Ile Ile Leu Glu Tyr
            435                 440                 445

Lys Lys Gln Asp Ile Leu Ser Leu Asn Ile Pro His Asp Ile Asn Gly
450                 455                 460

Thr Glu His Ser Thr Gln Lys Ile Gln Leu Ile Val Lys Ser Lys Tyr
465                 470                 475                 480

Gly Leu Asp Arg Ile Val Trp Asp Asp Ser Ala Leu Arg Ser Gln Gly
            485                 490                 495

Gly Gln Ile Gln His Gly Gly Ser Gln Ser Ala Gln Asp Tyr Gln Ala
            500                 505                 510

Ile Leu Pro Ala Tyr Val Gln Gly Gly Ser Asn Ile Tyr Lys Val Thr
            515                 520                 525

Ala Arg Ala Tyr Asp Arg Asn Gly Asn Ser Ser Asn Val Gln Leu
530                 535                 540

Thr Ile Thr Val Leu Pro Asn Gly Gln Val Val Asp Gln Val Gly Val
545                 550                 555                 560

Thr Asp Phe Thr Ala Asp Lys Thr Ser Ala Lys Ala Asp Gly Ile Glu
            565                 570                 575

Ala Ile Thr Tyr Thr Ala Thr Val Lys Lys Asn Gly Val Ala Gln Ala
            580                 585                 590

Asn Val Pro Val Thr Phe Ser Ile Val Ser Gly Thr Ala Thr Leu Gly
            595                 600                 605

Ala Asn Ser Ala Arg Thr Asp Gly Asn Gly Lys Ala Thr Val Thr Leu
            610                 615                 620

Lys Ser Ala Thr Pro Gly Gln Val Val Val Ser Ala Lys Thr Ala Glu
625                 630                 635                 640

Met Thr Ser Pro Leu Asn Ala Ser Ala Val Ile Phe Val Asp Gln Thr
```

```
            645                 650                 655
Lys Ala Ser Ile Thr Glu Ile Lys Ala Asp Lys Thr Thr Ala Lys Ala
            660                 665                 670

Asp Gly Ser Asp Ala Ile Thr Tyr Thr Val Arg Val Met Lys Glu Gly
            675                 680                 685

Ala Pro Val Val Asp Gln Lys Val Thr Phe Ser Lys Asp Phe Gly Thr
        690                 695                 700

Leu Asn Lys Thr Glu Ala Thr Thr Asp Gln Asn Gly Tyr Ala Thr Val
705                 710                 715                 720

Lys Leu Ser Ser Asn Thr Pro Gly Lys Ala Ile Val Ser Ala Lys Val
                725                 730                 735

Ser Gly Val Gly Thr Glu Val Lys Ala Thr Thr Val Glu Phe Phe Ala
                740                 745                 750

Pro Leu Ser Ile Asp Gly Asp Lys Val Thr Val Ile Gly Thr Gly Ile
            755                 760                 765

Thr Gly Ala Leu Pro Lys Asn Trp Leu Gln Tyr Gly Gln Val Lys Leu
        770                 775                 780

Gln Ala Thr Gly Gly Asn Gly Lys Tyr Thr Trp Lys Ser Ser Asn Thr
785                 790                 795                 800

Lys Ile Ala Ser Val Asp Asn Ser Gly Val Ile Thr Leu Asn Glu Lys
                805                 810                 815

Gly Ser Ala Thr Ile Thr Val Val Ser Gly Asp Asn Gln Ser Ala Thr
                820                 825                 830

Tyr Thr Ile Asn Ala Pro Gly Ser Ile Val Ile Ala Val Asp Lys Asn
            835                 840                 845

Thr Arg Val Thr Tyr Phe Asp Ala Glu Asn Lys Cys Lys Thr Asn Ser
        850                 855                 860

Ala Asn Leu Ala Gln Ser Lys Glu Leu Leu Ala Asn Ile Tyr Ser Thr
865                 870                 875                 880

Trp Gly Ala Ala Asn Lys Tyr Pro Tyr Tyr Ser Gly Ser Lys Ser Leu
                885                 890                 895

Thr Ala Trp Ile Lys Gln Ser Ser Ser Glu Gln Ser Ser Gly Val Ser
                900                 905                 910

Ser Thr Tyr Asp Leu Val Thr Lys Asn Gln Leu Ile Asn Val Gly Val
            915                 920                 925

Asn Asn Lys Asn Ala Phe Ser Val Cys Val Lys
        930                 935

<210> SEQ ID NO 6
<211> LENGTH: 25
<212> TYPE: PRT
<213> ORGANISM: Escherichia coli
<220> FEATURE:
<221> NAME/KEY: misc_feature
<223> OTHER INFORMATION: RDEC-1(delta)eae

<400> SEQUENCE: 6

Val Ile Ala Val Asp Lys Asn Thr Arg Val Thr Tyr Phe Asp Ala Glu
1               5                   10                  15

Asn Asn Val Arg Gln Ile Ala Gln Ile
            20                  25

<210> SEQ ID NO 7
<211> LENGTH: 27
<212> TYPE: DNA
<213> ORGANISM: Artificial
<220> FEATURE:
```

<223> OTHER INFORMATION: Synthetic
<220> FEATURE:
<221> NAME/KEY: misc_feature
<223> OTHER INFORMATION: B750 forward primer

<400> SEQUENCE: 7
ccggaattcc gaatggtacg gttatgc                                          27

<210> SEQ ID NO 8
<211> LENGTH: 30
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: B751 reverse primer

<400> SEQUENCE: 8
cgcggatcca gttcagttat cgttatcatt                                       30

<210> SEQ ID NO 9
<211> LENGTH: 18
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: B650 forward primer

<400> SEQUENCE: 9
gggatagata tgggaata                                                    18

<210> SEQ ID NO 10
<211> LENGTH: 36
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: B648 reverse primer

<400> SEQUENCE: 10
cttcggtgtc cttcacaatg tgcgaattag tttcca                                36

<210> SEQ ID NO 11
<211> LENGTH: 18
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: B647 forward primer

<400> SEQUENCE: 11
ttgtgaagga caccgaag                                                    18

<210> SEQ ID NO 12
<211> LENGTH: 18
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: B649 reverse primer

<400> SEQUENCE: 12
attacgagta gaactact                                                             18

<210> SEQ ID NO 13
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: B810 reverse primer

<400> SEQUENCE: 13
cgagcaaggc catcatcagg                                                           20

<210> SEQ ID NO 14
<211> LENGTH: 1035
<212> TYPE: DNA
<213> ORGANISM: Escherichia coli
<220> FEATURE:
<221> NAME/KEY: misc_feature
<223> OTHER INFORMATION: EPEC ler
<220> FEATURE:
<221> NAME/KEY: CDS
<222> LOCATION: (610)..(996)

<400> SEQUENCE: 14

```
agagactaac gcggttactt gttcagctat ttgtcccttg ttccttttta taatgcaccc          60
gttccaggtt agtgctggct gtagcttatg tccgggagac agctaataga tatatatact         120
cgtcatactt caagttgcat gtgctgcgac tgcgttcgct taccccaatc acttacttat         180
gtaagctcct ggggattcac tcgcttgccg ccttcctgta actcgaatta agtagagtat         240
agtgaaacgg ttcagcttgg ttttattct gttttatttg tttatgcaat gagatctatc          300
ttataaagag aaacgcttaa ctaaatggaa atgcaattat taaagtcgtt tgttaacgag         360
atggttttct tctatatcat tgattttaaa tggatttta aaatatatga ttttttttgt          420
tgacatttaa tgataatgta ttttacacat tagaaacag agaataataa cattttaagg          480
tggttgtttg atgaaataga tgtgtcctaa tttgatagat aaacgttatc tcacataatt         540
tatatcattt gattaattgt tgtccttcct gataaggata aggtcgctaa tagcttaaaa         600 tattaaagc atg cgg aga tta ttt att atg aat atg gaa act aat tca cat        651
           Met Arg Arg Leu Phe Ile Met Asn Met Glu Thr Asn Ser His
             1               5                  10 aca aca agt cca tac att cag ctt ata gag caa att gca gtt cta cag           699
Thr Thr Ser Pro Tyr Ile Gln Leu Ile Glu Gln Ile Ala Val Leu Gln
 15                  20                  25                  30 cag gaa gca aag cga ctg cga gag cag gaa gtt caa agt gta att gag           747
Gln Glu Ala Lys Arg Leu Arg Glu Gln Glu Val Gln Ser Val Ile Glu
                 35                  40                  45 tcg att cag aag cag att act tat tac aat ata acc tta caa gag ctg           795
Ser Ile Gln Lys Gln Ile Thr Tyr Tyr Asn Ile Thr Leu Gln Glu Leu
             50                  55                  60 gga tat act aat gtg cct gat gat gga ctc gct cgc cgg aac tca tcg           843
Gly Tyr Thr Asn Val Pro Asp Asp Gly Leu Ala Arg Arg Asn Ser Ser
         65                  70                  75 aaa ggt gtt tac tac cgc aat gaa gaa ggg cag acc tgg tcg ggc gta           891
Lys Gly Val Tyr Tyr Arg Asn Glu Glu Gly Gln Thr Trp Ser Gly Val
     80                  85                  90 ggc cga cag cca cgc tgg ctt aaa gaa gca ctg ttg aat gga atg aag           939
Gly Arg Gln Pro Arg Trp Leu Lys Glu Ala Leu Leu Asn Gly Met Lys
```

```
Gly Arg Gln Pro Arg Trp Leu Lys Glu Ala Leu Leu Asn Gly Met Lys
 95                 100                 105                 110 aaa gaa gat ttt ctt gtg aag gac act gaa gaa gaa ata ata ccg ctg      987
Lys Glu Asp Phe Leu Val Lys Asp Thr Glu Glu Glu Ile Ile Pro Leu
                    115                 120                 125 aaa aat att taacataaaa taattaaatg ataacgataa ctgagctgg              1035
Lys Asn Ile <210> SEQ ID NO 15
<211> LENGTH: 129
<212> TYPE: PRT
<213> ORGANISM: Escherichia coli

<400> SEQUENCE: 15

Met Arg Arg Leu Phe Ile Met Asn Met Glu Thr Asn Ser His Thr Thr
 1               5                  10                  15

Ser Pro Tyr Ile Gln Leu Ile Glu Gln Ile Ala Val Leu Gln Gln Glu
             20                  25                  30

Ala Lys Arg Leu Arg Glu Gln Glu Val Gln Ser Val Ile Glu Ser Ile
         35                  40                  45

Gln Lys Gln Ile Thr Tyr Tyr Asn Ile Thr Leu Gln Glu Leu Gly Tyr
     50                  55                  60

Thr Asn Val Pro Asp Asp Gly Leu Ala Arg Arg Asn Ser Ser Lys Gly
 65                  70                  75                  80

Val Tyr Tyr Arg Asn Glu Glu Gly Gln Thr Trp Ser Gly Val Gly Arg
                 85                  90                  95

Gln Pro Arg Trp Leu Lys Glu Ala Leu Leu Asn Gly Met Lys Lys Glu
            100                 105                 110

Asp Phe Leu Val Lys Asp Thr Glu Glu Glu Ile Ile Pro Leu Lys Asn
        115                 120                 125

Ile

<210> SEQ ID NO 16
<211> LENGTH: 1026
<212> TYPE: DNA
<213> ORGANISM: Escherichia coli
<220> FEATURE:
<221> NAME/KEY: misc_feature
<223> OTHER INFORMATION: EHEC ler
<220> FEATURE:
<221> NAME/KEY: CDS
<222> LOCATION: (601)..(987)

<400> SEQUENCE: 16
agactaacgc ggttactgtt cagctatttg tcccttgttc cttttttataa tgcacccgtt      60 ccaggttagt gctggctgta gcttatgtcc gggaaacagc taatagatat atatactcgt     120
catacttcaa gttgcatgtg ctgcgactgc gttcgcttac cccaatcact tacttatgta     180
agctcctggg gattcactcg cttgccgcct tcctgtaact cgaattaagt agagtatagt     240
gaaacggttc agcttggttt ttattctgtt ttatttgttt atgcaatgag atctatctta     300
taaagagaaa cgcttaacta atggaaatg caattattaa agtcgtttgt taacgagatg      360 atttctcttct atatcattga ttttaaatgg attttaaaaa tatatgatt ttttgttgac      420 atttaatgat aatgtatttt acacattaga aaaagagaa taataacatt ttaaggtggt      480
tgtttgatga atagatgtg tcctaatttg atagataaac gttatctcac ataatttata      540
tcatttgatt aattgttggt ccttcctgat aaggtcgcta atagcttaaa atattaaagc      600 atg cgg aga tta ttt att atg aat atg gaa aat aat tca cat aca aca       648
```

```
                 Met Arg Arg Leu Phe Ile Met Asn Met Glu Asn Asn Ser His Thr Thr
                 1               5                   10                  15 agt cca tac att cag ctt ata gag caa att gca gtt cta cag cag gaa             696
Ser Pro Tyr Ile Gln Leu Ile Glu Gln Ile Ala Val Leu Gln Gln Glu
            20                  25                  30 gca aag cga ctg cga gag cag gaa gtt caa agt gta att gag tcg att             744
Ala Lys Arg Leu Arg Glu Gln Glu Val Gln Ser Val Ile Glu Ser Ile
            35                  40                  45 cag aag cag att act tat tac aat ata acc tta caa gag ctg gga tat             792
Gln Lys Gln Ile Thr Tyr Tyr Asn Ile Thr Leu Gln Glu Leu Gly Tyr
        50                  55                  60 act aat gtg cct gat gat gga ctc gct cgc cgg aac tca tcg aaa ggt             840
Thr Asn Val Pro Asp Asp Gly Leu Ala Arg Arg Asn Ser Ser Lys Gly
65                  70                  75                  80 gtt tac tac cgc aat gaa gaa ggg cag acc tgg tcg ggc gta ggc cga             888
Val Tyr Tyr Arg Asn Glu Glu Gly Gln Thr Trp Ser Gly Val Gly Arg
                85                  90                  95 cag cca cgc tgg ctt aaa gaa gca ctg ttg aat gga atg aag aaa gaa             936
Gln Pro Arg Trp Leu Lys Glu Ala Leu Leu Asn Gly Met Lys Lys Glu
            100                 105                 110 gat ttt ctt gtg aag gac act gaa gaa gaa ata ata ccg ctg aaa aat             984
Asp Phe Leu Val Lys Asp Thr Glu Glu Glu Ile Ile Pro Leu Lys Asn
            115                 120                 125 att taacatgaaa taattaaatg ataacgataa ctgagctgg                             1026
Ile <210> SEQ ID NO 17
<211> LENGTH: 129
<212> TYPE: PRT
<213> ORGANISM: Escherichia coli

<400> SEQUENCE: 17

Met Arg Arg Leu Phe Ile Met Asn Met Glu Asn Asn Ser His Thr Thr
1               5                   10                  15

Ser Pro Tyr Ile Gln Leu Ile Glu Gln Ile Ala Val Leu Gln Gln Glu
            20                  25                  30

Ala Lys Arg Leu Arg Glu Gln Glu Val Gln Ser Val Ile Glu Ser Ile
        35                  40                  45

Gln Lys Gln Ile Thr Tyr Tyr Asn Ile Thr Leu Gln Glu Leu Gly Tyr
    50                  55                  60

Thr Asn Val Pro Asp Asp Gly Leu Ala Arg Arg Asn Ser Ser Lys Gly
65                  70                  75                  80

Val Tyr Tyr Arg Asn Glu Glu Gly Gln Thr Trp Ser Gly Val Gly Arg
                85                  90                  95

Gln Pro Arg Trp Leu Lys Glu Ala Leu Leu Asn Gly Met Lys Lys Glu
            100                 105                 110

Asp Phe Leu Val Lys Asp Thr Glu Glu Glu Ile Ile Pro Leu Lys Asn
        115                 120                 125

Ile

<210> SEQ ID NO 18
<211> LENGTH: 718
<212> TYPE: DNA
<213> ORGANISM: Citrobacter rodentium
<220> FEATURE:
<221> NAME/KEY: misc_feature
<223> OTHER INFORMATION: ler
<220> FEATURE:
<221> NAME/KEY: CDS
<222> LOCATION: (293)..(682)
```

<400> SEQUENCE: 18

```
aattaatgga gaaacaataa ttaatgccgc tttgccaact agctaaatct ttataattta      60 ttgattttt  aatgatttt  taattggtat aatttttttg ttgacattta aggataatat    120 atttacaca  ttatgtatca ggggttaata gcttttatag gggttttgta tgatgaagta    180 gattttcta  atgtgataga taagacgtta tcttacataa tttataacat tctattaatt    240
gttgacccat ccatgtaagg atgagcttgt taatatctta atatataaaa gt atg agg    298
                                                        Met Arg
                                                        1
```

| aga tta ttt att atg aat atg gaa act aat tcg ccc aca aca agc cca | 346 |
|---|---|
| Arg Leu Phe Ile Met Asn Met Glu Thr Asn Ser Pro Thr Thr Ser Pro | |
| 5                  10                  15 | |

| tac att cag ctg att gag cag att gct gtg cta cag caa gaa gca aag | 394 |
|---|---|
| Tyr Ile Gln Leu Ile Glu Gln Ile Ala Val Leu Gln Gln Glu Ala Lys | |
| 20                  25                  30 | |

| cgg ctg cgt gag cag gag att caa act gta att gag tca att caa aaa | 442 |
|---|---|
| Arg Leu Arg Glu Gln Glu Ile Gln Thr Val Ile Glu Ser Ile Gln Lys | |
| 35              40                  45                  50 | |

| cag att act tat tac aat ata acc tta caa gaa ctg ggg tat act aat | 490 |
|---|---|
| Gln Ile Thr Tyr Tyr Asn Ile Thr Leu Gln Glu Leu Gly Tyr Thr Asn | |
|                   55                  60                  65 | |

| ata cct gat ggt gct ctt gct cgc cgg agc tca tca aaa ggg gta tac | 538 |
|---|---|
| Ile Pro Asp Gly Ala Leu Ala Arg Arg Ser Ser Ser Lys Gly Val Tyr | |
|             70                  75                  80 | |

| tac cgt aat gaa gac gga cag act tgg tct gga gtg ggt cga caa cca | 586 |
|---|---|
| Tyr Arg Asn Glu Asp Gly Gln Thr Trp Ser Gly Val Gly Arg Gln Pro | |
|         85                  90                  95 | |

| cgt tgg ctt aaa gaa gca tta ttg aat gga aga aag aaa gaa gat ttt | 634 |
|---|---|
| Arg Trp Leu Lys Glu Ala Leu Leu Asn Gly Arg Lys Lys Glu Asp Phe | |
|     100                 105                 110 | |

| ctt gtg aag gac aca gaa gaa gaa gta aca tct ctg aat aac att taa | 682 |
|---|---|
| Leu Val Lys Asp Thr Glu Glu Glu Val Thr Ser Leu Asn Asn Ile | |
| 115                 120                 125 | |

```
catgaaataa ttaaatgata acgataactg aactgg                              718
```

<210> SEQ ID NO 19
<211> LENGTH: 129
<212> TYPE: PRT
<213> ORGANISM: Citrobacter rodentium

<400> SEQUENCE: 19

```
Met Arg Arg Leu Phe Ile Met Asn Met Glu Thr Asn Ser Pro Thr Thr
1               5                   10                  15

Ser Pro Tyr Ile Gln Leu Ile Glu Gln Ile Ala Val Leu Gln Gln Glu
            20                  25                  30

Ala Lys Arg Leu Arg Glu Gln Glu Ile Gln Thr Val Ile Glu Ser Ile
        35                  40                  45

Gln Lys Gln Ile Thr Tyr Tyr Asn Ile Thr Leu Gln Glu Leu Gly Tyr
    50                  55                  60

Thr Asn Ile Pro Asp Gly Ala Leu Ala Arg Arg Ser Ser Ser Lys Gly
65                  70                  75                  80

Val Tyr Tyr Arg Asn Glu Asp Gly Gln Thr Trp Ser Gly Val Gly Arg
                85                  90                  95

Gln Pro Arg Trp Leu Lys Glu Ala Leu Leu Asn Gly Arg Lys Lys Glu
            100                 105                 110

Asp Phe Leu Val Lys Asp Thr Glu Glu Glu Val Thr Ser Leu Asn Asn
```

Ile

<210> SEQ ID NO 20
<211> LENGTH: 931
<212> TYPE: DNA
<213> ORGANISM: Escherichia coli
<220> FEATURE:
<221> NAME/KEY: misc_feature
<223> OTHER INFORMATION: RDEC-1 ler
<220> FEATURE:
<221> NAME/KEY: CDS
<222> LOCATION: (506)..(895)

<400> SEQUENCE: 20

```
ggacaaacat ggttgcttgt tctgccattt gttccttgtt cctttttata ccgccgccgc      60
tcccggtcag cactggggaa tagggggttg aggtatatct gctccttatg tcaggggaac     120
aggtaatagc tatatagcgg aacgtcttag tgctgtagtt attccatttt gctatttgtc     180
taataggact atcttaaaga aaacaaaacg attaactaaa tggaaaggca attgttaatg     240
gcgtttgcta agagatgaa gttcttctac tttattgatt tgaatgatt tttaagaaat      300 atgattttt tgttgacatt taatgataat gtgttttaca cattatgcat cggtgattaa      360
taacttttat aaggattttg tttgatgaag tagatgtgtt ctaatttgat agataaaacg     420
ttatctcaca taatttatat cattcgatta attgttgatc cttcctgata aggataagat     480
tgctaatagc ttaatatatt aaagc atg cgg aga tta ttt att atg aat atg       532
                            Met Arg Arg Leu Phe Ile Met Asn Met
                             1               5 gaa act aat tcg cac aca aca agc cca tac att cag ctt att gag caa       580
Glu Thr Asn Ser His Thr Thr Ser Pro Tyr Ile Gln Leu Ile Glu Gln
 10                 15                  20                  25 att gaa gtg tta caa cag gaa gca aag cga ctg cga gag cag gaa att      628
Ile Glu Val Leu Gln Gln Glu Ala Lys Arg Leu Arg Glu Gln Glu Ile
                 30                  35                  40 caa agt gta att gag tcg att caa aag cag att act tat tac aat ata      676
Gln Ser Val Ile Glu Ser Ile Gln Lys Gln Ile Thr Tyr Tyr Asn Ile
             45                  50                  55 acc cta caa gag ctg gga tat act aat gtg cct gat gat ggc ctt gct      724
Thr Leu Gln Glu Leu Gly Tyr Thr Asn Val Pro Asp Asp Gly Leu Ala
         60                  65                  70 cgc cgg aac tca tcg aaa gga gtt tat tat cgc aat gaa gaa ggg cag      772
Arg Arg Asn Ser Ser Lys Gly Val Tyr Tyr Arg Asn Glu Glu Gly Gln
     75                  80                  85 acc tgg tcg gga gtt ggc cga cag cca cgc tgg ctt aaa gaa gca ctg      820
Thr Trp Ser Gly Val Gly Arg Gln Pro Arg Trp Leu Lys Glu Ala Leu
 90                  95                 100                 105 ttg aat gga atg aag aaa gaa gat ttt ctt gtg aag gac acc gaa gac      868
Leu Asn Gly Met Lys Lys Glu Asp Phe Leu Val Lys Asp Thr Glu Asp
                110                 115                 120 gaa ata ata ccg ctg aaa aat att taa catgaaatca ttaaatgata           915
Glu Ile Ile Pro Leu Lys Asn Ile
            125 acgataactg aactgg                                                     931
```

<210> SEQ ID NO 21
<211> LENGTH: 129
<212> TYPE: PRT
<213> ORGANISM: Escherichia coli

<400> SEQUENCE: 21

```
Met Arg Arg Leu Phe Ile Met Asn Met Glu Thr Asn Ser His Thr Thr
1               5                   10                  15

Ser Pro Tyr Ile Gln Leu Ile Glu Gln Ile Glu Val Leu Gln Gln Glu
            20                  25                  30

Ala Lys Arg Leu Arg Glu Gln Glu Ile Gln Ser Val Ile Glu Ser Ile
        35                  40                  45

Gln Lys Gln Ile Thr Tyr Tyr Asn Ile Thr Leu Gln Glu Leu Gly Tyr
    50                  55                  60

Thr Asn Val Pro Asp Asp Gly Leu Ala Arg Arg Asn Ser Ser Lys Gly
65                  70                  75                  80

Val Tyr Tyr Arg Asn Glu Glu Gly Gln Thr Trp Ser Gly Val Gly Arg
                85                  90                  95

Gln Pro Arg Trp Leu Lys Glu Ala Leu Leu Asn Gly Met Lys Lys Glu
            100                 105                 110

Asp Phe Leu Val Lys Asp Thr Glu Asp Glu Ile Ile Pro Leu Lys Asn
        115                 120                 125

Ile

<210> SEQ ID NO 22
<211> LENGTH: 938
<212> TYPE: DNA
<213> ORGANISM: Escherichia coli
<220> FEATURE:
<221> NAME/KEY: misc_feature
<223> OTHER INFORMATION: E22 ler
<220> FEATURE:
<221> NAME/KEY: CDS
<222> LOCATION: (513)..(902)

<400> SEQUENCE: 22
```

| | | |
|---|---|---|
| ggacaaacat ggttgcttgt tctgccattt gttcattgtt ccttgttcct ttttataccg | 60 |
| ccgccgctcc cggtcagcac tggggaatag ggggttgagg tatatctgct ccttatgtca | 120 |
| ggggaacagg taatagctat atagcggaac gtcttagtgc tgtagttatt ccattttgct | 180 |
| atttgtctaa taggactatc ttaaagaaaa caaaacgatt aactaaatgg aaaggcaatt | 240 |
| gttaatggcg tttgctaaag agatgaagtt cttctaccct attgattttg aatgattttt | 300 |
| aagaaatatg ttttttttgt tgacatttaa tgataatgtg ttttacacat tatacatcgg | 360 |
| tgattaataa cttttataag gatttgtttt gatgaagtag atgtgttcta atttgataga | 420 |
| taaaacgtta tctcacataa tttatatcat tcgattaatt gttgatcctt cctgataagg | 480 |
| ataagattgc taatagctta atatattaaa gc atg cgg aga tta ttt att atg | 533 |

```
                                    Met Arg Arg Leu Phe Ile Met
                                    1               5
```

| | |
|---|---|
| aat atg gaa act aat tcg cac aca aca agc cca tac att cag ctt att | 581 |

```
Asn Met Glu Thr Asn Ser His Thr Thr Ser Pro Tyr Ile Gln Leu Ile
        10                  15                  20
```

| | |
|---|---|
| gag caa att gaa gtg tta caa cag gaa gca aag cga ctg cca gag cag | 629 |

```
Glu Gln Ile Glu Val Leu Gln Gln Glu Ala Lys Arg Leu Pro Glu Gln
    25                  30                  35
```

| | |
|---|---|
| gaa att caa agt gta att gag tcg att caa aag cag act acc tat tac | 677 |

```
Glu Ile Gln Ser Val Ile Glu Ser Ile Gln Lys Gln Thr Thr Tyr Tyr
40                  45                  50                  55
```

| | |
|---|---|
| aat ata acc cta caa gag ctg gga tat act aat gtg cct gat gat ggc | 725 |

```
Asn Ile Thr Leu Gln Glu Leu Gly Tyr Thr Asn Val Pro Asp Asp Gly
            60                  65                  70
```

| | |
|---|---|
| ctt gct cgc cgg aac tca tcg aaa aga gtt tat tat cgc aat gaa gaa | 773 |

```
Leu Ala Arg Arg Asn Ser Ser Lys Arg Val Tyr Tyr Arg Asn Glu Glu
```

-continued

```
                         75                  80                  85
ggg cag acc tgg tcg gga gtt ggc cga cag cca cgc tgg ctt aaa gaa      821
Gly Gln Thr Trp Ser Gly Val Gly Arg Gln Pro Arg Trp Leu Lys Glu
             90                  95                 100 gca ctg ttg aat gga atg aag aaa gaa gat ttt ctt gtg aag gac acc      869
Ala Leu Leu Asn Gly Met Lys Lys Glu Asp Phe Leu Val Lys Asp Thr
105                 110                 115 gaa gac gaa ata ata ccg ctg aaa aat att taa catgaaatca ttaaatgata    922
Glu Asp Glu Ile Ile Pro Leu Lys Asn Ile
120                 125 acgataactg aactgg                                                    938

<210> SEQ ID NO 23
<211> LENGTH: 129
<212> TYPE: PRT
<213> ORGANISM: Escherichia coli

<400> SEQUENCE: 23

Met Arg Arg Leu Phe Ile Met Asn Met Glu Thr Asn Ser His Thr Thr
1               5                   10                  15

Ser Pro Tyr Ile Gln Leu Ile Glu Gln Ile Glu Val Leu Gln Gln Glu
            20                  25                  30

Ala Lys Arg Leu Pro Glu Gln Glu Ile Gln Ser Val Ile Glu Ser Ile
        35                  40                  45

Gln Lys Gln Thr Thr Tyr Tyr Asn Ile Thr Leu Gln Glu Leu Gly Tyr
    50                  55                  60

Thr Asn Val Pro Asp Asp Gly Leu Ala Arg Arg Asn Ser Ser Lys Arg
65                  70                  75                  80

Val Tyr Tyr Arg Asn Glu Glu Gly Gln Thr Trp Ser Gly Val Gly Arg
                85                  90                  95

Gln Pro Arg Trp Leu Lys Glu Ala Leu Leu Asn Gly Met Lys Lys Glu
            100                 105                 110

Asp Phe Leu Val Lys Asp Thr Glu Asp Glu Ile Ile Pro Leu Lys Asn
        115                 120                 125

Ile

<210> SEQ ID NO 24
<211> LENGTH: 29
<212> TYPE: PRT
<213> ORGANISM: Escherichia coli
<220> FEATURE:
<221> NAME/KEY: misc_feature
<223> OTHER INFORMATION: REPEC(delta)ler

<400> SEQUENCE: 24

Met Arg Arg Leu Phe Ile Met Asn Met Glu Thr Asn Ser His Ile Val
1               5                   10                  15

Lys Asp Thr Glu Glu Glu Ile Ile Pro Leu Lys Asn Ile
            20                  25

<210> SEQ ID NO 25
<211> LENGTH: 31
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: end of RDEC-1 eae coding sequence

<400> SEQUENCE: 25
```

```
aacaaatgta agacaaatag cgcaaattta g                              31
```

<210> SEQ ID NO 26
<211> LENGTH: 30
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: end of RDEC-1(delta)eae coding sequence

<400> SEQUENCE: 26

```
aacaatgtaa gacaaatagc gcaaatttag                                30
```

<210> SEQ ID NO 27
<211> LENGTH: 19
<212> TYPE: DNA
<213> ORGANISM: Artificial
<220> FEATURE:
<223> OTHER INFORMATION: Synthetic

<400> SEQUENCE: 27

```
gatacgccaa acacatctt                                            19
```

<210> SEQ ID NO 28
<211> LENGTH: 20
<212> TYPE: DNA
<213> ORGANISM: Artificial
<220> FEATURE:
<223> OTHER INFORMATION: Synthetic

<400> SEQUENCE: 28

```
tcaaaccaag gccagcatta                                           20
```

<210> SEQ ID NO 29
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Stx 2AB 2A forward primer

<400> SEQUENCE: 29

```
aggaaggtgc gaccgtaatt                                           20
```

<210> SEQ ID NO 30
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Stx2AB 2B reverse primer

<400> SEQUENCE: 30

```
atacaggtgt tccttttggc                                           20
```

<210> SEQ ID NO 31
<211> LENGTH: 40
<212> TYPE: DNA
<213> ORGANISM: Artificial
<220> FEATURE:
<223> OTHER INFORMATION: Synthetic

```
<220> FEATURE:
<221> NAME/KEY: misc_feature
<223> OTHER INFORMATION: Stx2AB 2C forward primer

<400> SEQUENCE: 31
tgccaaaagg aacacctgta tggcataacc tgattcgtgg                              40

<210> SEQ ID NO 32
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Stx2AB 2D reverse primer

<400> SEQUENCE: 32
gtgcctggct cctctggtgt                                                    20

<210> SEQ ID NO 33
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Stx2AB 2E forward primer

<400> SEQUENCE: 33
tcatatctgg cgttaatgga                                                    20

<210> SEQ ID NO 34
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Stx1AB 1A forward primer

<400> SEQUENCE: 34
catcaccttc tgcgacaatc                                                    20

<210> SEQ ID NO 35
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Stx1AB 1B reverse primer

<400> SEQUENCE: 35
cttagaatag ctcagtgaaa                                                    20

<210> SEQ ID NO 36
<211> LENGTH: 40
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Stx1AB 1C forward primer
```

<400> SEQUENCE: 36
tttcactgag ctattctaag attacacaat actccttgag                    40

<210> SEQ ID NO 37
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Stx1AB 1D reverse primer

<400> SEQUENCE: 37
gtgctctgac acctgtatag                                          20

<210> SEQ ID NO 38
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Stx1AB 1E forward primer

<400> SEQUENCE: 38
tgtatatttt aagtattgca                                          20

<210> SEQ ID NO 39
<211> LENGTH: 31
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Intimin (RDEC-1) eae1A forward primer

<400> SEQUENCE: 39
tcccccgggg gagggggcaaa agtgccagaa c                            31

<210> SEQ ID NO 40
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Intimin (RDEC-1) eae1B reverse primer

<400> SEQUENCE: 40
tttgttttcg gcatcaaaat                                          20

<210> SEQ ID NO 41
<211> LENGTH: 48
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Intimin (RDEC-1) eae1C forward primer

<400> SEQUENCE: 41
attttgatgc cgaaaacaaa gtcgactaat ttaattacat ctcaaatc           48

<210> SEQ ID NO 42
<211> LENGTH: 32
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Intimin (RDEC-1) eae1D reverse primer

<400> SEQUENCE: 42
tcccccgggg gattcttcct gttatcggga ta                                    32

<210> SEQ ID NO 43
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Intimin (RDEC-1) eae1E forward primer

<400> SEQUENCE: 43
ggtgataaag tgaccgtaat                                                  20

<210> SEQ ID NO 44
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Intimin (EHEC) eaeA forward primer

<400> SEQUENCE: 44
acgccaggag ttgcaggatg                                                  20

<210> SEQ ID NO 45
<211> LENGTH: 47
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Intimin (EHEC) eaeB reverse primer

<400> SEQUENCE: 45
cctattatgc tgatgctatg gtcgactaat tccataacca ccccggc                    47

<210> SEQ ID NO 46
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Intimin (EHEC) eaeC forward primer

<400> SEQUENCE: 46
catagcatca gcataatagg                                                  20

<210> SEQ ID NO 47
<211> LENGTH: 20
<212> TYPE: DNA

```
<213> ORGANISM: Artificial
<220> FEATURE:
<223> OTHER INFORMATION: Synthetic
<220> FEATURE:
<221> NAME/KEY: misc_feature
<223> OTHER INFORMATION: Intimin (EHEC) eaeD reverse primer

<400> SEQUENCE: 47
ggttatattt tttgatcaaa                                                        20

<210> SEQ ID NO 48
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Intimin (EHEC) eaeE forward primer

<400> SEQUENCE: 48
tagacatttg gagtattaac                                                        20

<210> SEQ ID NO 49
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: lerA forward primer

<400> SEQUENCE: 49
ttgctggact cagtgtctct                                                        20

<210> SEQ ID NO 50
<211> LENGTH: 40
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: lerB reverse primer

<400> SEQUENCE: 50
tgaatatgga aataattca taacatgaaa taattaaatg                                   40

<210> SEQ ID NO 51
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: lerC forward primer

<400> SEQUENCE: 51
tgaattattt tccatattca                                                        20

<210> SEQ ID NO 52
<211> LENGTH: 20
<212> TYPE: DNA
<213> ORGANISM: Artificial
<220> FEATURE:
<223> OTHER INFORMATION: Synthetic
<220> FEATURE:
```

<221> NAME/KEY: misc_feature
<223> OTHER INFORMATION: lerD reverse primer

<400> SEQUENCE: 52
caggttagtg ctggctgtag                                               20

<210> SEQ ID NO 53
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: lerE reverse primer

<400> SEQUENCE: 53
tgcctgatga tggactcgct                                               20

<210> SEQ ID NO 54
<211> LENGTH: 19
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: tirA forward primer

<400> SEQUENCE: 54
caggcgcatc ggatttaca                                                19

<210> SEQ ID NO 55
<211> LENGTH: 44
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: tirB reverse primer

<400> SEQUENCE: 55
gtaaatccga tgcgcctggt cgacatatat ccataatcat ttta                    44

<210> SEQ ID NO 56
<211> LENGTH: 19
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: tirC forward primer

<400> SEQUENCE: 56
caggcgcatc ggatttaca                                                19

<210> SEQ ID NO 57
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: tirD reverse primer

<400> SEQUENCE: 57

-continued ctggtgtata gcatggcctt                                                    20

<210> SEQ ID NO 58
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: tirE forward primer

<400> SEQUENCE: 58
ccagataatc aaaaagttaa                                                    20

<210> SEQ ID NO 59
<211> LENGTH: 2805
<212> TYPE: DNA
<213> ORGANISM: Escherichia coli
<220> FEATURE:
<221> NAME/KEY: misc_feature
<223> OTHER INFORMATION: EHEC O157 eae

<400> SEQUENCE: 59
ttattctaca caaaccgcat agacatttgg agtattaaca ttaaccccag gaagagggtt        60
ttgtgttatt aggttataag tgcttgatac tccagaacgc tgctcactag atgtctgttt      120
aatccaagca gttattgagt tcatagaact ataatggcta tatttatttg cagcccccca      180
tgagtcataa atatctgaca ataccgtctg tgtggatggt aataaatttt tgcaaatgga      240
catagcatca gcataatagg cttgcttatc cacttttatc atatacgacg gtgcttttat      300
agtgtaactt actgtttgct tatcaccaga tgtggcttta attacgacac tgcctttacc      360
attcaaagtg actttccctg atgcatcgac agtcgcgata ctggtatttt ctgaatacca      420
tgaatatgta ccatcaccac cgcttgcttt cagtttaaac tgaccatatt gcagccaaat      480
attaggcaac tcgcctctga cattgttacc aataatatca accttgttgt caatttttcag     540 ttcatcaaaa aaagtgacct cagtcgcttt aacctcagcc ccatcactga ctgtcgcact      600
aacagtcgct ttaccggcgg aactggaagt tagtgttatc gtcgcacgac catcatttcc     660
cgtggttgct tgcgtttgag acttaccgtt gaacatccca agtttgttg agaatgtaac      720 ggattgatta ttaactggct gaccgttttt cataactttt acagtatatt taatagcatc     780 cttaccatttt gctactgcag ttgtcttatc agccttaatc tcagtaatgc tggccttggt    840
ttgatcaaaa aatataaccg cactggcatt aagtgctgaa gtcatctccg cggttttagc      900
agacacgacg acctgtcctg gcgtactcga cttcaacgtt acggttgcct taccgttagc      960
atccgttttg gcactatttg ccccaagagt tgcagttcct gaaacaatat taaatgaaac     1020
agggacatta gcctgagcta cccccattctt tttcaccgtc gcggtataag taatggtatc    1080
ggcgttatcc gctttagccg aagtcttatc cgccgtaaag tccgttaccc caacctggtc    1140
gacaacttga ccattcgaca gaacggtaat agtaagctgt acattgttag agctattgcc    1200
attacggtca taggcgcgag ccgtcacttt ataaatattg ctgccaacctt gcacataagc   1260 aggcaaaata gcctggtagt cttgtgcgct ttggcttccg ctatgctgaa tctgaccgcc     1320
ctgactgcgt aatgcactat catcccagac gatacgatcc agaccgtatt gctcttaac      1380 gatcaactga atcttctgcg tactgtgttc agtaccatta atatcatgcg gaatattcag     1440
agaaagaata tcctgcttct tgtactccag aataatattg ttattacgct gaaccagatc     1500

-continued

```
gtaacggctg cctgataatg ttcttaactc gttaacatac tgtggttcaa tttgctgaga      1560
ccacgattta tcaaactgat aacggaactg cattgagtaa aggagatcat tttcattacc      1620
cgtaccatga cggtaatcga tccccatcgt caccagagga atcggagtat agtttacacc      1680
aacggtcgcc gcaccaggat tcgactgcag cttatcagaa ttaaacaaag caacattatc      1740
accataatac tgctcatata tcagcttggc gcctaatgcc ggatatgacg gtagatagcc      1800
attaaaacgg atatcgaagc catttgctgg gcgctcatca tagtctttct tattgtatga      1860
ctcatgccag ccgctcatgc ggaaatagcc gttaacgcta cttttgaaat agtctcgcca      1920
gtattcgcca ccaatacctca aacgggtatt atcaccagaa aaatcctgat caatgaagac      1980
gttatagccc aacatgtttg caggaaggaa aaaacgctga cccgcaccta aatttgccgt      2040
aaagcgggag tcaatgtaac gcgctccgac ctgaccaaat gccagcattt tttcggaatc      2100
atagaacggt aataagaagt ccagtgaact accgtcaaag ttattaccac tctgcagatt      2160
aacctctgcc gttccataat gttgtaacca ggcctgcaac tgtgacgaag cctggttacc      2220
agcgatacca agagcggtat ctttcgcgta atcgccgttc agagatcgcg actgaagctg      2280
gctaccgaga ctcgccgcct gttgtgccgc ataatttaat gccttgtcat cggtcatgtt      2340
gcttttggtc acgtccgggg acattttagt cagtttattc gtgtgaccag caacaccacc      2400
tgcagcaaca agaggtgccg aacctaaaag tggtagtgca ctgtattcaa agggaagttt      2460
tttgagtggc aaaatgatct gctgaccagg cgcggccttc atcatttcgc tttcagaact      2520
gtataaatgc ttattcaacg accaaatcgt cgataaatta atatcttgcg atttagaaag      2580
atcggcaaca gtttcaccag ttttcaacgt ataaaaaagg cgattctgat agctatcatg      2640
agttaacagt tttgaatccg aacccaattt aaaataattt tcaccatttg caaatgaatt      2700
ctgattaaca taaaaaaaca atcctaaacc agcactaagc ataatcaatg ttttttttag      2760
cttatgcttg tgccgggtcc gggtataaca accatgagta atcat                     2805
```

<210> SEQ ID NO 60
<211> LENGTH: 1617
<212> TYPE: DNA
<213> ORGANISM: Escherichia coli
<220> FEATURE:
<221> NAME/KEY: misc_feature
<223> OTHER INFORMATION: RDEC-1 tir

<400> SEQUENCE: 60

```
atgcctattg gtaatcttgg ccacaattcc aatgtgagag ctttaattcc acctgcaccg        60
ccattacctt cacaaaccga cggtgcagga ggtgcccgta atcagctcat taactcaaat       120
ggcccgatgg ggtctcgttt gctatttacg cctatcagga attctgttgc tgatgctgct       180
gattctcgtg ccagtgatat tcccggactt cctacaaatc cactgcgctt tgctgcgtcc       240
gaggtatctt tgcatggtgc gcttgaagtt cttcatgata aggggggct tgatactctt       300 aactctgcta ttggatcttc gttattccgt gttgaaactc gggatgatgg cagccatgtt       360
gctatcgggc aaaaaaatgg cctcgagacc actgttgttt taagtgagca agagtttct        420 agcttacagt cccttgatcc tgaaggtaaa aacaaatttg tatttactgg aggccgcggt      480
ggcgcagggc atgctatggt cacgttgct tcagatatcg ccgaagcccg tcagaggata      540
atagataaat tagaaccaaa ggatacaaag gagacgaagg agccagggga tccaaatagt      600
ggcgagggaa aaatcattga aattcatacc tcaacctcaa cttctagcct ccgtgcagat      660
cctaaacttt ggttgtcatt ggggactatt gctgcaggtc tgatagggat ggctgcgacg      720
```

```
gggattgcac aggctgttgc gttgactcca gagccggatg acccaatcac taccgaccct      780
gatgctgcag caaacacagc tgaagcagcg gcaaaagatc agttaacgaa agaagcattc      840
cagaacccag ataaccagaa agttaatatc gatgagaacg gaaatgcaat tccgtccggg      900
gaactaaaag atgatgttgt tgcgcaaata gcagaacaag ctaaagcggc gggtgaacag      960
gccagacagg aagctattga agtaattcct caggcgcagc aaaaatatga tgaacagcat     1020
gctaaacgcg aacaggaaat gtctctttca tcggggggttg gctacggtat tagtggtgcg     1080
ctgattcttg gcgggggaat tggtgccggt gttactgctg ctcttcatcg aaaaaccaa      1140 ccggcagaac aaacaatcac tacacgtacg gtagtcgata atcagcctac gaataacgca     1200
tctgcgcagg gcaatactga cacaagtggg ccagaagagt ccccggcgag cagacgtaat     1260
tcgaatgcca gcctcgcatc gaacgggtct gacacctcca gcacgggcac ggtagagaat     1320
ccgtatgctg acgttggaat gcccagaaat gattcactgg ctcgcatttc agaggaacct     1380
atttatgatg aggtcgctgc agatcctaat tatagcgtca ttcaacattt ttcagggaac     1440
agcccagtta ccggaaggtt agtgggaacc ccagggcaag gtatccaaag tacttatgcg     1500
cttctggcaa gcagcggcgg attgcgttta ggtatgggag gattaacggg ggggggcgag     1560
agcgcagtaa gtactgccaa tgccgcacca acgccgggac ccgcacgttt cgtttaa       1617

<210> SEQ ID NO 61
<211> LENGTH: 1677
<212> TYPE: DNA
<213> ORGANISM: Escherichia coli
<220> FEATURE:
<221> NAME/KEY: misc_feature
<223> OTHER INFORMATION: O157:H7 tir

<400> SEQUENCE: 61
ttagacgaaa cgatgggatc ccggcgctgg tgggttattc gaagtattca cagcgctatt       60
actccccccc gttaatcctc ccatgtcatg gcgtaatcca ccacttagcg ccagacgcgc      120
ataagtgctt tgaatccccg cacttggatt tcctaataac cgtgcgccgt tatcagtagt      180
atcccgggga ggatgttgaa tggtgctata tacaacagaa tctgtattcc ccatattctg      240
aacagacgta ttagaattag aagtcggcac ctgcgaatca tgcagcgatg ttttaacatc      300
agcatacgga ttctgcacgg tccctatgct ggaagtgtca agaaagtcg acgaggtgct      360 agccatcgag ctacgtctgc tctccatggt atcttctgac ccaggggtat ctacattgcc      420
ctgtgcaggt gtattatttg caggcttatt ctctaccgta cgtgcgcttg tagttgtagt      480
tgtagtagtt gttgttgttg tttgttctac cggctgattt tttcgatgaa gcgcagcggt      540
gacggcaaca ccaattcccc caccaagaat caatgcgcca ctaagaccgt agccagcccc      600
cgatgaaact ttcagctcct cctggcgttt agcttgttgt tcatcatatt ttttttgcgc      660
ctgagcatta ttttcaatgg cttgctgttt ggcctcttcg cctgctgctt tagcctgctc      720
ttctatattc gcaacaacat catctttcaa taccccctgac ggaatcgcat ttccgagctc      780
atcgatatta acttttttgat tatctggggtt ctggaacgct tctttcgtta actgatctct      840
tgtcgcagtt tcagttgcac ttgcagctgc atcagggtcg gtcgtggttg gctatccgg      900 ctccggcgtc aatgcaagcg cctgtacaat acccgtcgcc gccaacccta tcagacctgt      960
agcaacagtc cccaacgcca accaaagttt aggatctgaa cgaaggctgg aagttgaggt     1020
tgaggtctga gttctgtgg tgttttccgc accgctattt gactccctca actccccaac     1080 gcctttttgac tccccagcac ctttggactc cccggtccct ttgggctcta acagctccag     1140
```

| | | | | |
|---|---|---|---|---|
| tatcctttgg | cgggcttccg | tgatatctga | agcaacggtg | accatagcat gcccagcacc | 1200 |
| accacggcct | ccagtaaata | caaatttgtc | tttaccttca | ggatcaatgg actgcaagcg | 1260 |
| agcgtactct | tgatcactta | aaacaacaga | ggtctcaaca | ccattcctct gaccgacagc | 1320 |
| aatatgttta | ccatcttcct | gagtttcaac | tcgaaatacc | gaagagccaa tctgcctgtt | 1380 |
| aagagtatcg | agcggaccat | gatcatgaag | aacttcaaat | ccatcattca gtgttatctc | 1440 |
| agacgccgcc | aggcgcatcg | gatttacagg | aagtccagga | acatcactgg cacgattgtc | 1500 |
| gccagaatca | gccatagaat | tccttacagg | cgtaaatagc | gcacgagatc caacggccc | 1560 |
| cgtagagtta | atgagctgac | cacgccccc | tgcaccgtcg | gtttgtgaag gtaatggagg | 1620 |
| tgcaggagga | attgaattat | tcacattggg | attatgacca | agattaccaa taggcat | 1677 |

<210> SEQ ID NO 62
<211> LENGTH: 1227
<212> TYPE: DNA
<213> ORGANISM: Escherichia coli
<220> FEATURE:
<221> NAME/KEY: misc_feature
<223> OTHER INFORMATION: Stx1AB

<400> SEQUENCE: 62

```
tcaacgaaaa ataacttcgc tgaatccccc tccattatga caggcattag ttttaatggt     60
tacagtcatc cccgtaattt gcgcactgag aagaagagac tgaagattcc atctgttggt    120
aaataattct ttatcaccca ctttaactgt aaaggtatcg tcatcattat attttgtata    180
ctccaccttt ccagttacac aatcaggcgt cgccagcgca cttgctgaaa aaaatgaaag    240
cgatgcagct attaataatg ttttttttcat tttacccccct caactgctaa tagttctgcg    300
catcagaatt gcccccagag tggatgaatc ccacaatatt ttattgtgcg taatcccacg    360
gactcttcca tctgccggac acatagaagg aaactcatca gatgccattc tggcaactcg    420
cgatgcatga tgatgacaat tcagtattaa tgccacgctt cccagaattg cattaatgct    480
tccaaaagaa attcttccta cacgaacaga gtcttgtcca tgataatcag gcaggacact    540
actcaacctt ccccagttca atgtaagatc aacatcttca gcagtcatta cataagaacg    600
cccactgaga tcatccagtg ttgtacgaaa tcccctctgt atttgccgaa aacgtaaagc    660
ttcagctgtc acagtaacaa accgtaacat cgctcttgcc acagactgcg tcagtgaggt    720
tccactatgc gacattaaat ccagataaga agtagtcaac gaatggcgat ttatctgcat    780
ccccgtacga ctgatccctg caacacgctg taacgtggta tagctactgt caccagacaa    840
tgtaaccgct gttgtacctg gaaaggtaac atgtgaaaaa tcagcaaagc gataaaaaac    900
attatttgtc ctgttaacaa atcctgtcac atataaatta tttcgttcaa caataagccg    960
tagattatta aaccgccctt cctctggatc tatccctctg acatcaactg caaacaaatt   1020
atcccctgtg ccactatcaa tcatcagtaa agacgtacct cctgatgaaa tagtctgtaa   1080
tggagtacct attgcagagc gaatgacatt cagcgaatct acatacgtct ttgcagtcga   1140
gaagtctaag gtaaattcct tcgcaaccac attaactgaa aagataacaa agaaaaaagt   1200
tagcactcta aaaataatta ttttcat                                        1227
```

<210> SEQ ID NO 63
<211> LENGTH: 1241
<212> TYPE: DNA
<213> ORGANISM: Escherichia coli
<220> FEATURE:
<221> NAME/KEY: misc_feature
<223> OTHER INFORMATION: Stx2AB

```
<400> SEQUENCE: 63
atgaagtgta tattatttaa atgggtactg tgcctgttac tgggtttttc ttcggtatcc      60
tattcccggg agtttacgat agactttcg acccaacaaa gttatgtctc ttcgttaaat     120
agtatacgga cagagatatc gacccctctt gaacatatat ctcaggggac cacatcggtg     180
tctgttatta accacacccc accgggcagt tattttgctg tggatatacg agggcttgat     240
gtctatcagg cgcgttttga ccatcttcgt ctgattattg agcaaaataa tttatatgtg     300
gccgggttcg ttaatacggc aacaaatact ttctaccgtt tttcagattt tacacatata     360
tcagtgcccg gtgtgacaac ggtttccatg acaacggaca gcagttatac cactctgcaa     420
cgtgtcgcag cgctggaacg ttccggaatg caaatcagtc gtcactcact ggtttcatca     480
tatctggcgt taatggagtt cagtggtaat acaatgacca gagatgcatc cagagcagtt     540
ctgcgttttg tcactgtcac agcagaagcc ttacgcttca ggcagataca gagagaattt     600
cgtcaggcac tgtctgaaac tgctcctgtg tatacgatga cgccgggaga cgtggacctc     660
actctgaact gggggcgaat cagcaatgtg cttccggagt atcggggaga ggatggtgtc     720
agagtgggga gaatatcctt taataatata tcagcgatac tggggactgt ggccgttata     780
ctgaattgcc atcatcaggg ggcgcgttct gttcgcgccg tgaatgaaga gagtcaacca     840
gaatgtcaga taactggcga caggcctgtt ataaaaataa acaatacatt atgggaaagt     900
aatacagctg cagcgtttct gaacagaaag tcacagtttt tatatacaac gggtaaataa     960
aggagttaag catgaagaag atgtttatgg cggtttatt tgcattagct tctgttaatg    1020
caatggcggc ggattgtgct aaaggtaaaa ttgagttttc caagtataat gaggatgaca    1080
catttacagt gaaggttgac gggaaagaat actggaccag tcgctggaat ctgcaaccgt    1140
tactgcaaag tgctcagttg acaggaatga ctgtcacaat caaatccagt acctgtgaat    1200
caggctccgg atttgctgaa gtgcagttta ataatgactg a                        1241
```